(12) United States Patent
Cherone et al.

(10) Patent No.: US 12,662,516 B2
(45) Date of Patent: Jun. 23, 2026

(54) DNA BINDING PROTEINS FOR DISPLACING ENDOGENOUS TRANSCRIPTION FACTORS BOUND TO GENE REGULATORY REGIONS

(71) Applicant: Altius Institute for Biomedical Sciences, Seattle, WA (US)

(72) Inventors: Jennifer M. Cherone, Seattle, WA (US); Alister PW Funnell, Seattle, WA (US); John A. Stamatoyannopoulos, Seattle, WA (US)

(73) Assignee: Altius Institute for Biomedical Sciences, Seattle, WA (US)

( * ) Notice: Subject to any disclaimer, the term of this patent is extended or adjusted under 35 U.S.C. 154(b) by 1112 days.

(21) Appl. No.: 17/764,497

(22) PCT Filed: Oct. 14, 2020

(86) PCT No.: PCT/US2020/055534
§ 371 (c)(1),
(2) Date: Mar. 28, 2022

(87) PCT Pub. No.: WO2021/076592
PCT Pub. Date: Apr. 22, 2021

(65) Prior Publication Data
US 2023/0227513 A1     Jul. 20, 2023

Related U.S. Application Data

(60) Provisional application No. 62/915,388, filed on Oct. 15, 2019.

(51) Int. Cl.
| | |
|---|---|
| *C07H 21/02* | (2006.01) |
| *A61P 7/06* | (2006.01) |
| *C07K 14/47* | (2006.01) |
| *C07K 14/805* | (2006.01) |
| *A61K 38/00* | (2006.01) |

(52) U.S. Cl.
CPC ............ *C07K 14/4702* (2013.01); *A61P 7/06* (2018.01); *C07K 14/805* (2013.01); *A61K 38/00* (2013.01); *C07K 2319/80* (2013.01)

(58) Field of Classification Search
CPC ................................................ C07K 14/4702
See application file for complete search history.

(56) References Cited

U.S. PATENT DOCUMENTS

| | | | | |
|---|---|---|---|---|
| 9,963,715 | B2 * | 5/2018 | Cost | A61P 7/06 |
| 11,795,443 | B2 * | 10/2023 | Liu | C12N 15/113 |
| 2005/0079512 | A1 | 4/2005 | Emerson et al. | |
| 2006/0182736 | A1 | 8/2006 | Kim et al. | |
| 2013/0280222 | A1 | 10/2013 | Kay et al. | |
| 2015/0132821 | A1 | 5/2015 | Fine et al. | |
| 2019/0119697 | A1 | 4/2019 | Dubald et al. | |
| 2019/0323031 | A1 | 10/2019 | Fahrenkrug et al. | |

FOREIGN PATENT DOCUMENTS

| | | |
|---|---|---|
| WO | 2013016434 A1 | 1/2013 |
| WO | 2013082519 A2 | 6/2013 |
| WO | 2016/037138 | 3/2016 |
| WO | WO 2021/076592 | 4/2021 |
| WO | 2022/221694 | 10/2022 |

OTHER PUBLICATIONS

Hubbard et al. (Nature Methods, 12, 10, 2015, 939-944).*
Zittersteijn et al., (2021) "A Small Key for a Heavy Door: Genetic Therapies for the Treatment of Hemoglobinopathies", Frontiers in Genome Editing, 2:1-25.
Liu et al., (2021) "Transcription factor competition at the y-globin promoters controls hemoglobin switching", Nature Genetics, 53(4):511-520.
Lux et al., (2019) "TALEN-Mediated Gene Editing of HBG in Human Hematopoietic Stem Cells Leads to Therapeutic Fetal Hemoglobin Induction", Molecular Therapy: Methods & Clinical Development, 12:175-183.
Thakore et al., (2016) "Design, Assembly, and Characterization of TALE-Based Transcriptional Activators and Repressors", Methods Mol Biol, 1338:71-88.
Doyle et al., (2012) "TAL Effector-Nucleotide Targeter (TALE-NT) 2.0: tools for TAL effector design and target prediction", Nucleic Acids Research, 40:W117-W122.
Feng et al., (1994) "Analyses of beta-Thalassemia Mutant DNA Interactions with Erythroid Kriippel-like Factor (EKLF), an Erythroid Cell-specific Transcription Factor", Journal of Biological Chemistry, 269(2):1493-1500.
Masuda et al. (2016) "Transcription factors LRF and BCL11A independently repress expression of fetal hemoglobin", Science, 351(6270):285-289.

* cited by examiner

*Primary Examiner* — Amy Rose Hudson
(74) *Attorney, Agent, or Firm* — Shweta Chandra; Bozicevic, Field & Francis LLP

(57)     ABSTRACT

The present disclosure provides methods and compositions for modulating expression of a target gene in a cell by reducing binding of an endogenous transcription factor to a regulatory sequence of the target gene. The method includes introducing into the cell a DNA binding polypeptide (DBF) that binds a sequence in regulatory region of a target gene bound by a transcription factor (TF), thereby displacing the TF and modulating expression of the target gene. The DBF may be designed to bind a sequence comprising the binding site for the TF and additional nucleotides present on one or both sides of the sequence. Accordingly, the DBF specifically binds to binding site for the TF in the target gene but not in other genes that are also regulated by binding of the TF but do not include the nucleotides present on one or both sides of the sequence.

20 Claims, 8 Drawing Sheets
Specification includes a Sequence Listing.

DNA BINDING PROTEINS FOR DISPLACING ENDOGENOUS TRANSCRIPTION FACTORS BOUND TO GENE REGULATORY REGIONS

CROSS-REFERENCE TO RELATED APPLICATIONS

This application claims priority to U.S. Provisional Application Ser. No. 62/915,388 filed Oct. 15, 2019, the disclosure of which is herein incorporated by reference in its entirety.

INCORPORATION BY REFERENCE OF SEQUENCE LISTING PROVIDED AS A TEXT FILE

A Sequence Listing is provided herewith as a text file, "ALTI-720WO Seq List_ST25.txt," created on Apr. 18, 2019 and having a size of 240 KB. The contents of the text file are incorporated by reference herein in their entirety.

INTRODUCTION

Transcription factors are frequently targeted for modulating gene expression. Modulation of gene expression is useful in studying protein function as well as in treating diseases.

Anemia, a red blood cell disorder, can be defined as a reduction in the ability of blood to transport oxygen. The majority of red blood cell disorders are caused by genetic defects that result in abnormal hemoglobin, such as, sickle cell syndromes; low hemoglobin, such as, thalassemia syndromes; or both, e.g., syndromes associated with unstable hemoglobins.

Fetal globin (also known as hemoglobin gamma "HBG" or gamma globin) normally combines with alpha globin chains prenatally to form fetal hemoglobin (HbF). Fetal globin is replaced by beta globin or hemoglobin beta (HBB) after birth, which then combines with alpha globin to form adult hemoglobin A. Fetal globin performs the same function as beta globin, and can combine with the alpha chains to generate a healthy form of hemoglobin.

The various types of beta thalassemias are syndromes resulting from mutations, which produce a deficiency of beta globin chains. In beta thalassemia, the unmatched alpha globin chains aggregate inside red blood cells (RBCs) and their progenitors, causing the premature destruction of RBCs and RBC progenitors, which results in anemia, transfusion-dependence, iron overload, organ failure, and early death.

In sickle cell disease (SCD), one amino acid substitution in the beta globin chain results in the generation of sickling hemoglobin (HbS), which allows polymerization with repeated cycles of deoxygenation resulting in "sickling" of RBCs. The sickled RBCs undergo hemolysis, while adhesive sickled RBCs occlude the microcirculation, provoking widespread tissue ischemia and organ infarction. The natural history of SCD is marked by painful crises, acute chest syndrome, and eventual potentially life-threatening sequelae, including renal insufficiency, retinitis, osteonecrosis, osteomyelitis, aplastic crises, functional asplenism, stroke, priapism, and severe pulmonary hypertension.

The disclosure herein provides novel methods and compositions for modulating expression of target genes such as increasing expression of fetal hemoglobin in a patient with a blood disorder, including beta thalassemias and sickle cell disease.

SUMMARY

The present disclosure provides methods and compositions for modulating expression of a target gene in a cell by reducing binding of an endogenous transcription factor to a regulatory sequence of the target gene. The method includes introducing into the cell a DNA binding polypeptide (DBP) that binds a sequence in regulatory region of a target gene bound by a transcription factor (TF), thereby displacing the TF and modulating expression of the target gene. The DBP may be designed to bind a sequence comprising the binding site for the TF and additional nucleotides present on one or both sides of the sequence. Accordingly, the DBP specifically binds to binding site for the TF in the target gene but not in other genes that are also regulated by binding of the TF but do not include the nucleotides present on one or both sides of the sequence.

In certain aspects, the binding site for the TF is a sequence that has previously been identified as being associated with activity of the TF based on reduced activity of the TF when the sequence includes a single nucleotide polymorphism (SNP) or a mutation that may reduce binding of the TF.

In certain aspects, the DBP includes a plurality of RUs that are arranged from N-terminus to C-terminus to bind to a sequence bound by a TF and additional nucleotides present on one or both sides of the sequence.

In certain aspects, a recombinant DBP that includes a plurality of RUs that are arranged from N-terminus to C-terminus to bind to a sequence bound by the TF, ZBTB7A in the fetal γ-globin gene promoter is provided. In certain aspects, the RUs may be derived from a TALE protein and the DBP may include at least 9.5 RUs, which include 9 RUs and a terminal half-repeat unit (0.5 RU). The DBP displaces ZBTB7A from the fetal γ-globin gene promoter and relieves suppression of the fetal γ-globin gene. In certain aspects, the DBP also decreases expression of adult hemoglobin B (HBB).

In certain aspects, a cell line comprising a stable expression of the recombinant DBP as provided herein is disclosed. The cell line may be produced by stable integration into the genome of the cells of a nucleic acid encoding the DBP. The cell line may be administered to a subject in need thereof.

BRIEF DESCRIPTION OF THE DRAWINGS

FIG. 1B. Relative expression of HBG compared to HBB in HUDEP-2 cells at 48 hours post-transfection of B1 with the FokI domain (B1), B1 with no effector domain (B1NF), GFP, or no mRNA. FIG. 1D. Relative expression of HBG compared to HBB in HUDEP-2 cells at 48 hours post-transfection of A11, B1, B5, B7, D2, D11, or E1 TALE mRNA with no effector domain measured by TaqMan qPCR. FIG. 1C. Immunofluorescent imaging of FLAG (FLAG IF) at 6, 24, or 48 hours post-transfection of no mRNA, AAVS1R TALEN, B1, B1NF, B7, B7NF, D11, D11NF (NF means no effector domain) Significance was assessed by t-test. * p<0.05,  p<0.01, * p<0.001.

FIG. 2A. Expression of HBG out of total globin (HBG+HBB) in clonal lines stably expressing the A11 (n=13) or B1 (n=11) TALE to various levels, or a cell line with mutations in the −200 and −120 region of the HBG promoter (H8-2). FIG. 2B. Expression of HBG out of total globin (HBG+HBB) in clonal cell lines generated in three independent transfections, sorts, and expansion experiments. FIG. 2C. Percent of A11, B1, or WT cells expressing HBG (% APC) when compared to WT control cells measured by Globin FACS compared to RNA expression of HBG out of total globin measured by TaqMan qPCR. FIG. 2D. FLAG IF of 5 most highly expressing A11 clones, WT or B1 clone and corresponding HBG out of total globin expression measured by TaqMan qPCR.

DETAILED DESCRIPTION

Figure 1A:
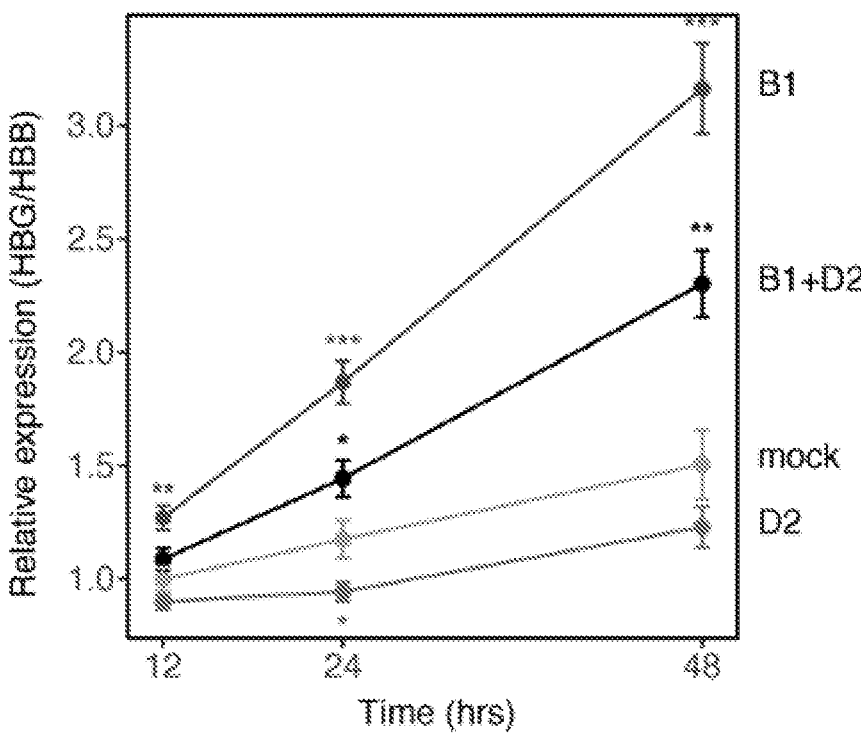
FIGS. 1A-1D. Transiently expressed TALEs with or without FokI activate HBG expression in a position-dependent manner FIG. 1A. Relative expression of HBG compared to HBB in HUDEP-2 cells at 12, 24, or 48 hours post-transfection of B1, D2, B1+D2 TALE with the FokI domain mRNA, or no mRNA (mock).

The present disclosure provides methods and compositions for modulating expression of a target gene in a cell by reducing binding of an endogenous transcription factor to a regulatory sequence of the target gene. The method includes introducing into the cell a DNA binding polypeptide (DBP) that binds a sequence in regulatory region of a target gene bound by a transcription factor (TF), thereby displacing the TF and modulating expression of the target gene. The DBP may be designed to bind a sequence comprising the binding site for the TF and additional nucleotides present on one or both sides of the sequence. Accordingly, the DBP specifically binds to binding site for the TF in the target gene but not in other genes that are also regulated by binding of the TF but do not include the nucleotides present on one or both sides of the sequence.

In certain aspects, the binding site for the TF is a sequence that has previously been identified as being associated with activity of the TF based on reduced activity of the TF when the sequence includes a single nucleotide polymorphism (SNP) or a mutation that may reduce binding of the TF.

In certain aspects, the DBP includes a plurality of RUs that are arranged from N-terminus to C-terminus to bind to a sequence bound by a TF and additional nucleotides present on one or both sides of the sequence.

In certain aspects, a recombinant DBP that includes a plurality of RUs that are arranged from N-terminus to C-terminus to bind to a sequence bound by the TF, ZBTB7A in the fetal γ-globin gene promoter is provided. In certain aspects, the RUs may be derived from a TALE protein and the DBP may include at least 9.5 RUs, which include 9 RUs and a terminal half-repeat unit (0.5 RU). The DBP displaces ZBTB7A from the fetal γ-globin gene promoter and relieves suppression of the fetal γ-globin gene. In certain aspects, the DBP also decreases expression of adult hemoglobin B (HBB).

In certain aspects, a cell line comprising a stable expression of the recombinant DBP as provided herein is disclosed. The cell line may be produced by stable integration into the genome of the cells of a nucleic acid encoding the DBP. The cell line may be administered to a subject in need thereof.

Before exemplary aspects of the present invention are described, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a protein" includes a plurality of such proteins and reference to "the polynucleotide" includes reference to one or more polynucleotides, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Definitions

As used herein, the term "derived" in the context of a polypeptide refers to a polypeptide that has a sequence that is based on that of a protein from a particular source (e.g., an animal pathogen such as *Legionella* or a plant pathogen such as *Xanthomonas*). A polypeptide derived from a protein from a particular source may be a variant of the protein from the particular source (e.g., an animal pathogen such as *Legionella* or a plant pathogen such as *Xanthomonas*). For example, a polypeptide derived from a protein from a particular source may have a sequence that is modified with respect to the protein's sequence from which it is derived. A polypeptide derived from a protein from a particular source shares at least 30% sequence identity with, at least 40% sequence identity with, at least 50% sequence identity with, at least 60% sequence identity with, at least 70% sequence identity with, at least 80% sequence identity with, or at least 90% sequence identity with the protein from which it is derived.

The DBP disclosed herein may be derived from a nucleic acid binding domain of a DNA binding protein of an animal or plant pathogen. The term "modular" as used herein in the context of a nucleic acid binding domain, e.g., a modular animal pathogen derived DNA binding polypeptide (MAP-DBP) indicates that the plurality of repeat units present in the DBP can be rearranged and/or replaced with other repeat units and can be arranged in an order such that the DBP binds to the target nucleic acid. For example, any repeat unit in a modular nucleic acid binding domain can be switched with a different repeat unit. In some aspects, modularity of the nucleic acid binding domains disclosed herein allows for switching the target nucleic acid base for a particular repeat unit by simply switching it out for another repeat unit. In some aspects, modularity of the nucleic acid binding domains disclosed herein allows for swapping out a particular repeat unit for another repeat unit to increase the affinity of the repeat unit for a particular target nucleic acid. Overall, the modular nature of the nucleic acid binding domains disclosed herein enables the development of DBP that can precisely target any nucleic acid sequence of interest.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like. In specific aspects, the terms refer to a polymeric form of amino acids of any length which include genetically coded amino acids. In particular aspects, the terms refer to a polymeric form of amino acids of any length which include genetically coded amino acids fused to a heterologous amino acid sequence.

The term "heterologous" refers to two components that are defined by structures derived from different sources. For example, in the context of a polypeptide, a "heterologous" polypeptide may include operably linked amino acid sequences that are derived from different polypeptides (e.g., a NBD and a functional domain derived from different sources). Similarly, in the context of a polynucleotide encoding a chimeric polypeptide, a "heterologous" polynucleotide may include operably linked nucleic acid sequences that can be derived from different genes. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) may be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein, the term "cleavage" refers to the breakage of the covalent backbone of a nucleic acid, e.g., a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain aspects, the polypeptides provided herein are used for targeted double-stranded DNA cleavage.

A "cleavage half-domain" is a polypeptide sequence which, in conjunction with a second polypeptide (either identical or different) forms a complex having cleavage activity (preferably double-strand cleavage activity).

A "target nucleic acid," "target sequence," or "target site" is a nucleic acid sequence that defines a portion of a nucleic acid to which a binding molecule, such as, the DBP disclosed herein will bind. The target nucleic acid may be present in inside a cell. A target nucleic acid may be present in a regulatory region, e.g., promoter sequence, of a target gene whose expression is to be modulated by the DBP.

An "exogenous" molecule is a molecule that is not normally present in a cell but can be introduced into a cell by one or more genetic, biochemical or other methods. An exogenous molecule can comprise, for example, a functioning version of a malfunctioning endogenous molecule, e.g. a gene or a gene segment lacking a mutation present in the endogenous gene. An exogenous nucleic acid can be present in an infecting viral genome, a plasmid or episome introduced into a cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control region.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA, shRNA, RNAi, miRNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristylation, and glycosylation.

"Modulation" of gene expression refers to a change in the activity of a gene. Modulation of expression can include, but is not limited to, gene activation and gene repression. Genome editing (e.g., cleavage, alteration, inactivation, donor integration, random mutation) can be used to modulate expression. Gene inactivation refers to any reduction in gene expression as compared to a cell that does not include a polypeptide or has not been modified by a polypeptide as described herein. Thus, gene inactivation may be partial or complete.

The terms "patient" or "subject" are used interchangeably to refer to a human or a non-human animal (e.g., a mammal).

The terms "treat", "treating", treatment" and the like refer to a course of action (such as administering a polypeptide or a nucleic acid encoding the polypeptide or a cell comprising the nucleic acid encoding the polypeptide or expressing the polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject.

The terms "prevent", "preventing", "prevention" and the like refer to a course of action (such as administering a polypeptide or a nucleic acid encoding the polypeptide or a cell comprising the nucleic acid encoding the polypeptide or expressing the polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects.

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. The association can be, for example, via a direct or indirect (e.g., via a linker) covalent linkage or via non-covalent interactions. In some aspects, the association is covalent. In some aspects, two molecules are conjugated via a linker connecting both molecules. For example, in some aspects where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein. Such conjugated proteins may be expressed as a fusion protein.

The term "consensus sequence," as used herein in the context of nucleic acid or amino acid sequences, refers to a sequence representing the most frequent nucleotide/amino acid residues found at each position in a plurality of similar sequences. Typically, a consensus sequence is determined by sequence alignment in which similar sequences are compared to each other. A consensus sequence of a protein can provide guidance as to which residues can be substituted without significantly affecting the function of the protein.

As used herein, the term "genome modifying proteins" refer to nucleic acid binding domains and functional domains which cooperate to modify genome or epigenome is a cell. Examples of genome modifying proteins are provided herein and include but are not limited to nucleic acid binding proteins comprising modular repeat units, nucleic acid binding proteins comprising zinc fingers, functional domains such as labels, tags, polypeptides having nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, e.g., nucleases, transcriptional activators, transcriptional repressors, chromatin modifying protein, and the like. Genome modifying proteins also encompass a single polypeptide comprising a nucleic acid binding domain and functional domain or two or more polypeptides, where a first polypeptide comprises a nucleic acid binding domain and a second polypeptide comprises a functional domain and wherein the first and second polypeptide associate with each other via a non-covalent interaction, such as, via a interactions mediated by first and second members of a heterodimer, where one of the first and second polypeptide is conjugated to the first member and the other polypeptide is conjugated to the second member.

As used herein, a "fusion protein" includes a first protein moiety, e.g., a nucleic acid binding domain, having a peptide linkage with a second protein moiety. In certain aspects, the fusion protein is encoded by a single fusion gene.

"Domain" is used to describe a segment of a protein or nucleic acid. Unless otherwise indicated, a domain is not required to have any specific functional property.

As used herein, the term "gene therapy" refers to the introduction of extra genetic material into the total genetic material in a cell that restores, corrects, or modifies expression of a gene or gene product, or for the purpose of expressing a therapeutic polypeptide. In particular aspects, introduction of genetic material into the cell's genome for the purpose of expressing a therapeutic polypeptide is considered gene therapy.

Methods

The present disclosure provides a method for modulating expression of a target gene in a cell, the method comprising introducing into the cell a DNA binding polypeptide (DBP) that binds a sequence in regulatory region of a gene bound by a transcription factor (TF), thereby displacing the TF and modulating expression of the gene.

In certain aspects, the sequence include a binding site for a TF that has also previously been identified as being associated with activity of the TF based on reduced activity of the TF when the binding site includes or is adjacent to a single nucleotide polymorphism (SNP) or a mutation. In certain aspects, the binding site may include or is adjacent to SNPs or mutations that lead to an increased expression of the protein encoded by the gene, which may be indicative of reduced binding of a TF, such as a transcriptional repressor, to the binding site. In certain aspects, the binding site may include or is adjacent to SNPs or mutations that lead to a decreased expression of the protein encoded by the gene, which may be indicative of reduced binding of a TF, such as a transcriptional activator, to the binding site. In certain aspects, it may be desirable to displace the TF from the binding site in the regulatory region of a target gene. In certain aspects, the method for modulating expression of the target gene in a cell includes introducing into the cell a DBP that binds to the binding site and additional nucleotides present adjacent the binding site, e.g., nucleotides flanking the binding site.

The mutation in or adjacent the binding site may be a deletion, insertion, or substitution. As used herein, the term binding site refers to a core sequence that is required for binding of a TF to the regulatory region of a gene and modulate gene expression. A binding site is usually less than 10 nucleotides in length and more commonly 4-8 nucleotides in length. A TF may bind to more than one binding site in the regulatory region of a gene. As noted herein, the DBP may bind to a binding site as well as nucleotides adjacent the binding site to increase the binding specificity of the DBP such that it binds to the binding site for the TF for a target gene but not to other genes that also including a binding site for the TF but include different nucleotide sequences adjacent the binding site.

In certain aspects, the DBP may bind to at least a 12 nucleotides long sequence comprising the sequence bound by the TF. In certain aspects, the DBP may bind to at least a 14, 16, 18, 20, 24, 26, 28, 30, or up to 45 nucleotides long sequence comprising the sequence bound by the TF. In certain aspects, the DBP may bind to the a binding site for a transcriptional activator and the introducing results in reduced expression of the gene. In certain aspects, the DBP may bind to the a binding site for a transcriptional repressor and the introducing results in increased expression of the gene.

In certain aspects, the DBP is introduced into the cell as a nucleic acid encoding the DBP. The nucleic acid may be a deoxyribonucleic acid (DNA) or a ribonucleic acid (RNA).

In certain aspects, the sequence of the nucleic acid is codon optimized for expression in a human cell. Methods and compositions for introducing a nucleic acid into a cell are described in detail in subsequent sections of this disclosure. In certain aspects, the cell is a human cell, such as, a cancer cell, an ex vivo cell obtained from a subject, a stem cell, a hematopoietic stem cell, or the like. Cells and cell lines containing a target gene are described in detail in subsequent sections of this disclosure. In certain aspects, the target gene may fetal hemoglobin gamma.

In certain aspects, introducing the DBP into a cell may include administering the polypeptide or a nucleic acid encoding the polypeptide to a subject in need thereof.

Proteins

The DBPs of the present disclosure include modular units that mediate binding to a nucleotide sequence in the regulatory region of a target gene in a cell. The modular units may be derived from DNA binding domains of proteins known to specifically bind to a nucleotide sequence. Such modular units include zing fingers, megaTAL, repeat units from TALE protein, repeat units from DNA binding proteins from animal pathogens, and the like.

In certain aspects, the DBP may bind to the binding sequence of the TF, ZBTB7A in the promoter region of the fetal γ-globin gene and displace the TF from this binding site. The DBP may bind to sequences adjacent the binding site. In certain aspects, the DBP may bind to the sequence CCTCTTGGGGGCCCC (SEQ ID NO: 1) in the promoter region of the fetal γ-globin gene and displace ZBTB7A and increase expression of the fetal γ-globin gene. In certain aspects, the DBP may bind to the sequence ATCCTCTTGGGGGCCCC (SEQ ID NO: 2) in the promoter region of the fetal γ-globin gene and displace ZBTB7A and increase expression of the fetal γ-globin gene. In certain aspects, the DBP may bind to the sequence CCTCTTGGGGGCCCCTTCCC (SEQ ID NO: 3) in the promoter region of the fetal γ-globin gene and displace ZBTB7A and increase expression of the fetal γ-globin gene.

TALE Derived DBP

The DBP includes at least ten repeat units (RUs) ordered from N-terminus to C-terminus of the DBP to specifically bind to sequence bound by a TF as disclosed herein, wherein each of the RUs comprises the sequence:

$X_{1-11}X_{12}X_{13}X_{14-33,34, \text{ or } 35}$ (SEQ ID NO: 4), wherein:

$X_{1-11}$ is a chain of 11 contiguous amino acids, $X_{14-33 \text{ or } 34 \text{ or } 35}$ is a chain of 20, 21 or 22 contiguous amino acids, $X_{12}X_{13}$ is selected from:

(a) NH, HH, KH, NK, NQ, RH, RN, SS, NN, SN, or KN for recognition of guanine (G);

(b) NI, KI, RI, HI, or SI for recognition of adenine (A);

(c) NG, HG, KG, or RG for recognition of thymine (T);

(d) HD, RD, SD, ND, KD, or YG for recognition of cytosine (C); and (e) NV or HN for recognition of A or G; and (f) H*, HA, KA, N*, NA, NC, NS, RA, or S* for recognition of A or T or G or C, wherein (*) means that the amino acid at $X_{13}$ is absent, wherein the DBP displaces the TF from the regulatory region (e.g. promoter or enhancer region) of a target gene and modulates expression of the target gene.

In certain aspects, the DBP includes a half-repeat unit (0.5 RU) as the last RU such that the DBP includes at least 10.5 RUs. A half-repeat unit may have the amino acid sequence $X_{1-11}X_{12}X_{13}X_{14-19, 20, \text{ or } 21}$ (SEQ ID NO: 5), wherein:

$X_{1-11}$ is a chain of 11 contiguous amino acids, $X_{14-20 \text{ or } 21 \text{ or } 22}$ is a chain of 7, 8 or 9 contiguous amino acids, $X_{12}X_{13}$ is selected from:

(a) NH, HH, KH, NK, NQ, RH, RN, SS, NN, SN, or KN for recognition of guanine (G);

(b) NI, KI, RI, HI, or SI for recognition of adenine (A);

(c) NG, HG, KG, or RG for recognition of thymine (T);

(d) HD, RD, SD, ND, KD, or YG for recognition of cytosine (C); and (e) NV or HN for recognition of A or G; and (f) H*, HA, KA, N*, NA, NC, NS, RA, or S* for recognition of A or T or G or C, wherein (*) means that the amino acid at $X_{13}$ is absent.

In certain aspects, $X_{1-11}$ is at least 80% identical, at least 90% identical, or 100% identical to LTPEQVVAIAS (SEQ ID NO: 6). In certain aspects, $X_{14-20\ or\ 21\ or\ 22}$ is at least 80% identical to GGRPALE (SEQ ID NO: 7).

The present disclosure provides a DBP that includes a plurality of repeat units (RUs) comprising a 33-36 amino acid long sequence having at least 80% sequence identity to the amino acid sequence:

LTPDQVVAIASX$^{12}$X$^{13}$GGKQALETVQRLLPVL QDHG (SEQ ID NO: 8), or having the sequence of SEQ ID NO:1 with one or more conservative amino acid substitutions thereto; wherein $X_{12}X_{13}$ is HH, KH, NH, NK, NQ, RH, RN, SS, NN, SN, KN, NI, KI, RI, HI, SI, NG, HG, KG, RG, RD, SD, HD, ND, KD, YG, YK, NV, HN, H*, HA, KA, N*, NA, NC, NS, RA, CI, or S*, where (*) means $X_{13}$ is absent In certain aspects, the RU may comprise a 33-36 amino acid long sequence having a sequence at least 85%, at least 90%, at least 91%, at least 92%, at least 93%, at least 94%, at least 95%, or more identical to SEQ ID NO: 8.

In certain aspects, the RUs and the half-RU, if present, are derived from *Xanthomonas* TALE. In certain aspects, $X_{1-11}$ is at least 80%, at least 90%, or 100% identical to LTPEQVVAIAS (SEQ ID NO: 6), LTPAQVVAIAS (SEQ ID NO: 9), LTPDQVVAIAN (SEQ ID NO: 10), LTPDQVVAIAS (SEQ ID NO: 11), LTPYQVVAIAS (SEQ ID NO: 12), LTREQVVAIAS (SEQ ID NO: 13), or LSTAQVVAIAS (SEQ ID NO: 14). In certain aspects, $X_{14-20\ or\ 21\ or\ 22}$ is at least 80%, at least 90%, at least 95%, or 100% identical to GGKQALETVQRLLPVLCQDHG (SEQ ID NO: 15), GGKQALATVQRLLPVLCQDHG (SEQ ID NO: 16), GGKQALETVQRVLPVLCQDHG (SEQ ID NO: 17), or GGKQALETVQRVLPVLCQDHG (SEQ ID NO: 17).

In certain aspects, the DBP may include a plurality of RUs ordered from N-terminus to C-terminus of the DBP to bind a nucleic acid sequence comprising the binding site for a TF in the regulatory region of a target gene. For example, the DBP may include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 RUs, where at least one of the RUs is a RU as disclosed herein. In certain aspects, the DBP may include a plurality of RUs of naturally occurring transcription activator like effector (TALE) proteins, such as RUs from *Xanthomonas* or *Ralstonia* TALE proteins.

In certain aspects, one or more RUs in a DBP may be at least 80%, 85%, 90%, 91%, 92%, 93%, 94%, 95%, 96%, 97%, 98%, or 99%, or a 100% identical to a RU provided herein. Percent identity between a pair of sequences may be calculated by multiplying the number of matches in the pair by 100 and dividing by the length of the aligned region, including gaps. Identity scoring only counts perfect matches and does not consider the degree of similarity of amino acids to one another. Only internal gaps are included in the length, not gaps at the sequence ends.

Percent Identity=(Matches×100)/Length of aligned region (with gaps)

The phrase "conservative amino acid substitution" refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain.

Guidance for substitutions, insertions, or deletions may be based on alignments of amino acid sequences of proteins from different species or from a consensus sequence based on a plurality of proteins having the same or similar function.

In certain aspects, the disclosed DBP may include a nuclear localization sequence (NLS) to facilitate entry into an organelle of a cell, e.g. the nucleus of a cell, e.g., an animal or a plant cell. In certain aspects, the disclosed DBP may include a half-RU or a partial RU that is 15-20 amino acid long sequence. Such a half-RU may be included after the last RU present in the DBP and may be derived from a RU identified in *Xanthomonas* or *Ralstonia* TALE protein. In certain aspects, the disclosed DBP may include an N-terminal domain. The N-terminal domain may be the N-cap domain or a fragment thereof from TALE proteins like those expressed in *Burkholderia*, Paraburkholderia, or *Xanthomonas*. In certain aspects, the disclosed DBP may include a C-terminal domain. The C-terminal domain may be a C-cap domain or a fragment thereof from TALE proteins like those expressed in *Burkholderia*, Paraburkholderia, or *Xanthomonas*.

In certain aspects, the N-terminal domain may be at least 80%, 85%, 90%, 91%, 92%, 93%, 94%, 95%, 96%, 97%, 98%, or 99%, or a 100% identical to the N-terminus region sequence provided in Table 2. This amino acid sequence includes a M added to the N-terminus which is not present in the wild type N-cap region of a *Xanthomonas* TALE protein. This amino acid sequence is generated by deleting amino acids N+288 through N+137 of the N-terminus region of a TALE protein, adding a M, such that amino acids N+136 through N+1 of the N-terminus region of the TALE protein are present.

In some aspects, the N-terminus can be truncated such that the fragment of the N-terminus includes amino acids from position 1 (N) through position 120 (K) of the naturally occurring *Xanthomonas* spp.-derived protein as follows:

```
                                          (SEQ ID NO: 18)
KPKVRSTVAQHHEALVGHGFTHAHIVALSQHPAALGTVAVKYQDMIAAL

PEATHEAIVGVGKQWSGARALEALLTVAGELRGPPLQLDTGQLLKIAKR

GGVTAVEAVHAWRNALTGAPLN.
```

In some aspects, the N-cap region can be truncated such that the fragment of the N-terminus includes amino acids from position 1 (N) through position 115 (S) of the naturally occurring *Xanthomonas* spp.-derived protein as follows:

```
                                          (SEQ ID NO: 19)
STVAQHHEALVGHGFTHAHIVALSQHPAALGTVAVKYQDMIAALPEATH

EAIVGVGKQWSGARALEALLTVAGELRGPPLQLDTGQLLKIAKRGGVTA

VEAVHAWRNALTGAPLN.
```

In some aspects, the N-cap region can be truncated and may include amino acids from position 1 (N) through position 110 (H) of the naturally occurring *Xanthomonas* spp.-derived protein as follows:

(SEQ ID NO: 20)
HHEALVGHGFTHAHIVALSQHPAALGTVAVKYQDMIAALPEATHEAIVG

VGKQWSGARALEALLTVAGELRGPPLQLDTGQLLKIAKRGGVTAVEAVH

AWRNALTGAPLN.

In certain aspects, the DBP may include a C-cap region at C-terminus of the recombinant polypeptide which C-cap region is derived from the C-cap region of a *Xanthomonas* TALE protein. In certain aspects, the C-cap region at the C-terminus which may be present immediately adjacent the last RU or the last half-RU, if present. In certain aspects, the C-cap region at the C-terminus which may be linked to the last RU or the last half-RU, if present, via a linker.

In certain aspects, the C-terminal domain may be at least 80%, 85%, 90%, 91%, 92%, 93%, 94%, 95%, 96%, 97%, 98%, or 99%, or a 100% identical to the C-terminus region sequence provided in Table 2.

In certain aspects, the RUs are derived from *Xanthomonas* TALEs. In plant genomes, such as *Xanthomonas*, the natural TALE-binding sites begin with a thymine (T), which may be specified by a cryptic signal within the non-repetitive N-terminus region of the TALE polypeptide; in some cases this region may be referred to as repeat 0. In animal genomes, TALE binding sites do not necessarily have to begin with a thymine (T) and recombinant DBP disclosed herein may target DNA sequences that begin with T, A, G or C. In certain aspects, the recombinant DBP disclosed herein may target DNA sequences that begin with T. The tandem repeat of TALE RUs ends with a half-length repeat or a stretch of sequence that may share identity with only the first 20 amino acids of a repetitive full length TALE RU and this half repeat may be referred to as a half-monomer, a half RU, or a half repeat. Therefore, it follows that the length of the DNA sequence being targeted by DBP derived from TALEs is equal to the number of full RUs plus two. Thus, for example, DBP may be engineered to include X number (e.g., 9, 10, 11, 12, 13, 14, 15, 16, 17, 18, 19, 20, 21, 22, 23, 24, 25, or 26) full length RUs that are specifically ordered or arranged to target nucleic acid sequences of X+2 length (e.g., 11, 12, 13, 14, 15, 16, 17, 18, 19, 20, 21, 22, 23, 24, 25, 26, 27, or 28 nucleotides, respectively), with the N-terminus region binding "T" and the last RU being a half-repeat.

In certain aspects, a *Xanthomonas* spp.-derived repeat units can have a sequence of LTPDQVVA-IASNHGGKQALETVQRLLPVLCQDHG (SEQ ID NO: 21) comprising an RVD of NH, which recognizes guanine. A *Xanthomonas* spp.-derived repeat units can have a sequence of LTPDQVVA-IASNGGGKQALETVQRLLPVLCQDHG (SEQ ID NO: 22) comprising an RVD of NG, which recognizes thymidine. A *Xanthomonas* spp.-derived repeat units can have a sequence of LTPDQVVA-IASNIGGKQALETVQRLLPVLCQDHG (SEQ ID NO: 23) comprising an RVD of NI, which recognizes adenosine. A *Xanthomonas* spp.-derived repeat units can have a sequence of LTPDQVVA-IASHDGGKQALETVQRLLPVLCQDHG (SEQ ID NO: 24) comprising an RVD of HD, which recognizes cytosine.

In certain aspects, the DBP comprises RUs that binds to the nucleotide sequence: CCTCTTGGGGGCCC (SEQ ID NO: 1) in the regulatory region of the fetal □-globin gene and induces expression of HBG. In certain aspects, $X_{12}X_{13}$ in the RUs from N-terminus to C-terminus are HD, HD, NG, HD, NG, NG, NH, NH, NH, NH, NH, HD, HD, HD, and HD, wherein the last RU is a half-RU.

In certain aspects, the DBP comprises RUs that binds to the nucleotide sequence: ATCCTCTTGGGGGCCCC (SEQ ID NO: 2) in the regulatory region of the fetal □-globin gene and induces expression of HBG. In certain aspects, $X_{12}X_{13}$ in the RUs from N-terminus to C-terminus are NI, NG, HD, HD, NG, HD, NG, NG, NH, NH, NH, NH, NH, HD, and HD, wherein the last RU is a half-RU.

In certain aspects, the DBP comprises RUs that binds to the nucleotide sequence: CCTCTTGGGGGCCCCTTCCC (SEQ ID NO: 3) in the regulatory region of the fetal □-globin gene and induces expression of HBG. In certain aspects, $X_{12}X_{13}$ in the RUs from N-terminus to C-terminus are HD, HD, NG, HD, NG, NG, NH, NH, NH, NH, NH, HD, HD, HD, HD, NG, NG, HD, HD, and HD, wherein the last RU is a half-RU.

In some aspects, expression of the target gene can be reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 92%, at least 95%, at least 97%, or at least 99% by using a DNA binding polypeptide that displaces a transcriptional activator as compared to untreated cells.

In some aspects, expression of the target gene can be increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 92%, at least 95%, at least 97%, or at least 99% by using a DNA binding polypeptide that displaces a transcriptional repressor as compared to untreated cells.

In some aspects, modulation of gene expression (e.g., repression or activation of the target gene) by a DNA binding polypeptide that displaces a transcriptional factor can last for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, 1 day to 3 days, 3 days to 5 days, 5 days to 7 days, 7 days to 9 days, 9 days to 11 days, 11 days to 13 days, 13 days to 15 days, 15 days to 17 days, 17 days to 19 days, 19 days to 21 days, 21 days to 23 days, 23 days to 25 days, or 25 days to 28 days.

DBP Derived from *Ralstonia*

In certain aspects, the RUs and one or both N-Cap and C-Cap regions may be derived from a transcription activator like effector-like protein (TALE-like protein) of *Ralstonia solanacearum*. Repeat units derived from *Ralstonia solanacearum* can be 33-35 amino acid residues in length. In some aspects, the repeat can be derived from the naturally occurring *Ralstonia solanacearum* TALE-like protein.

As noted herein, the RUs may have the sequence $X_{1-11}$ $X_{12}X_{13}X_{14-33,\,34,\,or\,35}$ (SEQ ID NO: 25), where $X_{1-11}$ is a chain of 11 contiguous amino acids, $X_{14-33\,or\,34\,or\,35}$ is a chain of 20, 21 or 22 contiguous amino acids, $X_{12}X_{13}$ is RVD and is selected from: (a) NH, HH, KH, NK, NQ, RH, RN, SS, NN, SN, or KN for recognition of guanine (G); (b) NI, KI, RI, HI, or SI for recognition of adenine (A); (c) NG, HG, KG, or RG for recognition of thymine (T); (d) HD, RD, SD, ND, KD, or YG for recognition of cytosine (C); and (e) NV or HN for recognition of A or G; and (f) H*, HA, KA, N*, NA, NC, NS, RA, or S*for recognition of A or T or G or C, wherein (*) means that the amino acid at $X_{13}$ is absent. In certain aspects, $X_1$-11 may include a stretch of amino acids at least 80%, at least 90%, or a 100% identical to the $X_1$-11 residues of the following RUs from *Ralstonia*. In certain aspects, $X_{14-33\ or\ 34\ or\ 35}$ may include a stretch of 20, 21, or 22 amino acids at least 80%, at least 90%, or a 100% identical to the $X_{14-33\ or\ 34\ or\ 35}$ residues of the following RUs from *Ralstonia*: LDTEQVVA-IASHNGGKQALEAVKADLLDLLGAPYV (SEQ ID NO: 26), LNTEQVVAVASNKGGKQALEAVGAQLLAL-RAVPYE (SEQ ID NO: 27), LSTAQVAA-IASHDGGKQALEAVGTQLVVLRAAPYA (SEQ ID NO: 28), LSTAQVVAVAGRNGGKQALEAVRAQLPAL-RAAPYG (SEQ ID NO: 29), or LSTAQVVA-VASSNGGKQALEAVWALLPVLRATPYD (SEQ ID NO: 30).

In certain aspects, a *Ralstonia solanacearum*-repeat unit can have at least 80% sequence identity with any one of the *Ralstonia* RUs provided herein.

In certain aspects, the DBP may include a N-cap region at the N-terminus which may be present immediately adjacent the first RU or may be linked to the first RU via a linker. In some aspects, an DBP of the present disclosure can have the full length naturally occurring N-terminus of a naturally occurring *Ralstonia solanacearum*-derived protein. In some aspects, any truncation of the full length naturally occurring N-terminus of a naturally occurring *Ralstonia solanacearum*-derived protein can be used at the N-terminus of a DBP of the present disclosure. For example, in some aspects, amino acid residues at positions 1 (H) to position 137 (F) of the naturally occurring *Ralstonia solanacearum*-derived protein N-terminus can be used as the N-cap region. In particular aspects, the truncated N-terminus from position 1 (H) to position 137 (F) can have a sequence as follows: FGKLVALGYSREQIRKLKQESLSEIAKYHT-TLTGQGFTHADICRISRRRQSLRVVARNYP ELAAALPELTRAHIVDIARQRSGDLALQALLPVATAL-TAAPLRLSASQIATVAQYGERP AIQALYRLRRKL-TRAPLH (SEQ ID NO: 31). In some aspects, the naturally occurring N-terminus of *Ralstonia solanacearum* can be truncated to any length and used as the N-cap of the engineered DNA binding polypeptide. For example, the naturally occurring N-terminus of *Ralstonia solanacearum* can be truncated to include amino acid residues at position 1 (H) to position 120 (K) as follows: KQESLSEIAKYHT-TLTGQGFTHADICRISRRRQSLRVVARNYPE-LAAALPELTRAHIVDI ARQRS GDLALQALLPVATAL-TAAPLRLSASQIATVAQYGERPAIQALYRLRRKLTRAPL H (SEQ ID NO: 32) and used as the N-cap of the DBP. The naturally occurring N-terminus of *Ralstonia solanacearum* can be truncated amino acid residues to include positions 1 to 115 and used at the N-cap of the engineered DNA binding domain. The naturally occurring N-terminus of *Ralstonia solanacearum* can be truncated to amino acid residues at positions 1 to 50, 1 to 70, 1 to 100, 1 to 120, 1 to 130, 10 to 40, 60 to 100, or 100 to 120 and used as the N-cap of the engineered DNA binding domain. As noted for N-cap region derived from *Xanthomonas* TALE, the amino acid residues are numbered backward from the first repeat unit such that the amino acid (H in this case) of the N-cap adjacent the first RU is numbered 1 while the N-terminal amino acid of the N-cap is numbered 137 (and is F in this case) or 120 (and is K in this case).

In some aspects, the N-cap, referred to as the amino terminus or the "NH2" domain, can recognize a guanine. In some aspects, the N-cap can be engineered to bind a cytosine, adenosine, thymidine, guanine, or uracil.

In some aspects, an DBP of the present disclosure can include a plurality of RUs followed by a final single half-repeat also derived from *Ralstonia solanacearum*. The half repeat can have 15 to 23 amino acid residues, for example, the half repeat can have 19 amino acid residues. In particular aspects, the half-repeat can have a sequence as follows:

```
                                    (SEQ ID NO: 33)
            LSTAQVVAIACISGQQALE.
```

In some aspects, an DBP of the present disclosure can have the full length naturally occurring C-terminus of a naturally occurring *Ralstonia solanacearum*-derived protein as a C-cap region that is conjugated to the last RU. In some aspects, any truncation of the full length naturally occurring C-terminus of a naturally occurring *Ralstonia solanacearum*-derived protein can be used as the C-cap. For example, in some aspects, the DBP can comprise amino acid residues at position 1 (A) to position 63 (S) as follows: AIEAHMPTLRQASHSLSPERVAAIACIGGR-SAVEAVRQGLPVKAIRRIRREKAPVAGPPP AS (SEQ ID NO: 34) of the naturally occurring *Ralstonia solanacearum*-derived protein C-terminus. In some aspects, the naturally occurring C-terminus of *Ralstonia solanacearum* can be truncated to any length and used as the C-cap of the DBP. For example, the naturally occurring C-terminus of *Ralstonia solanacearum* can be truncated to amino acid residues at positions 1 to 63 and used as the C-terminus of the DBP. The naturally occurring C-terminus of *Ralstonia solanacearum* can be truncated amino acid residues at positions 1 to 50 and used as the C-cap of the DBP. The naturally occurring C-terminus of *Ralstonia solanacearum* can be truncated to amino acid residues at positions 1 to 63, 1 to 50, 1 to 70, 1 to 100, 1 to 120, 1 to 130, 10 to 40, 60 to 100, or 100 to 120 and used as the C-cap of the DBP. Exemplary sequences of domains of a DBP as disclosed herein are as follows:

| Description | Sequence |
| --- | --- |
| Truncated N-terminus; positions 1 (H) to 115 (S) of the naturally occurring *Ralstonia solanacearum*-derived protein N-terminus | SEIAKYHTTLTGQGFTHADICRISRRRQSLRVVARNYPELAAALP ELTRAHIVDIARQRSGDLALQALLPVATALTAAPLRLSASQIATV AQYGERPAIQALYRLRRKLTRAPLH (SEQ ID NO: 35) |
| Truncated N-terminus; positions 1 (H) to 137 (F) of the naturally occurring *Ralstonia solanacearum*-derived protein N-terminus | FGKLVALGYSREQIRKLKQESLSEIAKYHTTLTGQGFTHADICRI SRRRQSLRVVARNYPELAAALPELTRAHIVDIARQRSGDLALQA LLPVATALTAAPLRLSASQIATVAQYGERPAIQALYRLRRKLTR APLH (SEQ ID NO: 31) |

-continued

| Description | Sequence |
|---|---|
| Truncated N-terminus; positions 1 (H) to 120 (K) of the naturally occurring *Ralstonia solanacearum*-derived protein N-terminus | KQESLSEIAKYHTTLTGQGFTHADICRISRRRQSLRVVARNYPEL AAALPELTRAHIVDIARQRSGDLALQALLPVATALTAAPLRLSAS QIATVAQYGERPAIQALYRLRRKLTRAPLH (SEQ ID NO: 32) |
| Half-repeat | LSTAQVVAIACISGQQALE (SEQ ID NO: 33) |
| Truncated C-terminus; positions 1 (A) to 63 (S) of the naturally occurring *Ralstonia solanacearum*-derived protein C-terminus | AIEAHMPTLRQASHSLSPERVAAIACIGGRSAVEAVRQGLPVKAI RRIRREKAPVAGPPPAS (SEQ ID NO: 34) |

DBP Derived from Animal Pathogens

In some aspects, the present disclosure provides DNA binding polypeptide in which the repeat units can be derived from a Legionellales bacterium, a species of the genus of *Legionella*, such as *L. quateirensis* or *L. maceachernii*, the genus of *Burkholderia*, the genus of Paraburkholderia, or the genus of *Francisella*.

As noted herein, the RUs may have the sequence $X_{1-11}X_{12}X_{13}X_{14-33, 34, \text{ or } 35}$ (SEQ ID NO: 36), where $X_{1-11}$ is a chain of 11 contiguous amino acids, $X_{14-33 \text{ or } 34 \text{ or } 35}$ is a chain of 20, 21 or 22 contiguous amino acids, $X_{12}X_{13}$ is selected from: (a) NH, HH, KH, NK, NQ, RH, RN, SS, NN, SN, HN, or KN for recognition of guanine (G); (b) NI, KI, RI, HI, HA, or SI for recognition of adenine (A); (c) NG, HG, KG, or RG for recognition of thymine (T); (d) HD, RD, SD, ND, KD, or YG for recognition of cytosine (C); and (e) NV or HN for recognition of A or G; and (f) H*, HA, KA, N*, NA, NC, NS, RA, or S*for recognition of A or T or G or C, wherein (*) means that the amino acid at $X_{13}$ is absent. In certain aspects, $X_1$-11 may include a stretch of amino acids at least 80%, at least 90%, or a 100% identical to the $X_1$-11 residues of the following RUs from animal pathogens, *Legionella, Burkholderia*, Paraburkholderia, or *Francisella*. In certain aspects, $X_{14-33, 34, \text{ or } 35}$ may include a stretch of 20, 21, or 22 amino acids at least 80%, at least 90%, or a 100% identical to the $X_{14-33, 34, \text{ or } 35}$ residues of the RUs from animal pathogens, *Legionella* (e.g., *L. quateirensis* or *L. maceachernii*), *Burkholderia*, Paraburkholderia, or *Francisella* listed below.

| Organism | Repeat Unit Sequence $(X_{1-11}X_{12}X_{13}X_{14-33, 34, \text{ or } 35})$ | SEQ ID | BCR $(X_{12}X_{13})$ |
|---|---|---|---|
| *L. quateirensis* | FSSQQIIRMVSHAGGANNLKAVTANHDDLQNMG | 37 | HA |
| *L. quateirensis* | FNVEQIVRMVSHNGGSKNLKAVTDNHDDLKNMG | 38 | HN |
| *L. quateirensis* | FNAEQIVRMVSHGGGSKNLKAVTDNHDDLKNMG | 39 | HG |
| *L. quateirensis* | FNAEQIVSMVSNNGGSKNLKAVTDNHDDLKNMG | 40 | NN |
| *L. quateirensis* | FNAEQIVSMVSNGGGSLNLKAVKKYHDALKDRG | 41 | NG |
| *L. quateirensis* | FNTEQIVRMVSHDGGSLNLKAVKKYHDALRERK | 42 | HD |
| *L. quateirensis* | FNVEQIVSIVSHGGGSLNLKAVKKYHDVLKDRE | 43 | HG |
| *L. quateirensis* | FNAEQIVRMVSHDGGSLNLKAVTDNHDDLKNMG | 44 | HD |
| *L. maceachernii* | FSAEQIVRIAAHDGGSRNIEAVQQAQHVLKELG | 45 | HD |
| *L. maceachernii* | FSAEQIVSIVAHDGGSRNIEAVQQAQHILKELG | 46 | HD |
| *Legionellales bacterium* | LDRQQILRIASHDGGSKNIAAVQKFLPKLMNFG | 47 | HD |
| *L. maceachernii* | FSAEQIVRIAAHDGGSLNIDAVQQAQQALKELG | 48 | HD |
| *L. maceachernii* | FSTEQIVCIAGHGGGSLNIKAVLLAQQALKDLG | 49 | HG |
| *L. maceachernii* | YSSEQIVRVAAHGGGSLNIKAVLQAHQALKELD | 50 | HG |
| *L. maceachernii* | FSAEQIVHIAAHGGGSLNIKAILQAHQTLKELN | 51 | HG |
| *L. maceachernii* | FSAEQIVRIAAHIGGSRNIEAIQQAHHALKELG | 52 | HI |
| *L. maceachernii* | FSAEQIVRIAAHIGGSHNLKAVLQAQQALKELD | 53 | HI |
| *L. maceachernii* | FSAKHIVRIAAHIGGSLNIKAVQQAQQALKELG | 54 | HI |
| *L. quateirensis* | FNAEQIVRMVSHKGGSKNLALVKEYFPVFSSFH | 55 | HK |

-continued

| Organism | Repeat Unit Sequence $(X_{1-11}X_{12}X_{13}X_{14-33, \ 34, \ or \ 35})$ | SEQ ID | BCR $(X_{12}X_{13})$ |
|---|---|---|---|
| *L. maceachernii* | FSADQIVRIAAHKGGSHNIVAVQQAQQALKELD | 56 | HK |
| *L. maceachernii* | FSAEQIVSIAAHVGGSHNIEAVQKAHQALKELD | 57 | HV |
| *Burkholderia* | FSSGETVGATVGAGGTETVAQGGTASNTTVSSG | 58 | GA |
| *Burkholderia* | FSGGMATSTTVGSGGTQDVLAGGAAVGGTVGTG | 59 | GS |
| *Burkholderia* | FSAADIVKIAGKIGGAQALQAFITHRAALIQAG | 60 | KI |
| *Burkholderia* | FNPTDIVKIAGNDGGAQALQAVLELEPALRERG | 61 | ND |
| *Burkholderia* | FNPTDIVRMAGNDGGAQALQAVFELEPAFRERS | 62 | ND |
| *Burkholderia* | FNPTDIVRMAGNDGGAQALQAVLELEPAFRERG | 63 | ND |
| *Burkholderia* | FSQVDIVKIASNDGGAQALYSVLDVEPTFRERG | 64 | ND |
| *Burkholderia* | FSRADIVKIAGNDGGAQALYSVLDVEPPLRERG | 65 | ND |
| *Burkholderia* | FSRGDIVKIAGNDGGAQALYSVLDVEPPLRERG | 66 | ND |
| *Burkholderia* | FNRADIVRIAGNGGGAQALYSVRDAGPTLGKRG | 67 | NG |
| *Burkholderia* | FRQADIVKIASNGGSAQALNAVIKLGPTLRQRG | 68 | NG |
| *Burkholderia* | FRQADIVKMASNGGSAQALNAVIKLGPTLRQRG | 69 | NG |
| *Burkholderia* | FSRADIVKIAGNGGGAQALQAVLELEPTFRERG | 70 | NG |
| *Burkholderia* | FSRADIVRIAGNGGGAQALYSVLDVGPTLGKRG | 71 | NG |
| *Burkholderia* | FSRGDIVRIAGNGGGAQALQAVLELEPTLGERG | 72 | NG |
| *Burkholderia* | FSRADIVKIAGNGGGAQALQAVITHRAALTQAG | 73 | NG |
| *Burkholderia* | FSRGDTVKIAGNIGGAQALQAVLELEPTLRERG | 74 | NI |
| *Burkholderia* | FNPTDIVKIAGNIGGAQALQAVLELEPAFRERG | 75 | NI |
| *Burkholderia* | FSAADIVKIAGNIGGAQALQAIFTHRAALIQAG | 76 | NI |
| *Burkholderia* | FSAADIVKIAGNIGGAQALQAVITHRATLTQAG | 77 | NI |
| *Burkholderia* | FSATDIVKIASNIGGAQALQAVISRRAALIQAG | 78 | NI |
| *Burkholderia* | FSQPDIVKIAGNIGGAQALQAVLELEPAFRERG | 79 | NI |
| *Burkholderia* | FSRADIVKIAGNIGGAQALQAVLELESTFRERS | 80 | NI |
| *Burkholderia* | FSRADIVKIAGNIGGAQALQAVLELESTLRERS | 81 | NI |
| *Burkholderia* | FSRGDIVKMAGNIGGAQALQAGLELEPAFRERG | 82 | NI |
| *Burkholderia* | FSRGDIVKMAGNIGGAQALQAVLELEPAFHERS | 83 | NI |
| *Burkholderia* | FTLTDIVKMAGNIGGAQALKAVLEHGPTLRQRD | 84 | NI |
| *Burkholderia* | FTLTDIVKMAGNIGGAQALKVVLEHGPTLRQRD | 85 | NI |
| *Burkholderia* | FNPTDIVKIAGNNGGAQALQAVLELEPALRERG | 86 | NN |
| *Burkholderia* | FNPTDIVKIAGNNGGAQALQAVLELEPALRERS | 87 | NN |
| *Burkholderia* | FNPTDMVKIAGNNGGAQALQAVLELEPALRERG | 88 | NN |
| *Burkholderia* | FSAADIVKIASNNGGAQALQALIDHWSTLSGKT | 89 | NN |
| *Burkholderia* | FSAADIVKIASNNGGAQALQAVISRRAALIQAG | 90 | NN |
| *Burkholderia* | FSAADIVKIASNNGGAQALQAVITHRAALAQAG | 91 | NN |
| *Burkholderia* | FSAADIVKIASNNGGARALQALIDHWSTLSGKT | 92 | NN |
| *Burkholderia* | FTLTDIVEMAGNNGGAQALKAVLEHGSTLDERG | 93 | NN |

-continued

| Organism | Repeat Unit Sequence $(X_{1-11}X_{12}X_{13}X_{14-33, \; 34, \; or \; 35})$ | SEQ ID | BCR $(X_{12}X_{13})$ |
|---|---|---|---|
| *Burkholderia* | FTLTDIVKMAGNNGGAQALKAVLEHGPTLDERG | 94 | NN |
| *Burkholderia* | FTLTDIVKMAGNNGGAQALKVVLEHGPTLRQRG | 95 | NN |
| *Burkholderia* | FTLTDIVKMASNNGGAQALKAVLEHGPTLDERG | 96 | NN |
| *Burkholderia* | FSAADIVKIAGNSGGAQALQAVISHRAALTQAG | 97 | NS |
| *Burkholderia* | FSGGDAVSTVVRSGGAQSVASGGTASGTTVSAG | 98 | RS |
| *Burkholderia* | FRQTDIVKMAGSGGSAQALNAVIKHGPTLRQRG | 99 | SG |
| *Burkholderia* | FSLIDIVEIASNGGAQALKAVLKYGPVLTQAGR | 100 | SN |
| *Burkholderia* | FSGGDAAGTVVSSGGAQNVTGGLASGTTVASGG | 101 | SS |
| *Paraburkholderia* | FNLTDIVEMAANSGGAQALKAVLEHGPTLRQRG | 102 | NS |
| *Paraburkholderia* | FNRASIVKIAGNSGGAQALQAVLKHGPTLDERG | 103 | NS |
| *Paraburkholderia* | FSQANIVKMAGNSGGAQALQAVLDLELVFRERG | 104 | NS |
| *Paraburkholderia* | FSQPDIVKMAGNSGGAQALQAVLDLELAFRERG | 105 | NS |
| *Paraburkholderia* | FSLIDIVEIASNGGAQALKAVLKYGPVLMQAGR | 106 | SN |
| *Francisella* | YKSEDIIRLASHDGGSVNLEAVLRLHSQLTRLG | 107 | HD |
| *Francisella* | YKPEDIIRLASHGGGSVNLEAVLRLNPQLIGLG | 108 | HG |
| *Francisella* | YKSEDIIRLASHGGGSVNLEAVLRLHSQLTRLG | 109 | HG |
| *Francisella* | YKSEDIIRLASHGGGSVNLEAVLRLNPQLIGLG | 110 | HG |
| *L. quateirensis* | LGHKELIKIAARNGGGNNLIAVLSCYAKLKEMG | 111 | RN |
| *Paraburkholderia* | FNLTDIVEMAGKGGGAQALKAVLEHGPTLRQRG | 112 | KG |
| *Paraburkholderia* | FRQADIIKIAGNDGGAQALQAVIEHGPTLRQHG | 113 | ND |
| *Paraburkholderia* | FSQADIVKIAGNDGGTQALHAVLDLERMLGERG | 114 | ND |
| *Paraburkholderia* | FSRADIVKIAGNGGGAQALKAVLEHEATLDERG | 115 | NG |
| *Paraburkholderia* | FSRADIVRIAGNGGGAQALYSVLDVEPTLGKRG | 116 | NG |
| *Paraburkholderia* | FSQPDIVKMASNIGGAQALQAVLELEPALRERG | 117 | NI |
| *Paraburkholderia* | FSQPDIVKMAGNIGGAQALQAVLSLGPALRERG | 118 | NI |
| *Paraburkholderia* | FSQPEIVKIAGNIGGAQALHTVLELEPTLHKRG | 119 | NI |
| *Paraburkholderia* | FSQSDIVKIAGNIGGAQALQAVLDLESMLGKRG | 120 | NI |
| *Paraburkholderia* | FSQSDIVKIAGNIGGAQALQAVLELEPTLRESD | 121 | NI |
| *Paraburkholderia* | FNPTDIVKIAGNKGGAQALQAVLELEPALRERG | 122 | NK |
| *Paraburkholderia* | FSPTDIIKIAGNNGGAQALQAVLDLELMLRERG | 123 | NN |
| *Paraburkholderia* | FSQADIVKIAGNNGGAQALYSVLDVEPTLGKRG | 124 | NN |
| *Paraburkholderia* | FSRGDIVTIAGNNGGAQALQAVLELEPTLRERG | 125 | NN |
| *Paraburkholderia* | FSRIDIVKIAANNGGAQALHAVLDLGPTLRECG | 126 | NN |
| *Paraburkholderia* | FSQADIVKIVGNNGGAQALQAVFELEPTLRERG | 127 | NN |
| *Paraburkholderia* | FSQPDIVRITGNRGGAQALQAVLALELTLRERG | 128 | NR |
| *Legionellales* | FKADDAVRIACRTGGSHNLKAVHKNYERLRARG | 129 | RT |
| *Legionellales* | FNADQVIKIVGHDGGSNNIDVVQQFFPELKAFG | 130 | HD |
| *L. maceachernii* | FSAEQIVRIAAHIGGSRNIEATIKHYAMLTQPP | 131 | HI |

-continued

| Organism | Repeat Unit Sequence $(X_{1-11}X_{12}X_{13}X_{14-33, \ 34, \ or \ 35})$ | SEQ ID | BCR $(X_{12}X_{13})$ |
|---|---|---|---|
| *Francisella* | YKSEDIIRLASHDGGSVNLEAVLRLNPQLIGLG | 132 | HD |
| *Francisella* | YKSEDIIRLASHDGGSINLEAVLRLNPQLIGLG | 133 | HD |
| *Francisella* | YKSEDIIRLASSNGGSVNLEAVLRLNPQLIGLG | 134 | SN |
| *Francisella* | YKSEDIIRLASSNGGSVNLEAVIAVHKALHSNG | 135 | SN |
| *Legionellales* | FSADQVVKIAGHSGGSNNIAVMLAVFPRLRDFG | 136 | HS |
| *Francisella* | YKINHCVNLLKLNHDGFMLKNLIPYDSKLTGLG | 137 | LN |

Residues $X_{12}X_{13}$ of the RU may a base contacting residues (BCR) as listed in the table 8 and may be chosen based upon the target nucleic acid sequence.

In certain aspects, the last RU in the DBP may be a half RU. In certain aspects, the half RU may include a sequence that is at least 80%, at least 90%, at least 95% or a 100% identical to the half RU from *L. quateirensis* (FNAEQI-VRMVS $X_{12}X_{13}$ GGSKNL; SEQ ID NO: 138). In certain aspects, the half RU may include a sequence that is at least 80%, at least 90%, at least 95% or a 100% identical to the half RU from *Francisella* (YNKKQIVLIAS $X_{12}X_{13}$ SGG; SEQ ID NO: 139)

In certain aspects, the polypeptide comprises an N-cap region, where the C-terminus (i.e., the last amino acid) of the N-cap region is covalently linked to the N-terminus (i.e., the first amino acid) of the first RU of the DBP either directly or via a linker. In certain aspects, the N-cap region is the N-terminus of *L. quateirensis* protein and may have an amino acid sequence that is at least 80% (e.g., at least 85%, at least 90%, 95%, or 99%, or a 100%) identical to the amino acid sequence:

MPDLELNFAIPLHLFDDETVFTHDATNDNSQASS-
    SYSSKSSPASANARKR
    TSRKEMSGPPSKEPANTKSRRANS
    QNNKLSLADRLTKYNIDEEFYQTRSD-
    SLLSLNYTK    KQIERLILYKGRTSAVQQLLCK-
    HEELLNLISPDG (SEQ ID NO: 140) In certain
    aspects, the N-cap region is a N-terminal domain or a
    fragment thereof from TALE proteins like those
    expressed in *Burkholderia*, Paraburkholderia, or
    *Xanthomonas*.

In certain aspects, the polypeptide comprises a C-cap region, where the N-terminus (i.e., the first amino acid) of the C-terminal domain is covalently linked to the C-terminus (i.e., the last amino acid) of the last RU or the half-repeat unit, if present, in the DBP either directly or via a linker. In certain aspects, the C-cap region is the C-terminal domain of *L. quateirensis* protein and may have an amino acid sequence that is at least 80% (e.g., at least 85%, at least 90%, 95%, or 99%, or a 100%) identical to the amino acid sequence:

(SEQ ID NO: 141)
ALVKEYFPVFSSFHFTADQIVALICQSKQCFRNLKKNHQQWKNKGLSAE

QIVDLILQETPPKPNFNNTSSSTPSPSAPSFFQGPSTPIPTPVLDNSPA

PIFSNPVCFFSSRSENNTEQYLQDSTLDLDSQLGDPTKNFNVNNFWSLF

PFDDVGYHPHSNDVGYHLHSDEESPFFDF

In certain aspects, the C-cap region has the amino acid sequence    ALVKEYFPVFSSFHFTADQIVALICQS KQCFRNLKKNHQQWKNKGLSAEQIVDLILQETP PKP (SEQ ID NO: 142). In certain aspects, the C-cap region domain is a C-terminal domain or a fragment thereof from TALE proteins like those expressed in *Burkholderia*, Paraburkholderia, or *Xanthomonas*.

Mixed DNA Binding Domains

In some aspects, the present disclosure provides DNA binding domains in which the repeat units, the N-cap, and the C-ap can be derived from any one of *Ralstonia solanacearum*, *Xanthomonas* spp., *Legionella quateirensis*, *Burkholderia*, Paraburkholderia, or *Francisella*. For example, the present disclosure provides a DNA binding domain wherein the plurality of repeat units are selected from any one of the RUs as provided herein and can further comprise an N-cap and/or C-cap as provided herein.

Functional Domains

A DBP as disclosed herein can be associated with a functional domain as described in the preceding sections. The functional domain can provide different types of activity, such as genome editing, gene regulation (e.g., activation or repression), or visualization of a genomic locus via imaging. In certain aspects, the functional domain is heterologous to the DBP. Heterologous in the context of a functional domain and a DBP as used herein indicates that these domains are derived from different sources and do not exist together in nature. In some aspects, the nuclease can be a cleavage half domain, which dimerizes to form an active full domain capable of cleaving DNA. In other aspects, the nuclease can be a cleavage domain, which is capable of cleaving DNA without needing to dimerize. For example, a nuclease comprising a cleavage half domain can be an endonuclease, such as FokI or Bfil. In some aspects, two cleavage half domains (e.g., FokI or Bfil) can be fused together to form a fully functional single cleavage domain.

A nuclease domain fused to a DBP can be an endonuclease or an exonuclease. An endonuclease can include restriction endonucleases and homing endonucleases. An endonuclease can also include S1 Nuclease, mung bean nuclease, pancreatic DNase I, micrococcal nuclease, or yeast HO endonuclease. An exonuclease can include a 3'-5' exonuclease or a 5'-3' exonuclease. An exonuclease can also include a DNA exonuclease or an RNA exonuclease. Examples of exonuclease includes exonucleases I, II, III, IV, V, and VIII;

DNA polymerase I, RNA exonuclease 2, and the like.

A nuclease domain fused to a DBP as disclosed herein can be a restriction endonuclease (or restriction enzyme). In some instances, a restriction enzyme cleaves DNA at a site removed from the recognition site and has a separate binding and cleavage domains. In some instances, such a restriction enzyme is a Type IIS restriction enzyme.

As another example, DBP as disclosed herein can be linked to a gene regulating domain. A gene regulation domain can be an activator or a repressor. For example, a DBP as disclosed herein can be linked to an activation domain, such as VP16, VP64, p65, p300 catalytic domain, TET1 catalytic domain, TDG, Ldb1 self-associated domain, SAM activator (VP64, p65, HSF1), or VPR (VP64, p65, Rta). Alternatively, a DBP can be linked to a repressor, such as KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2. The terms "repressor," "repressor domain," and "transcriptional repressor" are used herein interchangeably to refer to a polypeptide that decreases expression of a gene.

In some aspects, a DBP as disclosed herein can be linked to a DNA modifying protein, such as DNMT3a. A DBP can be linked to a chromatin-modifying protein, such as lysine-specific histone demethylase 1 (LSD1). A DBP can be linked to a protein that is capable of recruiting other proteins, such as KRAB. The DNA modifying protein (e.g., DNMT3a) and proteins capable of recruiting other proteins (e.g., KRAB) can serve as repressors of transcription. Thus, DBP linked to a DNA modifying protein (e.g., DNMT3a) or a domain capable of recruiting other proteins (e.g., KRAB, a domain found in transcriptional repressors, such as Kox1) can provide gene repression functionality, can serve as transcription factors, wherein the DBP provides specificity and targeting and the DNA modifying protein and the protein capable of recruiting other proteins provides gene repression functionality, which can be referred to as an engineered genomic regulatory complex or a DBP-gene regulator (DBP-GR) and, more specifically, as a DBP-transcription factor (DBP-TF).

In certain aspects, the functional domain may be an imaging domain, e.g., a fluorescent protein, biotinylation reagent, tag (e.g., 6×-His or HA). A DBP can be linked to a fluorophore, such as Hydroxycoumarin, methoxycoumarin, Alexa fluor, aminocoumarin, Cy2, FAM, Alexa fluor 488, Fluorescein FITC, Alexa fluor 430, Alexa fluor 532, HEX, Cy3, TRITC, Alexa fluor 546, Alexa fluor 555, R-phyco-erythrin (PE), Rhodamine Red-X, Tamara, Cy3.5, Rox, Alexa fluor 568, Red 613, Texas Red, Alexa fluor 594, Alexa fluor 633, Allophycocyanin, Alexa fluor 633, Cy5, Alexa fluor 660, Cy5.5, TruRed, Alexa fluor 680, Cy7, GFP, or mCHERRY.

In certain aspects, the DBP is not fused with a functional domain having a genome modifying activity, such as, cleavage activity, DNA methylation activity, chromatin-modifying protein, transcriptional activation, or transcriptional repression.

Targets

In some aspects, a cell that expresses the DBP disclosed herein may be a mammalian cell such as a stem cell (e.g., human embryonic stem cell or induced pluripotent stem cell), human hematopoietic stem cell "HSC" (e.g. CD34$^+$ HSC), hematopoietic progenitor cell (HPC), a cell in the erythroid lineage, a lymphocyte, a T-cell, CAR-T cells, a cancer cell, ex vivo cell, etc. A cell may be selected for stable expression of the DBP. A cell may be selected for expressing a threshold level of the DBP. A cell selected for expression of the DBP may be subjected to expansion, freeze/thaw or otherwise prepared for introduction into a subject in need thereof.

A cell expressing a DBP either constitutively or in an inducible manner may be administered to the subject, for instance in the circulatory system by means of intravenous delivery or delivery into a solid tissue such as bone marrow.

Exemplary mammalian cells can include, but are not limited to, 293A cell line, 293FT cell line, 293F cells, 293 H cells, HEK 293 cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, T-REx™-HeLa cell line, NC-HIMT cell line, PC12 cell line, primary cells (e.g., from a human) including primary T cells, primary hematopoietic stem cells, primary human embryonic stem cells (hESCs), and primary induced pluripotent stem cells (iPSCs).

In some cases, a target cell is a cancerous cell. Cancer can be a solid tumor or a hematologic malignancy. The solid tumor can include a sarcoma or a carcinoma. Exemplary sarcoma target cell can include, but are not limited to, cell obtained from alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

Exemplary carcinoma target cell can include, but are not limited to, cell obtained from anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

Alternatively, the cancerous cell can comprise cells obtained from a hematologic malignancy. Hematologic malignancy can comprise a leukemia, a lymphoma, a myeloma, a non-Hodgkin's lymphoma, or a Hodgkin's lymphoma. In some cases, the hematologic malignancy can be a T-cell based hematologic malignancy. Other times, the hematologic malignancy can be a B-cell based hematologic malignancy. Exemplary B-cell based hematologic malignancy can include, but are not limited to, chronic lymphocytic leukemia (CLL), small lymphocytic lymphoma (SLL), high-risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. Exemplary T-cell based hematologic malignancy can include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some cases, a cell can be a tumor cell line. Exemplary tumor cell line can include, but are not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

Genetic modification can involve introducing a functional gene for therapeutic purposes, knocking out a gene for therapeutic gene, or engineering a cell ex vivo (e.g., HSCs or CAR T cells) to be administered back into a subject in need thereof. Cells, such as hematopoietic stem cells (HSCs) and T cells, can be engineered ex vivo to express the DBP. Alternatively, nucleic acid encoding the DBP can be directly administered to a subject in need thereof.

The target gene may be an endogenous gene such as human fetal gamma globin gene, PDCD 1 gene, a CTLA4 gene, a LAG3 gene, a TET2 gene, a ETLA gene, a HA VCR2 gene, a CCR5 gene, a CXCR4 gene, a TRA gene, a TRE gene, a E2M gene, an albumin gene, a HEE gene, a HEA1 gene, a TTR gene, a NR3C1 gene, a CD52 gene, an erythroid specific enhancer of the ECL11A gene, a CELE gene, a TGFER1 gene, a SERPINA1 gene, a HEV genomic DNA in infected cells, a CEP290 gene, a DMD gene, a CFTR gene, or an IL2RG gene.

Compositions

The compositions disclosed herein may comprise one or more DBP, polynucleotides encoding the DBPs, vectors comprising same, and cell comprising the DBP or polynucleotides encoding the DBPs, as contemplated herein. These compositions are useful for increasing a human γ-globin gene in a cell or a population of cells. The cell may be a hematopoietic cell, e.g., a hematopoietic stem or progenitor cell, or a CD34$^+$ cell.

In certain aspects, the polypeptides described herein may be present in a pharmaceutical composition comprising a pharmaceutically acceptable excipient. In certain aspects, the polypeptides are present in a therapeutically effective amount in the pharmaceutical composition. A therapeutically effective amount can be determined based on an observed effectiveness of the composition. A therapeutically effective amount can be determined using assays that measure the desired effect in a cell.

The pharmaceutical compositions can be administered ex vivo or in vivo to a subject in order to practice the therapeutic methods and uses described herein.

The pharmaceutical compositions of the present disclosure can be formulated to be compatible with the intended method or route of administration; exemplary routes of administration are set forth herein. Suitable pharmaceutically acceptable or physiologically acceptable diluents, carriers or excipients include, but are not limited to, nuclease inhibitors, protease inhibitors, a suitable vehicle such as physiological saline solution or citrate buffered saline.

A pharmaceutical composition comprising the DBP as disclosed herein and a pharmaceutically acceptable excipient is provided. A pharmaceutical composition comprising the nucleic acid as disclosed herein or the vector as disclosed herein and a pharmaceutically acceptable excipient is provided. A pharmaceutical composition comprising the host cell of comprising the DBP disclosed herein or a nucleic acid as disclosed herein or the vector as disclosed herein is provided.

The compositions of the present disclosure find use in a variety of therapeutic and research applications.

In certain aspects, the compositions disclosed herein such as a compsotion comprising a nucleic acid encoding a DBP that displaces the TF ZBTB7A from the fetal γ-globin gene promoter and results in expression of fetal hemoglobin-γ (HBG) from the fetal γ-globin gene, the DBP encoded by the nucleic acid, or a cell comprising the nucleic acid or the DBP may be in a method for the increasing expression of fetal hemoglobin-γ (HBG) in a subject in need thereof. The subject may have a blood cell disorder such as a hemoglobinopathy. In certain aspects the subject has sickle cell anemia or thalassemia.

Delivery

The DBP disclosed herein and compositions comprising the disclosed polypeptides can be delivered into a target cell by any suitable means, including, for example, by contacting the cell with the polypeptide or a nucleic acid encoding the polypeptide.

In certain aspects, the DBP or a can be delivered into cells in a particular tissue (e.g., a solid tumor) by injecting a composition comprising the positively charged polypeptide directly into the solid tumor.

In other aspects, administration involves systemic administration (e.g., intravenous, intraperitoneal, intramuscular, subdermal, or intracranial infusion), direct injection (e.g., intrathecal), or topical application, etc.

Nucleic acids encoding the DBPs may be delivered into a target cell by e.g., vectors (e.g., viral or non-viral vectors), non-vector based methods (e.g., using naked DNA or DNA complexes, e.g., cationic liposomes, polymeric nanoparticles, polymers, etc.), or a combination thereof. Nucleic acids encoding the DBPs can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). The nucleic acid vector can also include any suitable number of regulatory/control elements, e.g., promoters, enhancers, introns, polyadenylation signals, Kozak consensus sequences, or internal ribosome entry sites (IRES).

Viral vectors used for delivering the nucleic acid encoding a DBP include retroviral vectors, lentiviral vectors, adenoviral vectors, adeno-associate viral vectors, and the like.

Routes of Administration

Nucleic acid encoding DBP or cells comprising such a nucleic acid or cells expressing the DBP, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Nucleic acids administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein.

Administration can be provided as a periodic bolus (for example, intravenously) or as continuous infusion from an internal reservoir or from an external reservoir (for example, from an intravenous bag or implantable pump). Nucleic acids and/or cells can be administered locally, for example, by continuous release from a sustained release drug delivery device.

Subjects

A subject in need of modulation of gene expression by administering a composition as disclosed herein such as in need of increased expression of HBG may have a deficiency of globin synthesis such as thalassemia syndromes and/or structural abnormalities of globin such as sickle cell syndromes and syndromes associated with unstable hemoglobins. These diseases are referred to as hemoglobinopathy. Thalassemia syndromes result from deficiencies in either alpha-globin (α-thalassemia) or beta-like globin (β-thalassemia) chains. The diseases become apparent when the deficient globin is required during development. α-Thalassemia is symptomatic during gestation, as α-globin is required for fetal hemoglobin (HbF, α2γ2). As β-globin is not required in large amounts before birth, β-thalassemia is asymptomatic until around 6 months after birth. Mutations that cause prolonged production of fetal γ-globin chains may present later, at 2 to 4 years of age.

The major pathologic process in thalassemia is the imbalance of alpha and non-alpha globin chain accumulation. The unaffected chains, produced in normal amounts, precipitate during erythropoiesis. In β-thalassemia, the precipitated α-globin chains are particularly toxic, damaging cell membranes and causing apoptosis. β0-Thalassemias are characterized by a complete absence of any beta globin chains. β+-Thalassemias are characterized by detectable presence of a reduced amount of beta chains. There are three principal categories of beta thalassemias: thalassemia major, thalassemia intermedia, and thalassemia minor.

In certain instances, a person carries the beta thalassemia trait and the hemoglobin S trait (the abnormal hemoglobin found in people with sickle cell disease), which leads to HbS beta thalassemia. The severity of this condition varies according to the amount of normal beta globin produced by the beta globin gene. When no beta globin is produced by the beta globin gene, the condition is almost identical to sickle cell disease.

In sickle cell disease (SCD), one amino acid substitution in the beta globin chain results in the generation of hemoglobin S (HbS). Upon deoxygenation, HbS molecules undergo aggregation and polymerization ultimately leading to a morphological distortion of the red cells, which acquire a sickle or holly-leaf shape. Sickle cell anemia βS/βS, a common form of sickle cell disease (SCD), is caused by Hemoglobin S (HbS). Additional mutations in the β-globin gene can also cause other abnormalities in β-globin, leading to other types of sickle cell disease. These abnormal forms of β-globin are often designated by letters of the alphabet or sometimes by a name. In these other types of sickle cell disease, one β-globin subunit is replaced with HbS and the other β-globin subunit is replaced with a different abnormal variant, such as hemoglobin C (HbC; β-globin allele noted as $\beta^C$) or hemoglobin E (HbE; β-globin allele noted as $\beta^E$).

In hemoglobin SC (HbSC) disease, the β-globin subunits are replaced by HbS and HbC. HbC results from a mutation in the β-globin gene and is the predominant hemoglobin found in people with HbC disease ($\alpha_2\beta^C_2$). HbC disease is relatively benign, producing a mild hemolytic anemia and splenomegaly. The severity of HbSC disease is variable, but it can be as severe as sickle cell anemia.

HbE is caused when the amino acid glutamic acid is replaced with the amino acid lysine at position 26 in β-globin, noted as Glu26Lys or E26K. People with HbE disease have a mild hemolytic anemia and mild splenomegaly. In some cases, the HbE mutation is present with HbS. In these cases, a person may have more severe signs and symptoms associated with sickle cell anemia, such as episodes of pain, anemia, and abnormal spleen function.

In certain aspects, the subject is a subject who has been diagnosed as having a hemoglobinopathy selected from the group consisting of hemoglobin C disease, hemoglobin E disease, sickle cell anemia, sickle cell disease (SCD), thalassemia, β-thalassemia, thalassemia major, thalassemia intermedia, hemoglobin Bart syndrome and hemoglobin H disease.

The cells may be administered as part of a bone marrow or cord blood transplant in an individual that has or has not undergone bone marrow ablative therapy. In one aspect, cells contemplated herein are administered in a bone marrow transplant to an individual that has undergone chemoablative or radioablative bone marrow therapy.

In one aspect, a dose of cells expressing the DBPs is delivered to a subject intravenously. In one aspect, the cells are hematopoietic stem cells which are intravenously administered to a subject.

In one aspect, the effective amount of genome edited cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another aspect, the effective amount of genome edited cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Materials and Methods

Cell culture. HUDEP-2 cells (PMID 23533656) were grown in StemSpan SFEM (Stemcell Technologies) supplemented with 2% PennStrep, 1% L-Glutamine, 1 ug/mL doxycycline, 100 ng/mL recombinant human SCF (Peprotech), 3 IU/mL recombinant human EPO (Peprotech), and 10-6 M dexamethasone.

TALE transfection. mRNA was in vitro transcribed using T7 mScript™ Standard mRNA Production System (Cellscript) following manufacturer's instructions and RNA size and concentrations were determined using the Advanced Analytical Fragment Analyzer (Agilent). $5\times10^5$ HUDEP-2 cells were electroporated with 4 ug TALE mRNA and 100 ul BTXpress solution (BTX) in 96-well cuvette (BTX) using the ECM 830 Square Wave Electroporation System (Harvard Apparatus) and HT200 Plate Handler (BTX) with 250 mS interval, 250V for 5 msec pulse. Electroporated cells were transferred to 12 or 6-well plates, and RNA was harvested 12, 24, or 48 hours later. After the initial time course experiment, all samples were harvested at 48 hours.

Generation of Clonal Lines. $5\times10^6$ HUDEP-2 cells were transfected with TALEN pairs recognizing the AAVS1 safe harbor locus (5'-TTTCTGTCACCAATCCT-3' (SEQ ID NO: 143) and 5'-TCCCCTCCACCCCACAGT-3' (SEQ ID NO: 144); 2.5 ug mRNA per TALEN monomer), together with 2.5 ug AAVS1 donor plasmid using the Amaxa Human CD34+ Cell Nucleofector Kit (Lonza) on an Amaxa Nucleofector II Device (Lonza). Donor plasmid contains a splice acceptor site followed by T2A and GFP to utilize an endogenous promoter to drive expression of GFP after integration and an EF1alpha-driven TALE followed by WPRE (sequences provided below). Cells were maintained in a T-25 flask and media was changed every 24 hours post-transfection for two days. Approximately 7-12 days post-transfection, single cells were sorted for GFP expression into 96-well plates using the MoFlo Astrios (Beckman Coulter). Cells were maintained in 96-well plates for –12 days with doxycycline supplemented every two days and media changes on days 8 and 10. Wells containing cells were identified, consolidated, and further maintained.

Globin TaqMan qPCR. Total RNA was extracted from 2-5$\times10^5$ HUDEP-2 cells from clonal lines expressing stably-integrated TALEs or WT cells transfected with TALE mRNA using the RNeasy Micro Kit (Qiagen), and 100 ng RNA was reverse transcribed with iScript Reverse Transcription Supermix (Bio-Rad). qPCRs were run with multiplexed Taqman primer/probe sets specific to HBG (Hs00361131_g1, VIC) and HBB (Hs00747223_g1, FAM) from ThermoFisher Scientific, cDNA diluted at a 1:10 ratio, and SsoAdvanced Universal Probes Supermix (Bio-Rad) on a Bio-Rad CFX96 Real Time System. Primer/probe sets were confirmed to be accurate and robust in multiplexing assays as no difference was observed when tested individually or multiplexed. In TALE transfection experiments, HBG measurements were normalized to measurements of HBB and compared to transfected control cells in biological triplicate. For analysis of stably-integrated TALE HUDEP-2 cell lines, amount of HBG expression was normalized to total HBB and HBG expression, with 2-5 measurements taken at different timepoints in culture per sample.

FLAG Immunofluorescence. In a 24-well poly-1-lysine coated cover glass bottom plate (BioMedTech Laboratories, Inc.), $7.5\times10^4$ cells were deposited in a 30 ul droplet to the center of the well and allowed to settle for 40 minutes. Cells were fixed with 4% PFA (Polysciences Inc, #18814-10) for 10 minutes at room temperature, washed 3 times for 3 minutes each with PBS, permeabilized with 0.25% Triton (Triton X-100) in PBS for 10 minutes, and washed 3 times for 5 minutes each with PBS. Cover glass bottoms were incubated with blocking solution (2% BSA-PBS (Jackson Immunoresearch, #001-000-161)) for 45 minutes, then incubated with a 1:500 dilution of primary mouse monoclonal ANTI-FLAG® M2 antibody (F1804; Sigma) in 2% BSA-PBS for 2 hours, washed 3 times for 3 minutes each with 0.05% Tween (Bio-rad, #161-0781) in PBS, incubated with a 1:500 dilution of secondary antibody conjugated to either Cy3 or AlexaFluor-647 (Jackson Labs) for 1 hour, and washed 3 times for 5 minutes each with 0.05% Tween-PBS with the second wash containing 0.1 mg/mL DAPI solution (100 ng/mL in 1×PBS) and washing for 10 minutes. Lastly, cell samples in individual wells were mounted with 7-10 uL Prolong Gold (Molecular Probes P36930) antifade, sealed with 12 mm coverglasses (1.5, Electron Microscopy Sciences), and cured either overnight or for at least 2 hours prior to imaging. Samples were imaged using an inverted Nikon Eclipse Ti widefield microscope equipped with an Andor Zyla 4.2CL10 CMOS camera with a 4.2-megapixel sensor and 6.5 μm pixel size (18.8 mm diagonal FOV). Focused 3D cell images were acquired using a 40×0.9 NA air objective. Acquired images were subject to 100 rounds of iterative blind deconvolution using Microvolution software (Microvolution, CA) to minimize the effect of out-of-focus blurring that is inherent to widefield microscopy optics. Deconvolved images were processed using in-house Matlab (version 2017B, Mathworks, Natick, MA) scripts to numerically estimate the average FLAG protein content in every cell nucleus, and for downstream statistical analysis.

Globin FACS. Approximately 1×106 cells were harvested, fixed with 4% PFA for 15 minutes, permeabilized with acetone, incubated with 1:200 anti-HbF-APC (MHFH05; ThermoFisher) and 1:400 anti-Hemoglobin β (sc-21757; Santa Cruz) for at least 20 minutes at 4° C., rinsed with 0.5% BSA-PBS, and stained with DAPI for 15 minutes. FACS was run on a CytoFLEX S (Beckman Coulter).

TABLE 1

Target sequences from □-globin proximal promoter.

| TALE Protein | Target Sequence | SEQ ID NO |
|---|---|---|
| E1 | TGCCTTGACCAATAGCCTT | 145 |
| D11 | TGCCTTGACCAATAG | 146 |
| D2 | GCCTTGTCAAGGCTATTGGTCA | 147 |
| A11 | ATCCTCTTGGGGGCCCC | 2 |

TABLE 1-continued

Target sequences from □-globin proximal promoter.

| TALE Protein | Target Sequence | SEQ ID NO |
|---|---|---|
| B1 | CCTCTTGGGGGCCCCTTCCC | 3 |
| B5 | TCCCCACACTATCTC | 148 |
| B7 | TCCCCACACTATCTCAATG | 149 |

TABLE 2

TALE Protein Domain Sequences

| TALE Protein Domain | Sequence | SEQ ID NO |
|---|---|---|
| N-terminus region | MVDLRTLGYSQQQQEKIKPKVRSTVAQHH EALVGHGFTHAHIVALSQHPAALGTVAVK YQDMIAALPEATHEAIVGVGKQWSGARAL EALLTVAGELRGPPLQLDTGQLLKIAKRGG VTAVEAVHAWRNALTGA | 150 |
| C-terminus region | SIVAQLSRPDPALAALTNDHLVALACLGGR PALDAVKKGLPHAPALIKRTNRRIPERTSHR VA | 151 |
| NI RVD (A) | LTPDQVVAIASNIGGKQALETVQRLLPVLC QDHG | 23 |
| NG RVD (T) | LTPDQVVAIASNGGGKQALETVQRLLPVLC QDHG | 22 |
| HD RVD (C) | LTPDQVVAIASHDGGKQALETVQRLLPVLC QDHG | 24 |
| NH RVD (G) | LTPDQVVAIASNHGGKQALETVQRLLPVLC QDHG | 21 |
| NI last half repeat (A) | LTPDQVVAIASNIGGRPALE | 152 |
| NG last half repeat (T) | LTPDQVVAIASNGGGRPALE | 153 |
| HD last half repeat (C) | LTPDQVVAIASHDGGRPALE | 154 |
| NH last half repeat (G) | LTPDQVVAIASNHGGRPALE | 155 |

```
All protein sequence:
                                    (SEQ ID NO: 156)
MDYKDHDGDYKDHDIDYKDDDDKMAPKKKRKVGIHRGVPMVDLRTL

GYSQQQQEKIKPKVRSTVAQHHEALVGHGFTHAHIVALSQHPAALGTVA

VKYQDMIAALPEATHEAIVGVGKQWSGARALEALLTVAGELRGPPLQLD

TGQLLKIAKRGGVTAVEAVHAWRNALTGAPLNLTPDQVVAIASNIGGKQ

ALETVQRLLPVLCQDHGLTPDQVVAIASNGGGKQALETVQRLLPVLCQD

HGLTPDQVVAIASHDGGKQALETVQRLLPVLCQDHGLTPDQVVAIASHD

GGKQALETVQRLLPVLCQDHGLTPDQVVAIASNGGGKQALETVQRLLPV

LCQDHGLTPDQVVAIASHDGGKQALETVQRLLPVLCQDHGLTPDQVVAI

ASNGGGKQALETVQRLLPVLCQDHGLTPDQVVAIASNGGGKQALETVQR

LLPVLCQDHGLTPDQVVAIASNHGGKQALETVQRLLPVLCQDHGLTPDQ

VVAIASNHGGKQALETVQRLLPVLCQDHGLTPDQVVAIASNHGGKQALE

TVQRLLPVLCQDHGLTPDQVVAIASNHGGKQALETVQRLLPVLCQDHGL

TPDQVVAIASNHGGKQALETVQRLLPVLCQDHGLTPDQVVAIASHDGGK

QALETVQRLLPVLCQDHGLTPDQVVAIASHDGGKQALETVQRLLPVLCQ

DHGLTPDQVVAIASHDGGKQALETVQRLLPVLCQDHGLTPDQVVAIASH

DGGRPALESIVAQLSRPDPALAALTNDHLVALACLGGRPALDAVKKGLP

HAPALIKRTNRRIPERTSHRVAGS

B1 protein sequence:
                                    (SEQ ID NO: 157)
MDYKDHDGDYKDHDIDYKDDDDKMAPKKKRKVGIHRGVPMVDLRTL

GYSQQQQEKIKPKVRSTVAQHHEALVGHGFTHAHIVALSQHPAALGTVA

VKYQDMIAALPEATHEAIVGVGKQWSGARALEALLTVAGELRGPPLQLD

TGQLLKIAKRGGVTAVEAVHAWRNALTGAPLNLTPDQVVAIASHDGGKQ

ALETVQRLLPVLCQDHGLTPDQVVAIASHDGGKQALETVQRLLPVLCQD

HGLTPDQVVAIASNGGGKQALETVQRLLPVLCQDHGLTPDQVVAIASHD

GGKQALETVQRLLPVLCQDHGLTPDQVVAIASNGGGKQALETVQRLLPV

LCQDHGLTPDQVVAIASNGGGKQALETVQRLLPVLCQDHGLTPDQVVAI

ASNHGGKQALETVQRLLPVLCQDHGLTPDQVVAIASNHGGKQALETVQR

LLPVLCQDHGLTPDQVVAIASNHGGKQALETVQRLLPVLCQDHGLTPDQ

VVAIASNHGGKQALETVQRLLPVLCQDHGLTPDQVVAIASNHGGKQALE

TVQRLLPVLCQDHGLTPDQVVAIASHDGGKQALETVQRLLPVLCQDHGL

TPDQVVAIASHDGGKQALETVQRLLPVLCQDHGLTPDQVVAIASHDGGK

QALETVQRLLPVLCQDHGLTPDQVVAIASHDGGKQALETVQRLLPVLCQ

DHGLTPDQVVAIASNGGGKQALETVQRLLPVLCQDHGLTPDQVVAIASN

GGGKQALETVQRLLPVLCQDHGLTPDQVVAIASHDGGKQALETVQRLLP

VLCQDHGLTPDQVVAIASHDGGKQALETVQRLLPVLCQDHGLTPDQVVA

IASHDGGRPALESIVAQLSRPDPALAALTNDHLVALACLGGRPALDAVK

KGLPHAPALIKRTNRRIPERTSHRVAGS
```

Example 1: Tales for Specific Regulation of a Target Gene

Transcription factors regulate gene expression. Gene expression can be artificially perturbed by expressing dominant negative forms of transcription factors that lack activation/repression domains. However, naturally occurring TFs bind to thousands of gene in the genome, making dominant negative forms of TFs unsuitable for targeting a specific gene. Provided herein are DNA binding proteins that not only displace an endogenous TF but are specific for a target gene. The DNA binding protein replaces endogenous TF from only a target gene since it binds to a sequence present only in the target gene. As a proof of concept, TALE proteins that specifically bind to a sequence in a target gene were designed and tested.

β-hemoglobinopathies, such as, sickle cell disease, β-thalassemia, are caused by mutations in the adult β-globin gene. During development, globin genes undergo switching: adult β-globin is expressed and the fetal γ-globin promoter is directly bound and silenced by the transcription factors ZBTB7A and BCL11A (Bauer, D. et al., Blood 2012). Mutations in the fetal γ-globin promoter result in incomplete silencing of the fetal γ-globin promoter (Hereditary Persistence of Fetal Hemoglobin; HPFH). HPFH patients who inherit sickle cell gene (Hb S) show symptomatic amelioration of sickle cell disease. Accordingly, reactivation of fetal globin expression to increase level of functional Hb is avidly being sought as a therapeutic avenue.

Mutations in HPFH patients cluster in TF binding sites. TALE proteins that bind to TF binding sites were designed to test the hypothesis that displacing TFs bound to γ-globin proximal promoter may reactivate fetal γ-globin expression. Four TALEs (A11, B1, B5, and B7) that bind to different nucleotide sequences spanning the binding site for the TF ZBTB7A and three TALEs (D2, D11, and E1) that bind to different nucleotide sequences spanning the binding site for the TF BCL11A were designed. mRNA encoding the TFs were transfected into HUDEP-2 cells and relative expression of fetal hemoglobin (HBG) as compared to adult hemoglobin (HBB) at various time points after transfection was measured.

Figure 1B:
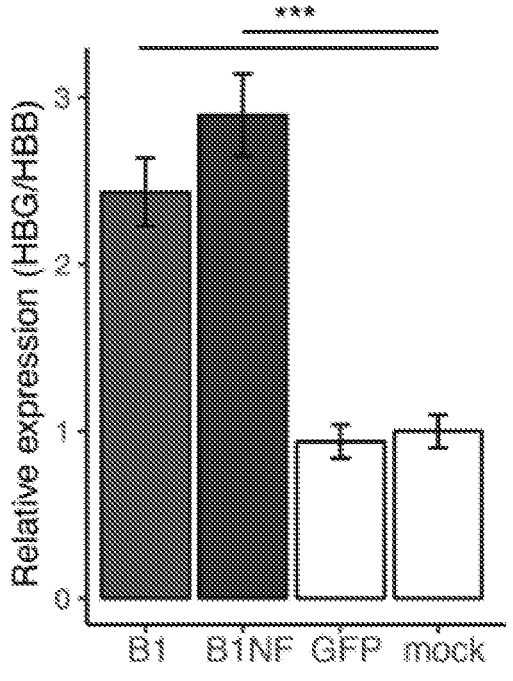
Figure 1C:
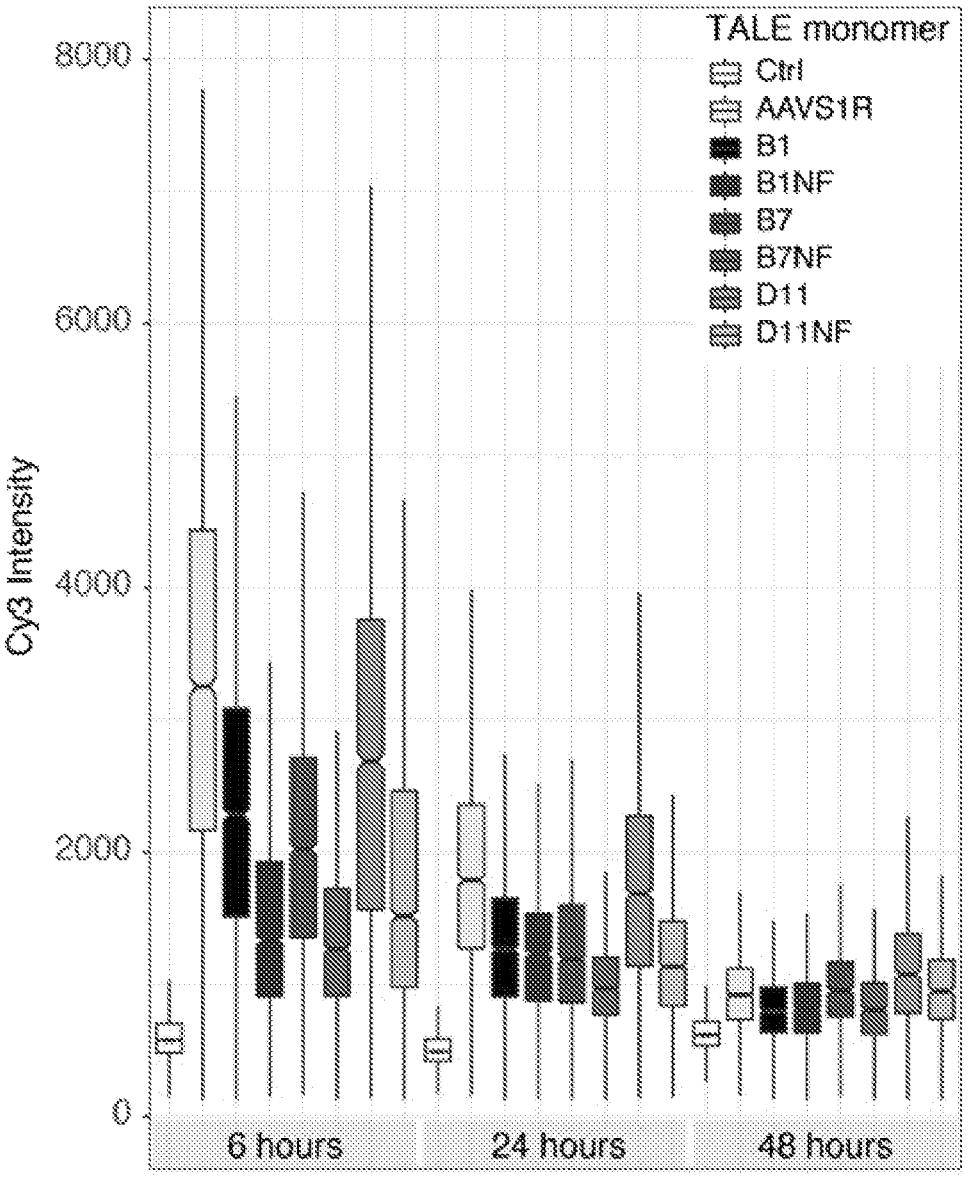
Figure 1D:
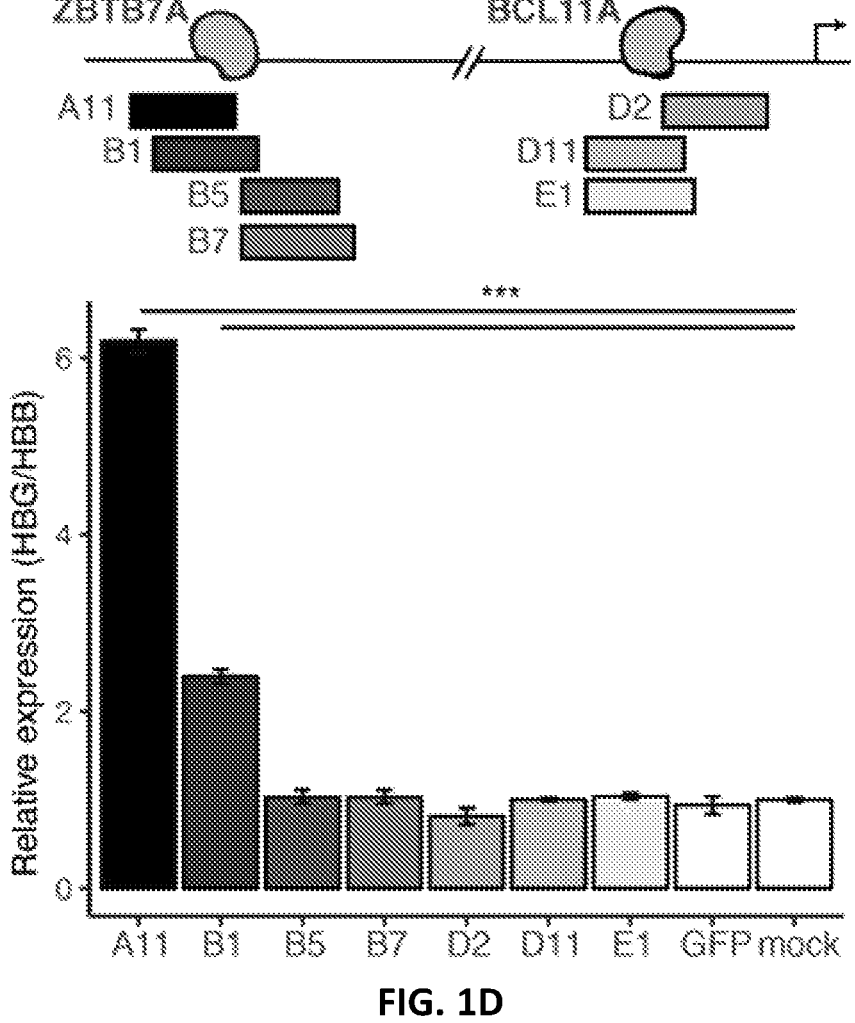
Figure 2A:
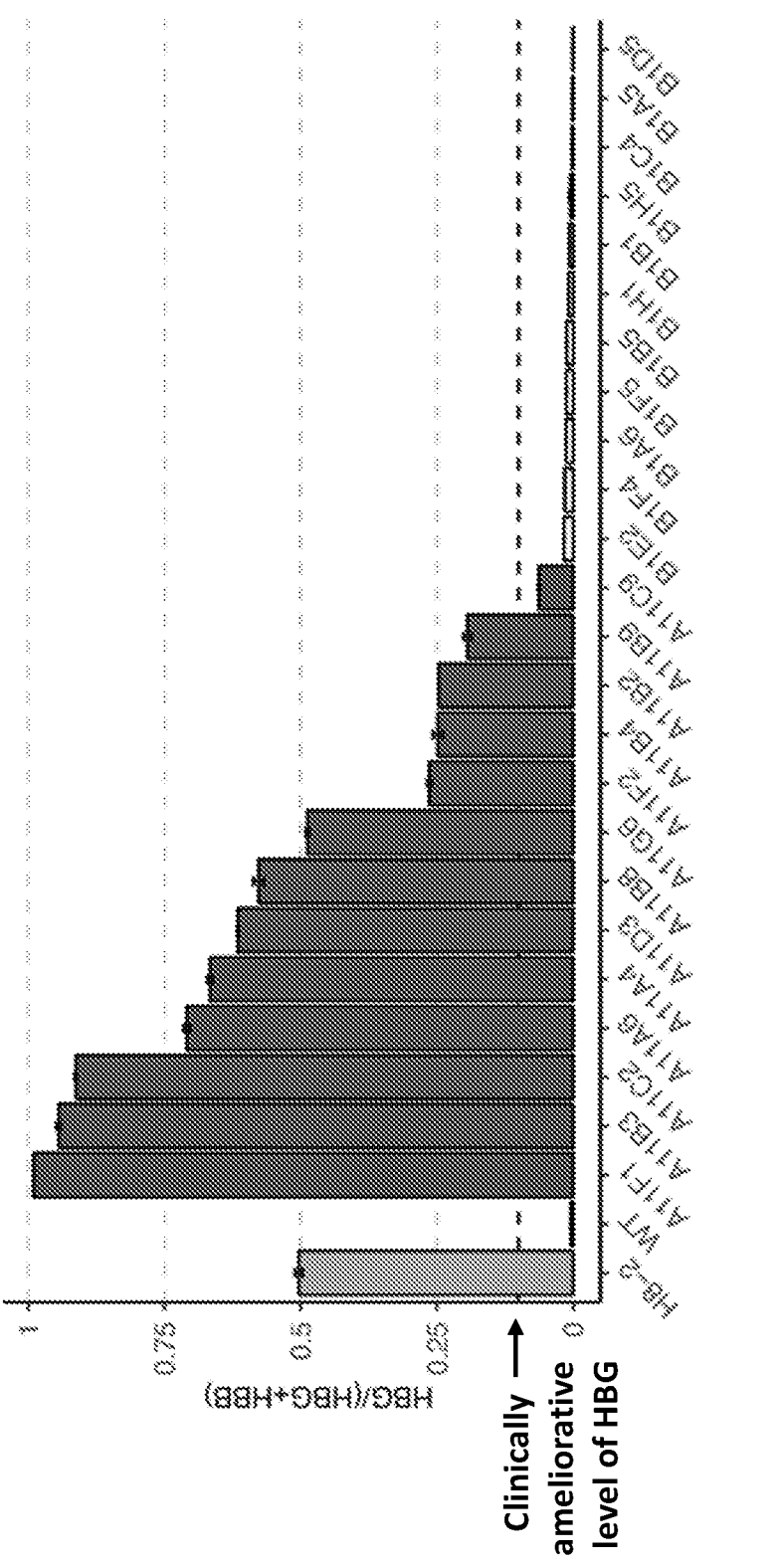
FIGS. 2A-2D. Stable expression of the A11 TALE results in globin switching at the RNA and protein level.
Figure 2B:
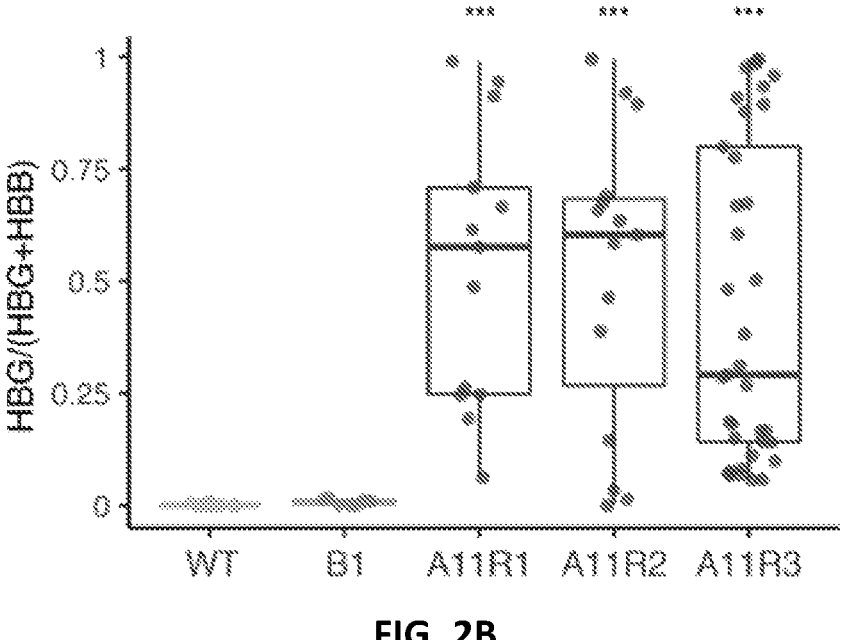
Figure 2C:
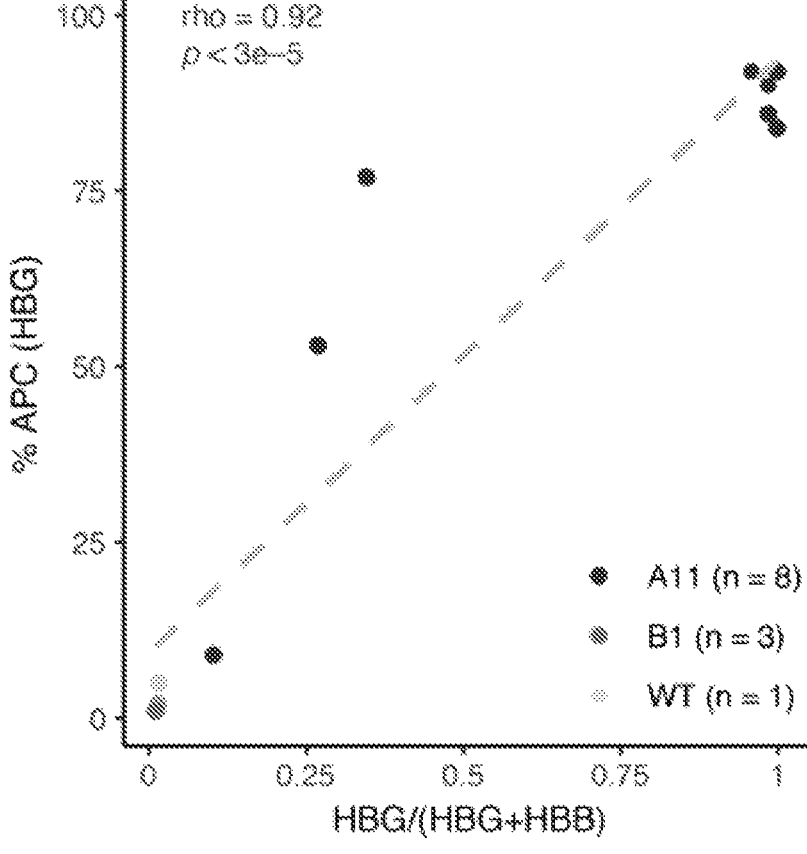
Figure 2D:
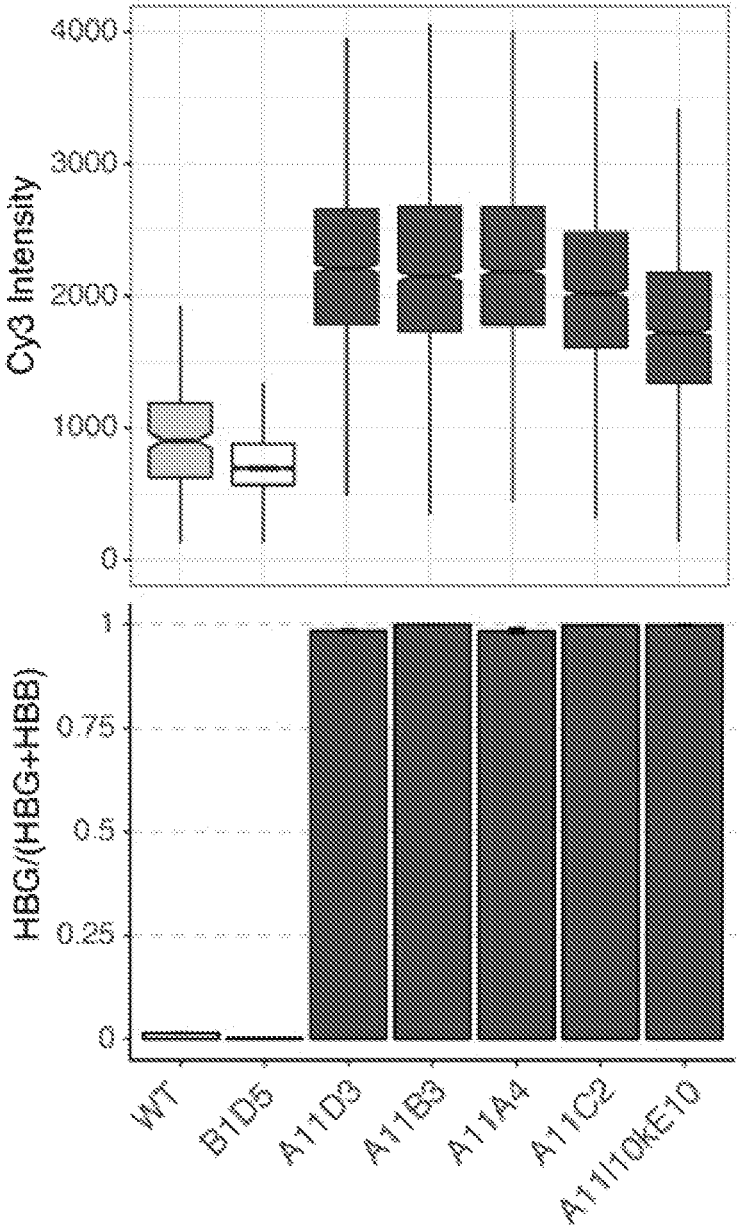

A11 and B1 TALEs induced increase in relative expression of HBG as compared to total hemoglobin (adult hemoglobin (HBB)+HBG). FIG. 1D.

Presence of an effector domain such as a cleavage domain (e.g., FokI) did not result in a significant difference in activity. FIGS. 1A-1B. TALEs that replaced the TF BCL11A has no significant effect on HBG expression.

HUDEP-2 cell lines expressing A11 TALE resulted in globin switching at the RNA and protein levels. FIGS. 2A-2D.

Figure 3:
FIG. 3. Cassette for expression of TALE designed for integration into the AAVS1 safe harbor locus.

FIG. 3. Cassette for expression of TALE designed for integration into the AAVS1 safe harbor locus.

Figure 4:
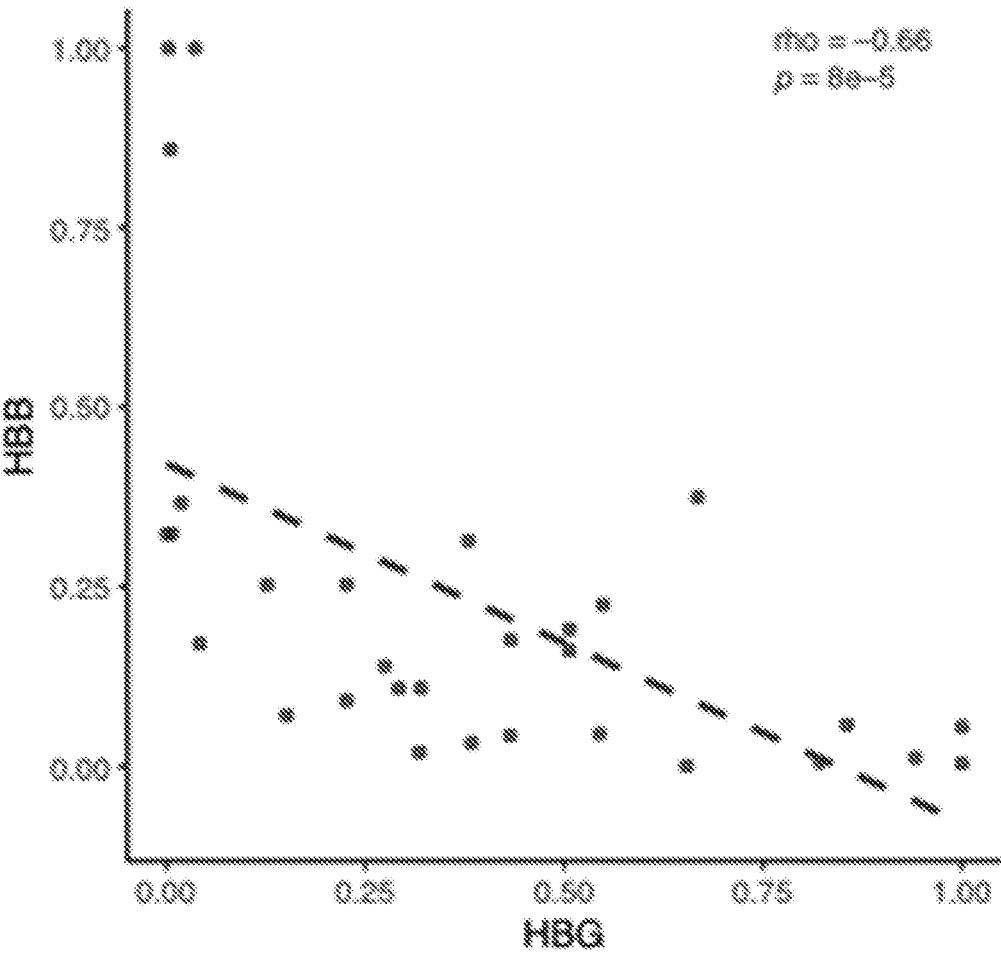
FIG. 4. Increased expression of HBG is accompanied by a decreased expression of HBB.

FIG. 4. Increased expression of HBG is accompanied by a decreased expression of HBB. This observation is surprising as it has not been previously reported that switching on the expression of HBG has an effect on the expression of HBB. The decreased expression of HBB may be beneficial as only low levels of HBG would be needed to provide functional Hb as compared to other therapeutic strategies that intend to provide high levels of HBG to compete with the HBB expressed a patient.

For reasons of completeness, certain aspects of the polypeptides, composition, and methods of the present disclosure are set out in the following numbered clauses:

1. A method for modulating expression of a gene in a cell, the method comprising introducing into the cell a DNA binding polypeptide (DBP) that binds a sequence in regulatory region of a gene bound by a transcription factor (TF), thereby displacing the TF and modulating expression of the gene.

2. The method of clause 1, wherein the sequence is a sequence that has previously been identified as being associated with activity of the TF based on reduced activity of the TF when the sequence includes a single nucleotide polymorphism (SNP) or a mutation.

3. The method of clause 2, wherein the sequence includes a mutation, wherein the mutation is a deletion, insertion, or substitution.

4. The method of any one of clauses 1-3, wherein the DBP binds to at least a 12 nucleotides long sequence comprising the sequence.

5. The method of any one of clauses 1-4, wherein the TF is a transcriptional activator and the introducing results in reduced expression of the gene.

6. The method of any one of clauses 1-4, wherein the TF is a transcriptional repressor and the introducing results in increased expression of the gene.

7. The method of any one of clauses 1-5, wherein the DBP is introduced as a nucleic acid encoding the DBP.

8. The method of clause 7, wherein the nucleic acid is a deoxyribonucleic acid (DNA).

9. The method of clause 7, wherein the nucleic acid is a ribonucleic acid (RNA).

10. The method of any one of clauses 7-9, wherein the sequence of the nucleic acid is codon optimized for expression in a human cell.

11. The method of any one of clauses 1-10, wherein the cell is a human cell.

12. The method of any one of clauses 1-11, wherein the cell is a cancer cell.

13. The method of any one of clauses 1-12, wherein the cell is an ex vivo cell.

14. The method of any one of clauses 1-12, wherein the introducing comprises administering the polypeptide or a nucleic acid encoding the polypeptide to a subject.

15. The method of clause 14, wherein the administering comprises parenteral administration.

16. The method of clause 14, wherein the administering comprises intravenous, intramuscular, intrathecal, or subcutaneous administration.

17. A recombinant DNA binding polypeptide (DBP) comprising a plurality of repeat units (RUs) ordered from N-terminus to C-terminus of the DBP to bind to a nucleic acid sequence in the fetal γ-globin gene promoter, wherein the nucleic acid sequence comprises a sequence bound by the transcription factor (TF) ZBTB7A, wherein each of the RU comprises the sequence $X_{1-11}X_{12}X_{13}X_{14-33,\ 34,\ or\ 35}$ (SEQ ID NO: 4), wherein:

$X_{1-11}$ is a chain of 11 contiguous amino acids, $X_{14-33\ or\ 34\ or\ 35}$ is a chain of 20, 21 or 22 contiguous amino acids, $X_{12}X_{13}$ is selected from:

(a) NH, HH, KH, NK, NQ, RH, RN, SS, NN, SN, or KN for recognition of guanine (G);

(b) NI, KI, RI, HI, or SI for recognition of adenine (A);

(c) NG, HG, KG, or RG for recognition of thymine (T);

(d) HD, RD, SD, ND, KD, or YG for recognition of cytosine (C); and (e) NV or HN for recognition of A or G; and (f) H*, HA, KA, N*, NA, NC, NS, RA, or S* for recognition of A or T or G or C, wherein (*) means that the amino acid at $X_{13}$ is absent, wherein the DBP displaces the TF from the fetal γ-globin gene promoter and results in expression of fetal hemoglobin-γ (HBG) from the fetal γ-globin gene.

18. The recombinant DBP of clause 17, wherein the DBP comprises a half-repeat comprising the amino acid sequence $X_{1-11}X_{12}X_{13}X_{14-19,\ 20,\ or\ 21}$ (SEQ ID NO: 5), wherein:

$X_{1-11}$ is a chain of 11 contiguous amino acids, $X_{14-20\ or\ 21\ or\ 22}$ is a chain of 7, 8 or 9 contiguous amino acids, $X_{12}X_{13}$ is selected from:

(a) NH, HH, KH, NK, NQ, RH, RN, SS, NN, SN, or KN for recognition of guanine (G);

(b) NI, KI, RI, HI, or SI for recognition of adenine (A);

(c) NG, HG, KG, or RG for recognition of thymine (T);

(d) HD, RD, SD, ND, KD, or YG for recognition of cytosine (C); and (e) NV or HN for recognition of A or G; and (f) H*, HA, KA, N*, NA, NC, NS, RA, or S* for recognition of A or T or G or C, wherein (*) means that the amino acid at $X_{13}$ is absent, wherein the half-repeat is present after the last RU.

19. The recombinant DBP of clause 17 or 18, wherein the DBP comprises RUs that binds to the nucleotide sequence: CCTCTTGGGGGCCCC (SEQ ID NO: 1).

20. The recombinant DBP of clause 19, wherein the $X_{12}X_{13}$ in the RUs from N-terminus to C-terminus are HD, HD, NG, HD, NG, NG, NH, NH, NH, NH, NH, HD, HD, HD, and HD, wherein the last RU is a half-RU.

21. The recombinant DBP of clause 17 or 18, wherein the DBP comprises RUs that bind to the nucleotide sequence: ATCCTCTTGGGGGCCCC (SEQ ID NO: 3).

22. The recombinant DBP of clause 20, wherein the $X_{12}X_{13}$ in the RUs from N-terminus to C-terminus are NI, NG, HD, HD, NG, HD, NG, NG, NH, NH, NH, NH, NH, HD, HD, HD, and HD, wherein the last RU is a half-RU.

23. The recombinant DBP of clause 17 or 18, wherein the nucleic acid sequence comprises RUs that bind to the nucleotide sequence: CCTCTTGGGGGCCCCTTCCC (SEQ ID NO: 3).

24. The recombinant DBP of clause 23, wherein the $X_{12}X_{13}$ in the RUs from N-terminus to C-terminus are HD, HD, NG, HD, NG, NG, NH, NH, NH, NH, NH, HD, HD, HD, HD, NG, NG, HD, HD, and HD, wherein the last RU is a half-RU.

25. The recombinant DBP of any one of clauses 17-24, wherein $X_{1-11}$ is at least 80% identical to LTPEQVVA-IAS (SEQ ID NO: 6).

26. The recombinant DBP of any one of clauses 17-24, wherein $X_{1-11}$ is at least 80% identical to LTPDQVVA-IAS (SEQ ID NO: 11).

27. The recombinant DBP of any one of clauses 17-26, wherein the chain of 20, 21, or 22 contiguous amino acids is at least 80% identical to GGKQALETVQRLLPVLCQDHG (SEQ ID NO: 15).

28. The recombinant DBP of any one of clauses 17-26, wherein the chain of 7, 8 or 9 contiguous amino acids is at least 80% identical to GGRPALE (SEQ ID NO: 7).

29. A nucleic acid encoding the recombinant DBP of any of clauses 17-28.

30. The nucleic acid of clause 29, wherein the nucleic acid is operably linked to a promoter sequence that confers expression of the DBP.

31. The nucleic acid of clause 29 or 30, wherein the sequence of the nucleic acid is codon optimized for expression of the DBP in a human cell.

32. The nucleic acid of any one of clauses 29-31, wherein the nucleic acid is a deoxyribonucleic acid (DNA).

33. The nucleic acid of any one of clauses 29-31, wherein the nucleic acid is a ribonucleic acid (RNA).

34. A vector comprising the nucleic acid of any of clauses 29-33.

35. The vector of clause 34, wherein the vector is a viral vector.

36. A host cell comprising the nucleic acid of any of clauses 29-33 or the vector of clause 34 or 35.

37. A host cell that expresses the DBP of any of clauses 1-28.

38. The host cell of clause 36 or 37, wherein the host cell is a human cell.

39. The host cell of any one of clauses 36-38, wherein the cell is a cancer cell.

40. The host cell of any one of clauses 36-39, wherein the cell is an ex vivo cell.

41. The host cell of any one of clauses 36-38, wherein the cell is present in a subject.

42. The host cell of any one of clauses 36-41, wherein the cell is a hematopoietic progenitor cell.

43. The host cell of any one of clauses 36-41, wherein the cell is an erythroid progenitor.

44. The host cell of any one of clauses 36-41, wherein the cell is a pluripotent stem cell.

45. The host cell of any one of clauses 36-41, wherein the cell is an induced pluripotent stem cell.

46. A pharmaceutical composition comprising the DBP of any of clauses 17-28 and a pharmaceutically acceptable excipient.

47. A pharmaceutical composition comprising the nucleic acid of any of clauses 29-33 or the vector of clause 34 or 35 and a pharmaceutically acceptable excipient.

48. A pharmaceutical composition comprising the host cell of any one of clauses 36-45.

49. A method for increasing expression of fetal hemoglobin-g (HBG) in a subject in need thereof, the method comprising administering to the subject the pharmaceutical composition of any one of clauses 46-48.

50. The method of clause 49, wherein the subject has sickle cell anemia.

51. The method of clause 49, wherein the subject has thalassemia.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular aspects only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A nucleic acid encoding a recombinant DNA binding polypeptide (DBP) comprising a plurality of repeat units (RUs) ordered from N-terminus to C-terminus of the DBP to bind to a nucleic acid sequence in the fetal y-globin gene promoter, wherein the sequence is

```
                                    (SEQ ID NO: 1)
CCTCTTGGGGGCCCC
or (SEQ ID NO: 2)
ATCCTCTTGGGGGCCCC,
``` wherein each of the RU comprises the amino acid sequence $X_{1-11}X_{12}X_{13}X_{14-33, 34, \text{ or } 35}$ (SEQ ID NO: 4), wherein:

$X_{1-11}$ is a chain of 11 contiguous amino acids, $X_{14-33 \text{ or } 34 \text{ or } 35}$ is a chain of 20, 21 or 22 contiguous amino acids, $X_{12}X_{13}$ is selected from:

(a) NH, HH, KH, NK, NQ, RH, RN, SS, NN, SN, or KN for recognition of guanine (G);

(b) NI, KI, RI, HI, or SI for recognition of adenine (A);

(c) NG, HG, KG, or RG for recognition of thymine (T);

(d) HD, RD, SD, ND, KD, or YG for recognition of cytosine (C); and (e) NV or HN for recognition of A or G; and (f)H*, HA, KA, N*, NA, NC, NS, RA, or S* for recognition of A or T or G or C, wherein (*) means that the amino acid at $X_{13}$ is absent, wherein the DBP is not fused to a functional domain having cleavage activity, wherein the DBP is not fused to a functional domain having transcriptional activation activity, and wherein binding of the DBP to the fetal γ-globin gene promoter results in expression of fetal hemoglobin-γ (HBG) from the fetal γ-globin gene.

2. The nucleic acid of claim 1, wherein the $X_{12}X_{13}$ in the RUs from N-terminus to C-terminus are HD, HD, NG, HD, NG, NG, NH, NH, NH, NH, NH, HD, HD, HD, and HD, wherein the last RU is a half-RU.

3. The nucleic acid of claim 1, wherein the DBP binds to the nucleic acid sequence: ATCCTCTTGGGGGCCCC (SEQ ID NO: 2).

4. The nucleic acid of claim 3, wherein the $X_{12}X_{13}$ in the RUs from N-terminus to C-terminus are NI, NG, HD, HD, NG, HD, NG, NG, NH, NH, NH, NH, NH, HD, HD, HD, and HD, wherein the last RU is a half-RU.

5. The nucleic acid of claim 1, wherein the DBP binds to the nucleic acid sequence: CCTCTTGGGGGCCCCTTCCC (SEQ ID NO: 3).

6. The nucleic acid of claim 5, wherein the $X_{12}X_{13}$ in the RUs from N-terminus to C-terminus are HD, HD, NG, HD, NG, NG, NH, NH, NH, NH, NH, HD, HD, HD, HD, NG, NG, HD, HD, and HD, wherein the last RU is a half-RU.

7. The nucleic acid of claim 1, wherein $X_{1-11}$ is at least 80% identical to LTPEQVVAIAS (SEQ ID NO: 6), LTPAQVVAIAS (SEQ ID NO: 9), LTPDQVVAIAN (SEQ ID NO: 10), LTPDQVVAIAS (SEQ ID NO: 11), LTPYQVVAIAS (SEQ ID NO: 12), LTREQVVAIAS (SEQ ID NO: 13), or LSTAQVVA-IAS (SEQ ID NO: 14), and the chain of 20, 21, or 22 contiguous amino acids is at least 80% identical to GGKQALETVQRLLPVLCQDHG (SEQ ID NO: 15), GGKQALATVQRLLPVLCQDHG (SEQ ID NO: 16), GGKQALETVQRVLPVLCQDHG (SEQ ID NO: 17.

8. The nucleic acid of claim 7, wherein the DBP protein comprises an N-terminal domain comprising an amino acid sequence having at least 80% sequence identity to any one of SEQ ID NOs: 150, 18, 19, or 20, and wherein the chain of 7, 8 or 9 contiguous amino acids is at least 80% identical to GGRPALE (SEQ ID NO: 7).

9. The nucleic acid of claim 1, wherein the nucleic acid is operably linked to a promoter sequence that confers expression of the DBP or wherein the sequence of the nucleic acid is codon optimized for expression of the DBP in a human cell.

10. The nucleic acid of claim 1, wherein the nucleic acid is a deoxyribonucleic acid (DNA).

11. The nucleic acid of claim 1, wherein the nucleic acid is a ribonucleic acid (RNA).

12. A viral vector comprising the nucleic acid of claim 1.

13. A host cell that comprises the nucleic acid of claim 1 and expresses the DBP.

14. The host cell of claim 13, wherein the cell is a pluripotent stem cell, an induced pluripotent stem cell, a hematopoietic progenitor cell, or an erythroid progenitor.

15. A pharmaceutical composition comprising the nucleic acid of claim 1 and a pharmaceutically acceptable excipient.

16. A pharmaceutical composition comprising the host cell of claim 14.

17. A method for increasing expression of fetal hemoglobin-γ (HBG) in a subject in need thereof, the method comprising administering to the subject the pharmaceutical composition of claim 16, wherein the subject has sickle cell anemia or thalassemia.

18. The nucleic acid of claim 1, wherein the nucleic acid sequence in the fetal γ-globin gene promoter bound by the DBP comprises a 5' T.

19. The nucleic acid of claim 1, wherein the DBP comprises an amino acid sequence having at least 90% sequence identity to SEQ ID NO:156.

20. The nucleic acid of claim 8, wherein the nucleic acid sequence in the fetal γ-globin gene promoter bound by the DBP comprises a 5' T.

* * * * *

SEQUENCE LISTING

```
<160> NUMBER OF SEQ ID NOS: 157

<210> SEQ ID NO 1
<211> LENGTH: 15
<212> TYPE: DNA
<213> ORGANISM: Artificial sequence
<220> FEATURE:
<223> OTHER INFORMATION: synthetic sequence

<400> SEQUENCE: 1
cctcttgggg gcccc                                              15

<210> SEQ ID NO 2
<211> LENGTH: 17
<212> TYPE: DNA
<213> ORGANISM: Artificial sequence
<220> FEATURE:
<223> OTHER INFORMATION: synthetic sequence

<400> SEQUENCE: 2
atcctcttgg gggcccc                                           17

<210> SEQ ID NO 3
<211> LENGTH: 20
<212> TYPE: DNA
```

-continued

```
<213> ORGANISM: Artificial sequence
<220> FEATURE:
<223> OTHER INFORMATION: synthetic sequence

<400> SEQUENCE: 3
cctcttgggg gccccttccc                                                    20

<210> SEQ ID NO 4
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: X is a chain of 11 contiguous amino acids
<220> FEATURE:
<221> NAME/KEY: MISC_FEATURE
<222> LOCATION: (2)..(3)
<223> OTHER INFORMATION: XX is selected from NH, HH, KH, NK, NQ, RH, RN,
      SS, NN, SN, KN NI, KI, RI, HI, SI, NG, HG, KG, RG HD, RD, SD, ND,
      KD, YG, NV, HN, H, HA, KA, N, NA, NC, NS, RA or S
<220> FEATURE:
<221> NAME/KEY: MISC_FEATURE
<222> LOCATION: (4)..(4)
<223> OTHER INFORMATION: X is a chain of 20, 21 or 22 contiguous amino
      acids

<400> SEQUENCE: 4

Xaa Xaa Xaa Xaa
1

<210> SEQ ID NO 5
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: XX iis a chain of 11 contiguous amino acids
<220> FEATURE:
<221> NAME/KEY: MISC_FEATURE
<222> LOCATION: (2)..(3)
<223> OTHER INFORMATION: XX is selected from NH, HH, KH, NK, NQ, RH, RN,
      SS, NN, SN, KN NI, KI, RI, HI, SI, NG, HG, KG, RG HD, RD, SD, ND,
      KD, YG, NV, HN, H, HA, KA, N, NA, NC, NS, RA or S
<220> FEATURE:
<221> NAME/KEY: MISC_FEATURE
<222> LOCATION: (4)..(4)
<223> OTHER INFORMATION: X is a chain of 7, 8 or 9 contiguous amino
      acids

<400> SEQUENCE: 5

Xaa Xaa Xaa Xaa
1

<210> SEQ ID NO 6
<211> LENGTH: 11
<212> TYPE: PRT
<213> ORGANISM: Artificial sequence
<220> FEATURE:
<223> OTHER INFORMATION: synthetic sequence

<400> SEQUENCE: 6

Leu Thr Pro Glu Gln Val Val Ala Ile Ala Ser
1               5                   10

<210> SEQ ID NO 7
```

```
<211> LENGTH: 7
<212> TYPE: PRT
<213> ORGANISM: Artificial sequence
<220> FEATURE:
<223> OTHER INFORMATION: synthetic sequence

<400> SEQUENCE: 7

Gly Gly Arg Pro Ala Leu Glu
1               5

<210> SEQ ID NO 8
<211> LENGTH: 33
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (12)..(13)
<223> OTHER INFORMATION: XX is HH, KH, NH, NK, NQ, RH, RN, SS, NN, SN,
      KN, NI, KI, RI, HI, SI, NG, HG, KG, RG, RD, SD, HD, ND, KD, YG,
      YK, NV, HN, H, HA, KA, N, NA, NC, NS, RA, CI, or S

<400> SEQUENCE: 8

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Gln Asp His
            20                  25                  30

Gly

<210> SEQ ID NO 9
<211> LENGTH: 11
<212> TYPE: PRT
<213> ORGANISM: Artificial sequence
<220> FEATURE:
<223> OTHER INFORMATION: synthetic sequence

<400> SEQUENCE: 9

Leu Thr Pro Ala Gln Val Val Ala Ile Ala Ser
1               5                   10

<210> SEQ ID NO 10
<211> LENGTH: 11
<212> TYPE: PRT
<213> ORGANISM: Artificial sequence
<220> FEATURE:
<223> OTHER INFORMATION: synthetic sequence

<400> SEQUENCE: 10

Leu Thr Pro Asp Gln Val Val Ala Ile Ala Asn
1               5                   10

<210> SEQ ID NO 11
<211> LENGTH: 11
<212> TYPE: PRT
<213> ORGANISM: Artificial sequence
<220> FEATURE:
<223> OTHER INFORMATION: synthetic sequence

<400> SEQUENCE: 11

Leu Thr Pro Asp Gln Val Val Ala Ile Ala Ser
1               5                   10

<210> SEQ ID NO 12
<211> LENGTH: 11
<212> TYPE: PRT
<213> ORGANISM: Artificial sequence
```

-continued

```
<220> FEATURE:
<223> OTHER INFORMATION: synthetic sequence

<400> SEQUENCE: 12

Leu Thr Pro Tyr Gln Val Val Ala Ile Ala Ser
1               5                   10

<210> SEQ ID NO 13
<211> LENGTH: 11
<212> TYPE: PRT
<213> ORGANISM: Artificial sequence
<220> FEATURE:
<223> OTHER INFORMATION: synthetic sequence

<400> SEQUENCE: 13

Leu Thr Arg Glu Gln Val Val Ala Ile Ala Ser
1               5                   10

<210> SEQ ID NO 14
<211> LENGTH: 11
<212> TYPE: PRT
<213> ORGANISM: Artificial sequence
<220> FEATURE:
<223> OTHER INFORMATION: synthetic sequence

<400> SEQUENCE: 14

Leu Ser Thr Ala Gln Val Val Ala Ile Ala Ser
1               5                   10

<210> SEQ ID NO 15
<211> LENGTH: 21
<212> TYPE: PRT
<213> ORGANISM: Artificial sequence
<220> FEATURE:
<223> OTHER INFORMATION: synthetic sequence

<400> SEQUENCE: 15

Gly Gly Lys Gln Ala Leu Glu Thr Val Gln Arg Leu Leu Pro Val Leu
1               5                   10                  15

Cys Gln Asp His Gly
            20

<210> SEQ ID NO 16
<211> LENGTH: 21
<212> TYPE: PRT
<213> ORGANISM: Artificial sequence
<220> FEATURE:
<223> OTHER INFORMATION: synthetic sequence

<400> SEQUENCE: 16

Gly Gly Lys Gln Ala Leu Ala Thr Val Gln Arg Leu Leu Pro Val Leu
1               5                   10                  15

Cys Gln Asp His Gly
            20

<210> SEQ ID NO 17
<211> LENGTH: 21
<212> TYPE: PRT
<213> ORGANISM: Artificial sequence
<220> FEATURE:
<223> OTHER INFORMATION: synthetic sequence

<400> SEQUENCE: 17

Gly Gly Lys Gln Ala Leu Glu Thr Val Gln Arg Val Leu Pro Val Leu
1               5                   10                  15
```

-continued

```
Cys Gln Asp His Gly
            20

<210> SEQ ID NO 18
<211> LENGTH: 120
<212> TYPE: PRT
<213> ORGANISM: Xanthomonas spp

<400> SEQUENCE: 18

Lys Pro Lys Val Arg Ser Thr Val Ala Gln His His Glu Ala Leu Val
1               5                   10                  15

Gly His Gly Phe Thr His Ala His Ile Val Ala Leu Ser Gln His Pro
            20                  25                  30

Ala Ala Leu Gly Thr Val Ala Val Lys Tyr Gln Asp Met Ile Ala Ala
        35                  40                  45

Leu Pro Glu Ala Thr His Glu Ala Ile Val Gly Val Gly Lys Gln Trp
    50                  55                  60

Ser Gly Ala Arg Ala Leu Glu Ala Leu Leu Thr Val Ala Gly Glu Leu
65                  70                  75                  80

Arg Gly Pro Pro Leu Gln Leu Asp Thr Gly Gln Leu Leu Lys Ile Ala
                85                  90                  95

Lys Arg Gly Gly Val Thr Ala Val Glu Ala Val His Ala Trp Arg Asn
            100                 105                 110

Ala Leu Thr Gly Ala Pro Leu Asn
        115                 120

<210> SEQ ID NO 19
<211> LENGTH: 115
<212> TYPE: PRT
<213> ORGANISM: Xanthomonas spp

<400> SEQUENCE: 19

Ser Thr Val Ala Gln His His Glu Ala Leu Val Gly His Gly Phe Thr
1               5                   10                  15

His Ala His Ile Val Ala Leu Ser Gln His Pro Ala Ala Leu Gly Thr
            20                  25                  30

Val Ala Val Lys Tyr Gln Asp Met Ile Ala Ala Leu Pro Glu Ala Thr
        35                  40                  45

His Glu Ala Ile Val Gly Val Gly Lys Gln Trp Ser Gly Ala Arg Ala
    50                  55                  60

Leu Glu Ala Leu Leu Thr Val Ala Gly Glu Leu Arg Gly Pro Pro Leu
65                  70                  75                  80

Gln Leu Asp Thr Gly Gln Leu Leu Lys Ile Ala Lys Arg Gly Gly Val
                85                  90                  95

Thr Ala Val Glu Ala Val His Ala Trp Arg Asn Ala Leu Thr Gly Ala
            100                 105                 110

Pro Leu Asn
        115

<210> SEQ ID NO 20
<211> LENGTH: 110
<212> TYPE: PRT
<213> ORGANISM: Xanthomonas spp

<400> SEQUENCE: 20

His His Glu Ala Leu Val Gly His Gly Phe Thr His Ala His Ile Val
1               5                   10                  15

Ala Leu Ser Gln His Pro Ala Ala Leu Gly Thr Val Ala Val Lys Tyr
```

-continued

```
                20                25                30

Gln Asp Met Ile Ala Ala Leu Pro Glu Ala Thr His Glu Ala Ile Val
            35                40                45

Gly Val Gly Lys Gln Trp Ser Gly Ala Arg Ala Leu Glu Ala Leu Leu
        50                55                60

Thr Val Ala Gly Glu Leu Arg Gly Pro Pro Leu Gln Leu Asp Thr Gly
65                70                75                80

Gln Leu Leu Lys Ile Ala Lys Arg Gly Gly Val Thr Ala Val Glu Ala
                    85                90                95

Val His Ala Trp Arg Asn Ala Leu Thr Gly Ala Pro Leu Asn
                100                105                110

<210> SEQ ID NO 21
<211> LENGTH: 34
<212> TYPE: PRT
<213> ORGANISM: Xanthomonas spp

<400> SEQUENCE: 21

Leu Thr Pro Asp Gln Val Val Ala Ile Ala Ser Asn His Gly Gly Lys
1                5                10                15

Gln Ala Leu Glu Thr Val Gln Arg Leu Leu Pro Val Leu Cys Gln Asp
            20                25                30

His Gly

<210> SEQ ID NO 22
<211> LENGTH: 34
<212> TYPE: PRT
<213> ORGANISM: Xanthomonas spp

<400> SEQUENCE: 22

Leu Thr Pro Asp Gln Val Val Ala Ile Ala Ser Asn Gly Gly Gly Lys
1                5                10                15

Gln Ala Leu Glu Thr Val Gln Arg Leu Leu Pro Val Leu Cys Gln Asp
            20                25                30

His Gly

<210> SEQ ID NO 23
<211> LENGTH: 34
<212> TYPE: PRT
<213> ORGANISM: Xanthomonas spp

<400> SEQUENCE: 23

Leu Thr Pro Asp Gln Val Val Ala Ile Ala Ser Asn Ile Gly Gly Lys
1                5                10                15

Gln Ala Leu Glu Thr Val Gln Arg Leu Leu Pro Val Leu Cys Gln Asp
            20                25                30

His Gly

<210> SEQ ID NO 24
<211> LENGTH: 34
<212> TYPE: PRT
<213> ORGANISM: Xanthomonas spp

<400> SEQUENCE: 24

Leu Thr Pro Asp Gln Val Val Ala Ile Ala Ser His Asp Gly Gly Lys
1                5                10                15

Gln Ala Leu Glu Thr Val Gln Arg Leu Leu Pro Val Leu Cys Gln Asp
            20                25                30
```

-continued

```
His Gly

<210> SEQ ID NO 25
<211> LENGTH: 4
<212> TYPE: PRT
<213> ORGANISM: Ralstonia solanacearum
<220> FEATURE:
<221> NAME/KEY: MISC_FEATURE
<222> LOCATION: (1)..(1)
<223> OTHER INFORMATION: X is a chain of 11 contiguous amino acids
<220> FEATURE:
<221> NAME/KEY: MISC_FEATURE
<222> LOCATION: (2)..(3)
<223> OTHER INFORMATION: XX is selected from NH, HH, KH, NK, NQ, RH, RN,
      SS, NN, SN, KN NI, KI, RI, HI, SI, NG, HG, KG, RG HD, RD, SD, ND,
      KD, YG, NV, HN, H, HA, KA, N, NA, NC, NS, RA or S
<220> FEATURE:
<221> NAME/KEY: MISC_FEATURE
<222> LOCATION: (4)..(4)
<223> OTHER INFORMATION: X is a chain of 20, 21 or 22 contiguous amino
      acids

<400> SEQUENCE: 25

Xaa Xaa Xaa Xaa
1

<210> SEQ ID NO 26
<211> LENGTH: 35
<212> TYPE: PRT
<213> ORGANISM: Ralstonia solanacearum

<400> SEQUENCE: 26

Leu Asp Thr Glu Gln Val Val Ala Ile Ala Ser His Asn Gly Gly Lys
1               5                   10                  15

Gln Ala Leu Glu Ala Val Lys Ala Asp Leu Leu Asp Leu Leu Gly Ala
            20                  25                  30

Pro Tyr Val
        35

<210> SEQ ID NO 27
<211> LENGTH: 35
<212> TYPE: PRT
<213> ORGANISM: Ralstonia solanacearum

<400> SEQUENCE: 27

Leu Asn Thr Glu Gln Val Val Ala Val Ala Ser Asn Lys Gly Gly Lys
1               5                   10                  15

Gln Ala Leu Glu Ala Val Gly Ala Gln Leu Leu Ala Leu Arg Ala Val
            20                  25                  30

Pro Tyr Glu
        35

<210> SEQ ID NO 28
<211> LENGTH: 35
<212> TYPE: PRT
<213> ORGANISM: Ralstonia solanacearum

<400> SEQUENCE: 28

Leu Ser Thr Ala Gln Val Ala Ala Ile Ala Ser His Asp Gly Gly Lys
1               5                   10                  15

Gln Ala Leu Glu Ala Val Gly Thr Gln Leu Val Val Leu Arg Ala Ala
            20                  25                  30

Pro Tyr Ala
        35
```

```
<210> SEQ ID NO 29
<211> LENGTH: 35
<212> TYPE: PRT
<213> ORGANISM: Ralstonia solanacearum

<400> SEQUENCE: 29

Leu Ser Thr Ala Gln Val Val Ala Val Ala Gly Arg Asn Gly Gly Lys
1               5                   10                  15

Gln Ala Leu Glu Ala Val Arg Ala Gln Leu Pro Ala Leu Arg Ala Ala
            20                  25                  30

Pro Tyr Gly
        35

<210> SEQ ID NO 30
<211> LENGTH: 35
<212> TYPE: PRT
<213> ORGANISM: Ralstonia solanacearum

<400> SEQUENCE: 30

Leu Ser Thr Ala Gln Val Val Ala Val Ala Ser Ser Asn Gly Gly Lys
1               5                   10                  15

Gln Ala Leu Glu Ala Val Trp Ala Leu Leu Pro Val Leu Arg Ala Thr
            20                  25                  30

Pro Tyr Asp
        35

<210> SEQ ID NO 31
<211> LENGTH: 137
<212> TYPE: PRT
<213> ORGANISM: Ralstonia solanacearum

<400> SEQUENCE: 31

Phe Gly Lys Leu Val Ala Leu Gly Tyr Ser Arg Glu Gln Ile Arg Lys
1               5                   10                  15

Leu Lys Gln Glu Ser Leu Ser Glu Ile Ala Lys Tyr His Thr Thr Leu
            20                  25                  30

Thr Gly Gln Gly Phe Thr His Ala Asp Ile Cys Arg Ile Ser Arg Arg
        35                  40                  45

Arg Gln Ser Leu Arg Val Val Ala Arg Asn Tyr Pro Glu Leu Ala Ala
    50                  55                  60

Ala Leu Pro Glu Leu Thr Arg Ala His Ile Val Asp Ile Ala Arg Gln
65                  70                  75                  80

Arg Ser Gly Asp Leu Ala Leu Gln Ala Leu Leu Pro Val Ala Thr Ala
            85                  90                  95

Leu Thr Ala Ala Pro Leu Arg Leu Ser Ala Ser Gln Ile Ala Thr Val
            100                 105                 110

Ala Gln Tyr Gly Glu Arg Pro Ala Ile Gln Ala Leu Tyr Arg Leu Arg
        115                 120                 125

Arg Lys Leu Thr Arg Ala Pro Leu His
    130                 135

<210> SEQ ID NO 32
<211> LENGTH: 120
<212> TYPE: PRT
<213> ORGANISM: Ralstonia solanacearum

<400> SEQUENCE: 32

Lys Gln Glu Ser Leu Ser Glu Ile Ala Lys Tyr His Thr Thr Leu Thr
1               5                   10                  15
```

-continued

```
Gly Gln Gly Phe Thr His Ala Asp Ile Cys Arg Ile Ser Arg Arg Arg
        20                  25                  30

Gln Ser Leu Arg Val Val Ala Arg Asn Tyr Pro Glu Leu Ala Ala Ala
        35                  40                  45

Leu Pro Glu Leu Thr Arg Ala His Ile Val Asp Ile Ala Arg Gln Arg
        50                  55                  60

Ser Gly Asp Leu Ala Leu Gln Ala Leu Leu Pro Val Ala Thr Ala Leu
65                  70                  75                  80

Thr Ala Ala Pro Leu Arg Leu Ser Ala Ser Gln Ile Ala Thr Val Ala
                85                  90                  95

Gln Tyr Gly Glu Arg Pro Ala Ile Gln Ala Leu Tyr Arg Leu Arg Arg
                100                 105                 110

Lys Leu Thr Arg Ala Pro Leu His
        115                 120

<210> SEQ ID NO 33
<211> LENGTH: 19
<212> TYPE: PRT
<213> ORGANISM: Ralstonia solanacearum

<400> SEQUENCE: 33

Leu Ser Thr Ala Gln Val Val Ala Ile Ala Cys Ile Ser Gly Gln Gln
1               5                   10                  15

Ala Leu Glu

<210> SEQ ID NO 34
<211> LENGTH: 62
<212> TYPE: PRT
<213> ORGANISM: Ralstonia solanacearum

<400> SEQUENCE: 34

Ala Ile Glu Ala His Met Pro Thr Leu Arg Gln Ala Ser His Ser Leu
1               5                   10                  15

Ser Pro Glu Arg Val Ala Ala Ile Ala Cys Ile Gly Gly Arg Ser Ala
                20                  25                  30

Val Glu Ala Val Arg Gln Gly Leu Pro Val Lys Ala Ile Arg Arg Ile
        35                  40                  45

Arg Arg Glu Lys Ala Pro Val Ala Gly Pro Pro Ala Ser
    50                  55                  60

<210> SEQ ID NO 35
<211> LENGTH: 115
<212> TYPE: PRT
<213> ORGANISM: Ralstonia solanacearum

<400> SEQUENCE: 35

Ser Glu Ile Ala Lys Tyr His Thr Thr Leu Thr Gly Gln Gly Phe Thr
1               5                   10                  15

His Ala Asp Ile Cys Arg Ile Ser Arg Arg Arg Gln Ser Leu Arg Val
            20                  25                  30

Val Ala Arg Asn Tyr Pro Glu Leu Ala Ala Ala Leu Pro Glu Leu Thr
        35                  40                  45

Arg Ala His Ile Val Asp Ile Ala Arg Gln Arg Ser Gly Asp Leu Ala
    50                  55                  60

Leu Gln Ala Leu Leu Pro Val Ala Thr Ala Leu Thr Ala Ala Pro Leu
65                  70                  75                  80

Arg Leu Ser Ala Ser Gln Ile Ala Thr Val Ala Gln Tyr Gly Glu Arg
```

-continued

```
                     85                   90                   95

Pro Ala Ile Gln Ala Leu Tyr Arg Leu Arg Arg Lys Leu Thr Arg Ala
           100                  105                  110

Pro Leu His
       115

<210> SEQ ID NO 36
<211> LENGTH: 4
<212> TYPE: PRT
<213> ORGANISM: Legionellales bacterium
<220> FEATURE:
<221> NAME/KEY: MISC_FEATURE
<222> LOCATION: (1)..(1)
<223> OTHER INFORMATION: X is a chain of 11 contiguous amino acids
<220> FEATURE:
<221> NAME/KEY: MISC_FEATURE
<222> LOCATION: (2)..(3)
<223> OTHER INFORMATION: XX is selected from NH, HH, KH, NK, NQ, RH, RN,
      SS, NN, SN, KN NI, KI, RI, HI, SI, NG, HG, KG, RG HD, RD, SD, ND,
      KD, YG, NV,
      HN, H, HA, KA, N, NA, NC, NS, RA or S
<220> FEATURE:
<221> NAME/KEY: MISC_FEATURE
<222> LOCATION: (4)..(4)
<223> OTHER INFORMATION: X is a chain of 20, 21 or 22 contiguous amino
      acids

<400> SEQUENCE: 36

Xaa Xaa Xaa Xaa
1

<210> SEQ ID NO 37
<211> LENGTH: 33
<212> TYPE: PRT
<213> ORGANISM: L. quateirensis

<400> SEQUENCE: 37

Phe Ser Ser Gln Gln Ile Ile Arg Met Val Ser His Ala Gly Gly Ala
1               5                   10                  15

Asn Asn Leu Lys Ala Val Thr Ala Asn His Asp Asp Leu Gln Asn Met
           20                  25                  30

Gly

<210> SEQ ID NO 38
<211> LENGTH: 33
<212> TYPE: PRT
<213> ORGANISM: L. quateirensis

<400> SEQUENCE: 38

Phe Asn Val Glu Gln Ile Val Arg Met Val Ser His Asn Gly Gly Ser
1               5                   10                  15

Lys Asn Leu Lys Ala Val Thr Asp Asn His Asp Asp Leu Lys Asn Met
           20                  25                  30

Gly

<210> SEQ ID NO 39
<211> LENGTH: 33
<212> TYPE: PRT
<213> ORGANISM: L. quateirensis

<400> SEQUENCE: 39

Phe Asn Ala Glu Gln Ile Val Arg Met Val Ser His Gly Gly Gly Ser
1               5                   10                  15

Lys Asn Leu Lys Ala Val Thr Asp Asn His Asp Asp Leu Lys Asn Met
```

-continued

```
            20                  25                  30

Gly

<210> SEQ ID NO 40
<211> LENGTH: 33
<212> TYPE: PRT
<213> ORGANISM: L. quateirensis

<400> SEQUENCE: 40

Phe Asn Ala Glu Gln Ile Val Ser Met Val Ser Asn Asn Gly Gly Ser
1               5                   10                  15

Lys Asn Leu Lys Ala Val Thr Asp Asn His Asp Asp Leu Lys Asn Met
            20                  25                  30

Gly

<210> SEQ ID NO 41
<211> LENGTH: 33
<212> TYPE: PRT
<213> ORGANISM: L. quateirensis

<400> SEQUENCE: 41

Phe Asn Ala Glu Gln Ile Val Ser Met Val Ser Asn Gly Gly Gly Ser
1               5                   10                  15

Leu Asn Leu Lys Ala Val Lys Lys Tyr His Asp Ala Leu Lys Asp Arg
            20                  25                  30

Gly

<210> SEQ ID NO 42
<211> LENGTH: 33
<212> TYPE: PRT
<213> ORGANISM: L. quateirensis

<400> SEQUENCE: 42

Phe Asn Thr Glu Gln Ile Val Arg Met Val Ser His Asp Gly Gly Ser
1               5                   10                  15

Leu Asn Leu Lys Ala Val Lys Lys Tyr His Asp Ala Leu Arg Glu Arg
            20                  25                  30

Lys

<210> SEQ ID NO 43
<211> LENGTH: 33
<212> TYPE: PRT
<213> ORGANISM: L. quateirensis

<400> SEQUENCE: 43

Phe Asn Val Glu Gln Ile Val Ser Ile Val Ser His Gly Gly Gly Ser
1               5                   10                  15

Leu Asn Leu Lys Ala Val Lys Lys Tyr His Asp Val Leu Lys Asp Arg
            20                  25                  30

Glu

<210> SEQ ID NO 44
<211> LENGTH: 33
<212> TYPE: PRT
<213> ORGANISM: L. quateirensis

<400> SEQUENCE: 44

Phe Asn Ala Glu Gln Ile Val Arg Met Val Ser His Asp Gly Gly Ser
1               5                   10                  15
```

-continued

```
Leu Asn Leu Lys Ala Val Thr Asp Asn His Asp Asp Leu Lys Asn Met
            20                  25                  30

Gly

<210> SEQ ID NO 45
<211> LENGTH: 33
<212> TYPE: PRT
<213> ORGANISM: L. maceachernii

<400> SEQUENCE: 45

Phe Ser Ala Glu Gln Ile Val Arg Ile Ala Ala His Asp Gly Gly Ser
1               5                   10                  15

Arg Asn Ile Glu Ala Val Gln Gln Ala Gln His Val Leu Lys Glu Leu
            20                  25                  30

Gly

<210> SEQ ID NO 46
<211> LENGTH: 33
<212> TYPE: PRT
<213> ORGANISM: L. maceachernii

<400> SEQUENCE: 46

Phe Ser Ala Glu Gln Ile Val Ser Ile Val Ala His Asp Gly Gly Ser
1               5                   10                  15

Arg Asn Ile Glu Ala Val Gln Gln Ala Gln His Ile Leu Lys Glu Leu
            20                  25                  30

Gly

<210> SEQ ID NO 47
<211> LENGTH: 33
<212> TYPE: PRT
<213> ORGANISM: Legionellales bacterium

<400> SEQUENCE: 47

Leu Asp Arg Gln Gln Ile Leu Arg Ile Ala Ser His Asp Gly Gly Ser
1               5                   10                  15

Lys Asn Ile Ala Ala Val Gln Lys Phe Leu Pro Lys Leu Met Asn Phe
            20                  25                  30

Gly

<210> SEQ ID NO 48
<211> LENGTH: 33
<212> TYPE: PRT
<213> ORGANISM: L. maceachernii

<400> SEQUENCE: 48

Phe Ser Ala Glu Gln Ile Val Arg Ile Ala Ala His Asp Gly Gly Ser
1               5                   10                  15

Leu Asn Ile Asp Ala Val Gln Gln Ala Gln Gln Ala Leu Lys Glu Leu
            20                  25                  30

Gly

<210> SEQ ID NO 49
<211> LENGTH: 33
<212> TYPE: PRT
<213> ORGANISM: L. maceachernii

<400> SEQUENCE: 49

Phe Ser Thr Glu Gln Ile Val Cys Ile Ala Gly His Gly Gly Gly Ser
1               5                   10                  15
```

-continued

---

```
Leu Asn Ile Lys Ala Val Leu Leu Ala Gln Gln Ala Leu Lys Asp Leu
            20                  25                  30

Gly

<210> SEQ ID NO 50
<211> LENGTH: 33
<212> TYPE: PRT
<213> ORGANISM: L. maceachernii

<400> SEQUENCE: 50

Tyr Ser Ser Glu Gln Ile Val Arg Val Ala Ala His Gly Gly Gly Ser
1               5                   10                  15

Leu Asn Ile Lys Ala Val Leu Gln Ala His Gln Ala Leu Lys Glu Leu
            20                  25                  30

Asp

<210> SEQ ID NO 51
<211> LENGTH: 33
<212> TYPE: PRT
<213> ORGANISM: L. maceachernii

<400> SEQUENCE: 51

Phe Ser Ala Glu Gln Ile Val His Ile Ala Ala His Gly Gly Gly Ser
1               5                   10                  15

Leu Asn Ile Lys Ala Ile Leu Gln Ala His Gln Thr Leu Lys Glu Leu
            20                  25                  30

Asn

<210> SEQ ID NO 52
<211> LENGTH: 33
<212> TYPE: PRT
<213> ORGANISM: L. maceachernii

<400> SEQUENCE: 52

Phe Ser Ala Glu Gln Ile Val Arg Ile Ala Ala His Ile Gly Gly Ser
1               5                   10                  15

Arg Asn Ile Glu Ala Ile Gln Gln Ala His His Ala Leu Lys Glu Leu
            20                  25                  30

Gly

<210> SEQ ID NO 53
<211> LENGTH: 33
<212> TYPE: PRT
<213> ORGANISM: L. maceachernii

<400> SEQUENCE: 53

Phe Ser Ala Glu Gln Ile Val Arg Ile Ala Ala His Ile Gly Gly Ser
1               5                   10                  15

His Asn Leu Lys Ala Val Leu Gln Ala Gln Gln Ala Leu Lys Glu Leu
            20                  25                  30

Asp

<210> SEQ ID NO 54
<211> LENGTH: 33
<212> TYPE: PRT
<213> ORGANISM: L. maceachernii

<400> SEQUENCE: 54

Phe Ser Ala Lys His Ile Val Arg Ile Ala Ala His Ile Gly Gly Ser
```

-continued

```
1               5               10              15

Leu Asn Ile Lys Ala Val Gln Gln Ala Gln Gln Ala Leu Lys Glu Leu
            20              25              30

Gly

<210> SEQ ID NO 55
<211> LENGTH: 33
<212> TYPE: PRT
<213> ORGANISM: L. quateirensis

<400> SEQUENCE: 55

Phe Asn Ala Glu Gln Ile Val Arg Met Val Ser His Lys Gly Gly Ser
1               5               10              15

Lys Asn Leu Ala Leu Val Lys Glu Tyr Phe Pro Val Phe Ser Ser Phe
            20              25              30

His

<210> SEQ ID NO 56
<211> LENGTH: 33
<212> TYPE: PRT
<213> ORGANISM: L. maceachernii

<400> SEQUENCE: 56

Phe Ser Ala Asp Gln Ile Val Arg Ile Ala Ala His Lys Gly Gly Ser
1               5               10              15

His Asn Ile Val Ala Val Gln Gln Ala Gln Gln Ala Leu Lys Glu Leu
            20              25              30

Asp

<210> SEQ ID NO 57
<211> LENGTH: 33
<212> TYPE: PRT
<213> ORGANISM: L. maceachernii

<400> SEQUENCE: 57

Phe Ser Ala Glu Gln Ile Val Ser Ile Ala Ala His Val Gly Gly Ser
1               5               10              15

His Asn Ile Glu Ala Val Gln Lys Ala His Gln Ala Leu Lys Glu Leu
            20              25              30

Asp

<210> SEQ ID NO 58
<211> LENGTH: 33
<212> TYPE: PRT
<213> ORGANISM: Burkholderia

<400> SEQUENCE: 58

Phe Ser Ser Gly Glu Thr Val Gly Ala Thr Val Gly Ala Gly Gly Thr
1               5               10              15

Glu Thr Val Ala Gln Gly Gly Thr Ala Ser Asn Thr Thr Val Ser Ser
            20              25              30

Gly

<210> SEQ ID NO 59
<211> LENGTH: 33
<212> TYPE: PRT
<213> ORGANISM: Burkholderia

<400> SEQUENCE: 59
```

-continued

```
Phe Ser Gly Gly Met Ala Thr Ser Thr Thr Val Gly Ser Gly Gly Thr
1               5                   10                  15

Gln Asp Val Leu Ala Gly Gly Ala Ala Val Gly Gly Thr Val Gly Thr
            20                  25                  30

Gly

<210> SEQ ID NO 60
<211> LENGTH: 33
<212> TYPE: PRT
<213> ORGANISM: Burkholderia

<400> SEQUENCE: 60

Phe Ser Ala Ala Asp Ile Val Lys Ile Ala Gly Lys Ile Gly Gly Ala
1               5                   10                  15

Gln Ala Leu Gln Ala Phe Ile Thr His Arg Ala Ala Leu Ile Gln Ala
            20                  25                  30

Gly

<210> SEQ ID NO 61
<211> LENGTH: 33
<212> TYPE: PRT
<213> ORGANISM: Burkholderia

<400> SEQUENCE: 61

Phe Asn Pro Thr Asp Ile Val Lys Ile Ala Gly Asn Asp Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 62
<211> LENGTH: 33
<212> TYPE: PRT
<213> ORGANISM: Burkholderia

<400> SEQUENCE: 62

Phe Asn Pro Thr Asp Ile Val Arg Met Ala Gly Asn Asp Gly Gly Ala
1               5                   10                  15

Gln Ala Leu Gln Ala Val Phe Glu Leu Glu Pro Ala Phe Arg Glu Arg
            20                  25                  30

Ser

<210> SEQ ID NO 63
<211> LENGTH: 33
<212> TYPE: PRT
<213> ORGANISM: Burkholderia

<400> SEQUENCE: 63

Phe Asn Pro Thr Asp Ile Val Arg Met Ala Gly Asn Asp Gly Gly Ala
1               5                   10                  15

Gln Ala Leu Gln Ala Val Leu Glu Leu Glu Pro Ala Phe Arg Glu Arg
            20                  25                  30

Gly

<210> SEQ ID NO 64
<211> LENGTH: 33
<212> TYPE: PRT
<213> ORGANISM: Burkholderia

<400> SEQUENCE: 64
```

-continued

```
Phe Ser Gln Val Asp Ile Val Lys Ile Ala Ser Asn Asp Gly Gly Ala
1               5                   10                  15

Gln Ala Leu Tyr Ser Val Leu Asp Val Glu Pro Thr Phe Arg Glu Arg
            20                  25                  30

Gly

<210> SEQ ID NO 65
<211> LENGTH: 33
<212> TYPE: PRT
<213> ORGANISM: Burkholderia

<400> SEQUENCE: 65

Phe Ser Arg Ala Asp Ile Val Lys Ile Ala Gly Asn Asp Gly Gly Ala
1               5                   10                  15

Gln Ala Leu Tyr Ser Val Leu Asp Val Glu Pro Pro Leu Arg Glu Arg
            20                  25                  30

Gly

<210> SEQ ID NO 66
<211> LENGTH: 33
<212> TYPE: PRT
<213> ORGANISM: Burkholderia

<400> SEQUENCE: 66

Phe Ser Arg Gly Asp Ile Val Lys Ile Ala Gly Asn Asp Gly Gly Ala
1               5                   10                  15

Gln Ala Leu Tyr Ser Val Leu Asp Val Glu Pro Pro Leu Arg Glu Arg
            20                  25                  30

Gly

<210> SEQ ID NO 67
<211> LENGTH: 33
<212> TYPE: PRT
<213> ORGANISM: Burkholderia

<400> SEQUENCE: 67

Phe Asn Arg Ala Asp Ile Val Arg Ile Ala Gly Asn Gly Gly Gly Ala
1               5                   10                  15

Gln Ala Leu Tyr Ser Val Arg Asp Ala Gly Pro Thr Leu Gly Lys Arg
            20                  25                  30

Gly

<210> SEQ ID NO 68
<211> LENGTH: 33
<212> TYPE: PRT
<213> ORGANISM: Burkholderia

<400> SEQUENCE: 68

Phe Arg Gln Ala Asp Ile Val Lys Ile Ala Ser Asn Gly Gly Ser Ala
1               5                   10                  15

Gln Ala Leu Asn Ala Val Ile Lys Leu Gly Pro Thr Leu Arg Gln Arg
            20                  25                  30

Gly

<210> SEQ ID NO 69
<211> LENGTH: 33
<212> TYPE: PRT
<213> ORGANISM: Burkholderia
```

-continued

```
<400> SEQUENCE: 69

Phe Arg Gln Ala Asp Ile Val Lys Met Ala Ser Asn Gly Gly Ser Ala
1               5                   10                  15

Gln Ala Leu Asn Ala Val Ile Lys Leu Gly Pro Thr Leu Arg Gln Arg
            20                  25                  30

Gly

<210> SEQ ID NO 70
<211> LENGTH: 33
<212> TYPE: PRT
<213> ORGANISM: Burkholderia

<400> SEQUENCE: 70

Phe Ser Arg Ala Asp Ile Val Lys Ile Ala Gly Asn Gly Gly Gly Ala
1               5                   10                  15

Gln Ala Leu Gln Ala Val Leu Glu Leu Glu Pro Thr Phe Arg Glu Arg
            20                  25                  30

Gly

<210> SEQ ID NO 71
<211> LENGTH: 33
<212> TYPE: PRT
<213> ORGANISM: Burkholderia

<400> SEQUENCE: 71

Phe Ser Arg Ala Asp Ile Val Arg Ile Ala Gly Asn Gly Gly Gly Ala
1               5                   10                  15

Gln Ala Leu Tyr Ser Val Leu Asp Val Gly Pro Thr Leu Gly Lys Arg
            20                  25                  30

Gly

<210> SEQ ID NO 72
<211> LENGTH: 33
<212> TYPE: PRT
<213> ORGANISM: Burkholderia

<400> SEQUENCE: 72

Phe Ser Arg Gly Asp Ile Val Arg Ile Ala Gly Asn Gly Gly Gly Ala
1               5                   10                  15

Gln Ala Leu Gln Ala Val Leu Glu Leu Glu Pro Thr Leu Gly Glu Arg
            20                  25                  30

Gly

<210> SEQ ID NO 73
<211> LENGTH: 33
<212> TYPE: PRT
<213> ORGANISM: Burkholderia

<400> SEQUENCE: 73

Phe Ser Arg Ala Asp Ile Val Lys Ile Ala Gly Asn Gly Gly Gly Ala
1               5                   10                  15

Gln Ala Leu Gln Ala Val Ile Thr His Arg Ala Ala Leu Thr Gln Ala
            20                  25                  30

Gly

<210> SEQ ID NO 74
<211> LENGTH: 33
<212> TYPE: PRT
<213> ORGANISM: Burkholderia
```

-continued

```
<400> SEQUENCE: 74

Phe Ser Arg Gly Asp Thr Val Lys Ile Ala Gly Asn Ile Gly Gly Ala
1               5                   10                  15

Gln Ala Leu Gln Ala Val Leu Glu Leu Glu Pro Thr Leu Arg Glu Arg
            20                  25                  30

Gly

<210> SEQ ID NO 75
<211> LENGTH: 33
<212> TYPE: PRT
<213> ORGANISM: Burkholderia

<400> SEQUENCE: 75

Phe Asn Pro Thr Asp Ile Val Lys Ile Ala Gly Asn Ile Gly Gly Ala
1               5                   10                  15

Gln Ala Leu Gln Ala Val Leu Glu Leu Glu Pro Ala Phe Arg Glu Arg
            20                  25                  30

Gly

<210> SEQ ID NO 76
<211> LENGTH: 33
<212> TYPE: PRT
<213> ORGANISM: Burkholderia

<400> SEQUENCE: 76

Phe Ser Ala Ala Asp Ile Val Lys Ile Ala Gly Asn Ile Gly Gly Ala
1               5                   10                  15

Gln Ala Leu Gln Ala Ile Phe Thr His Arg Ala Ala Leu Ile Gln Ala
            20                  25                  30

Gly

<210> SEQ ID NO 77
<211> LENGTH: 33
<212> TYPE: PRT
<213> ORGANISM: Burkholderia

<400> SEQUENCE: 77

Phe Ser Ala Ala Asp Ile Val Lys Ile Ala Gly Asn Ile Gly Gly Ala
1               5                   10                  15

Gln Ala Leu Gln Ala Val Ile Thr His Arg Ala Thr Leu Thr Gln Ala
            20                  25                  30

Gly

<210> SEQ ID NO 78
<211> LENGTH: 33
<212> TYPE: PRT
<213> ORGANISM: Burkholderia

<400> SEQUENCE: 78

Phe Ser Ala Thr Asp Ile Val Lys Ile Ala Ser Asn Ile Gly Gly Ala
1               5                   10                  15

Gln Ala Leu Gln Ala Val Ile Ser Arg Arg Ala Ala Leu Ile Gln Ala
            20                  25                  30

Gly

<210> SEQ ID NO 79
<211> LENGTH: 33
<212> TYPE: PRT
```

<213> ORGANISM: Burkholderia

<400> SEQUENCE: 79

Phe Ser Gln Pro Asp Ile Val Lys Ile Ala Gly Asn Ile Gly Gly Ala
1                 5                   10                  15

Gln Ala Leu Gln Ala Val Leu Glu Leu Glu Pro Ala Phe Arg Glu Arg
            20                  25                  30

Gly

<210> SEQ ID NO 80
<211> LENGTH: 33
<212> TYPE: PRT
<213> ORGANISM: Burkholderia

<400> SEQUENCE: 80

Phe Ser Arg Ala Asp Ile Val Lys Ile Ala Gly Asn Ile Gly Gly Ala
1                 5                   10                  15

Gln Ala Leu Gln Ala Val Leu Glu Leu Glu Ser Thr Phe Arg Glu Arg
            20                  25                  30

Ser

<210> SEQ ID NO 81
<211> LENGTH: 33
<212> TYPE: PRT
<213> ORGANISM: Burkholderia

<400> SEQUENCE: 81

Phe Ser Arg Ala Asp Ile Val Lys Ile Ala Gly Asn Ile Gly Gly Ala
1                 5                   10                  15

Gln Ala Leu Gln Ala Val Leu Glu Leu Glu Ser Thr Leu Arg Glu Arg
            20                  25                  30

Ser

<210> SEQ ID NO 82
<211> LENGTH: 33
<212> TYPE: PRT
<213> ORGANISM: Burkholderia

<400> SEQUENCE: 82

Phe Ser Arg Gly Asp Ile Val Lys Met Ala Gly Asn Ile Gly Gly Ala
1                 5                   10                  15

Gln Ala Leu Gln Ala Gly Leu Glu Leu Glu Pro Ala Phe Arg Glu Arg
            20                  25                  30

Gly

<210> SEQ ID NO 83
<211> LENGTH: 33
<212> TYPE: PRT
<213> ORGANISM: Burkholderia

<400> SEQUENCE: 83

Phe Ser Arg Gly Asp Ile Val Lys Met Ala Gly Asn Ile Gly Gly Ala
1                 5                   10                  15

Gln Ala Leu Gln Ala Val Leu Glu Leu Glu Pro Ala Phe His Glu Arg
            20                  25                  30

Ser

<210> SEQ ID NO 84
<211> LENGTH: 33

```
<212> TYPE: PRT
<213> ORGANISM: Burkholderia

<400> SEQUENCE: 84

Phe Thr Leu Thr Asp Ile Val Lys Met Ala Gly Asn Ile Gly Gly Ala
1               5                   10                  15

Gln Ala Leu Lys Ala Val Leu Glu His Gly Pro Thr Leu Arg Gln Arg
            20                  25                  30

Asp

<210> SEQ ID NO 85
<211> LENGTH: 33
<212> TYPE: PRT
<213> ORGANISM: Burkholderia

<400> SEQUENCE: 85

Phe Thr Leu Thr Asp Ile Val Lys Met Ala Gly Asn Ile Gly Gly Ala
1               5                   10                  15

Gln Ala Leu Lys Val Val Leu Glu His Gly Pro Thr Leu Arg Gln Arg
            20                  25                  30

Asp

<210> SEQ ID NO 86
<211> LENGTH: 33
<212> TYPE: PRT
<213> ORGANISM: Burkholderia

<400> SEQUENCE: 86

Phe Asn Pro Thr Asp Ile Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 87
<211> LENGTH: 33
<212> TYPE: PRT
<213> ORGANISM: Burkholderia

<400> SEQUENCE: 87

Phe Asn Pro Thr Asp Ile Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Ser

<210> SEQ ID NO 88
<211> LENGTH: 33
<212> TYPE: PRT
<213> ORGANISM: Burkholderia

<400> SEQUENCE: 88

Phe Asn Pro Thr Asp Met Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 89
```

-continued

```
<211> LENGTH: 33
<212> TYPE: PRT
<213> ORGANISM: Burkholderia

<400> SEQUENCE: 89

Phe Ser Ala Ala Asp Ile Val Lys Ile Ala Ser Asn Asn Gly Gly Ala
1               5                   10                  15

Gln Ala Leu Gln Ala Leu Ile Asp His Trp Ser Thr Leu Ser Gly Lys
            20                  25                  30

Thr

<210> SEQ ID NO 90
<211> LENGTH: 33
<212> TYPE: PRT
<213> ORGANISM: Burkholderia

<400> SEQUENCE: 90

Phe Ser Ala Ala Asp Ile Val Lys Ile Ala Ser Asn Asn Gly Gly Ala
1               5                   10                  15

Gln Ala Leu Gln Ala Val Ile Ser Arg Arg Ala Ala Leu Ile Gln Ala
            20                  25                  30

Gly

<210> SEQ ID NO 91
<211> LENGTH: 33
<212> TYPE: PRT
<213> ORGANISM: Burkholderia

<400> SEQUENCE: 91

Phe Ser Ala Ala Asp Ile Val Lys Ile Ala Ser Asn Asn Gly Gly Ala
1               5                   10                  15

Gln Ala Leu Gln Ala Val Ile Thr His Arg Ala Ala Leu Ala Gln Ala
            20                  25                  30

Gly

<210> SEQ ID NO 92
<211> LENGTH: 33
<212> TYPE: PRT
<213> ORGANISM: Burkholderia

<400> SEQUENCE: 92

Phe Ser Ala Ala Asp Ile Val Lys Ile Ala Ser Asn Asn Gly Gly Ala
1               5                   10                  15

Arg Ala Leu Gln Ala Leu Ile Asp His Trp Ser Thr Leu Ser Gly Lys
            20                  25                  30

Thr

<210> SEQ ID NO 93
<211> LENGTH: 33
<212> TYPE: PRT
<213> ORGANISM: Burkholderia

<400> SEQUENCE: 93

Phe Thr Leu Thr Asp Ile Val Glu Met Ala Gly Asn Asn Gly Gly Ala
1               5                   10                  15

Gln Ala Leu Lys Ala Val Leu Glu His Gly Ser Thr Leu Asp Glu Arg
            20                  25                  30

Gly
```

```
<210> SEQ ID NO 94
<211> LENGTH: 33
<212> TYPE: PRT
<213> ORGANISM: Burkholderia

<400> SEQUENCE: 94

Phe Thr Leu Thr Asp Ile Val Lys Met Ala Gly Asn Asn Gly Gly Ala
1               5                   10                  15

Gln Ala Leu Lys Ala Val Leu Glu His Gly Pro Thr Leu Asp Glu Arg
            20                  25                  30

Gly

<210> SEQ ID NO 95
<211> LENGTH: 33
<212> TYPE: PRT
<213> ORGANISM: Burkholderia

<400> SEQUENCE: 95

Phe Thr Leu Thr Asp Ile Val Lys Met Ala Gly Asn Asn Gly Gly Ala
1               5                   10                  15

Gln Ala Leu Lys Val Val Leu Glu His Gly Pro Thr Leu Arg Gln Arg
            20                  25                  30

Gly

<210> SEQ ID NO 96
<211> LENGTH: 33
<212> TYPE: PRT
<213> ORGANISM: Burkholderia

<400> SEQUENCE: 96

Phe Thr Leu Thr Asp Ile Val Lys Met Ala Ser Asn Asn Gly Gly Ala
1               5                   10                  15

Gln Ala Leu Lys Ala Val Leu Glu His Gly Pro Thr Leu Asp Glu Arg
            20                  25                  30

Gly

<210> SEQ ID NO 97
<211> LENGTH: 33
<212> TYPE: PRT
<213> ORGANISM: Burkholderia

<400> SEQUENCE: 97

Phe Ser Ala Ala Asp Ile Val Lys Ile Ala Gly Asn Ser Gly Gly Ala
1               5                   10                  15

Gln Ala Leu Gln Ala Val Ile Ser His Arg Ala Ala Leu Thr Gln Ala
            20                  25                  30

Gly

<210> SEQ ID NO 98
<211> LENGTH: 33
<212> TYPE: PRT
<213> ORGANISM: Burkholderia

<400> SEQUENCE: 98

Phe Ser Gly Gly Asp Ala Val Ser Thr Val Val Arg Ser Gly Gly Ala
1               5                   10                  15

Gln Ser Val Ala Ser Gly Gly Thr Ala Ser Gly Thr Thr Val Ser Ala
            20                  25                  30

Gly
```

-continued

```
<210> SEQ ID NO 99
<211> LENGTH: 33
<212> TYPE: PRT
<213> ORGANISM: Burkholderia

<400> SEQUENCE: 99

Phe Arg Gln Thr Asp Ile Val Lys Met Ala Gly Ser Gly Gly Ser Ala
1               5                   10                  15

Gln Ala Leu Asn Ala Val Ile Lys His Gly Pro Thr Leu Arg Gln Arg
            20                  25                  30

Gly

<210> SEQ ID NO 100
<211> LENGTH: 33
<212> TYPE: PRT
<213> ORGANISM: Burkholderia

<400> SEQUENCE: 100

Phe Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Thr Gln Ala Gly
            20                  25                  30

Arg

<210> SEQ ID NO 101
<211> LENGTH: 33
<212> TYPE: PRT
<213> ORGANISM: Burkholderia

<400> SEQUENCE: 101

Phe Ser Gly Gly Asp Ala Ala Gly Thr Val Val Ser Ser Gly Gly Ala
1               5                   10                  15

Gln Asn Val Thr Gly Gly Leu Ala Ser Gly Thr Thr Val Ala Ser Gly
            20                  25                  30

Gly

<210> SEQ ID NO 102
<211> LENGTH: 33
<212> TYPE: PRT
<213> ORGANISM: Paraburkholderia

<400> SEQUENCE: 102

Phe Asn Leu Thr Asp Ile Val Glu Met Ala Ala Asn Ser Gly Gly Ala
1               5                   10                  15

Gln Ala Leu Lys Ala Val Leu Glu His Gly Pro Thr Leu Arg Gln Arg
            20                  25                  30

Gly

<210> SEQ ID NO 103
<211> LENGTH: 33
<212> TYPE: PRT
<213> ORGANISM: Paraburkholderia

<400> SEQUENCE: 103

Phe Asn Arg Ala Ser Ile Val Lys Ile Ala Gly Asn Ser Gly Gly Ala
1               5                   10                  15

Gln Ala Leu Gln Ala Val Leu Lys His Gly Pro Thr Leu Asp Glu Arg
            20                  25                  30

Gly
```

-continued

```
<210> SEQ ID NO 104
<211> LENGTH: 33
<212> TYPE: PRT
<213> ORGANISM: Paraburkholderia

<400> SEQUENCE: 104

Phe Ser Gln Ala Asn Ile Val Lys Met Ala Gly Asn Ser Gly Gly Ala
1               5                   10                  15

Gln Ala Leu Gln Ala Val Leu Asp Leu Glu Leu Val Phe Arg Glu Arg
            20                  25                  30

Gly

<210> SEQ ID NO 105
<211> LENGTH: 33
<212> TYPE: PRT
<213> ORGANISM: Paraburkholderia

<400> SEQUENCE: 105

Phe Ser Gln Pro Asp Ile Val Lys Met Ala Gly Asn Ser Gly Gly Ala
1               5                   10                  15

Gln Ala Leu Gln Ala Val Leu Asp Leu Glu Leu Ala Phe Arg Glu Arg
            20                  25                  30

Gly

<210> SEQ ID NO 106
<211> LENGTH: 33
<212> TYPE: PRT
<213> ORGANISM: Paraburkholderia

<400> SEQUENCE: 106

Phe Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Met Gln Ala Gly
            20                  25                  30

Arg

<210> SEQ ID NO 107
<211> LENGTH: 33
<212> TYPE: PRT
<213> ORGANISM: Francisella

<400> SEQUENCE: 107

Tyr Lys Ser Glu Asp Ile Ile Arg Leu Ala Ser His Asp Gly Gly Ser
1               5                   10                  15

Val Asn Leu Glu Ala Val Leu Arg Leu His Ser Gln Leu Thr Arg Leu
            20                  25                  30

Gly

<210> SEQ ID NO 108
<211> LENGTH: 33
<212> TYPE: PRT
<213> ORGANISM: Francisella

<400> SEQUENCE: 108

Tyr Lys Pro Glu Asp Ile Ile Arg Leu Ala Ser His Gly Gly Gly Ser
1               5                   10                  15

Val Asn Leu Glu Ala Val Leu Arg Leu Asn Pro Gln Leu Ile Gly Leu
            20                  25                  30
```

Gly

<210> SEQ ID NO 109
<211> LENGTH: 33
<212> TYPE: PRT
<213> ORGANISM: Francisella

<400> SEQUENCE: 109

Tyr Lys Ser Glu Asp Ile Ile Arg Leu Ala Ser His Gly Gly Gly Ser
1               5                   10                  15

Val Asn Leu Glu Ala Val Leu Arg Leu His Ser Gln Leu Thr Arg Leu
            20                  25                  30

Gly

<210> SEQ ID NO 110
<211> LENGTH: 33
<212> TYPE: PRT
<213> ORGANISM: Francisella

<400> SEQUENCE: 110

Tyr Lys Ser Glu Asp Ile Ile Arg Leu Ala Ser His Gly Gly Gly Ser
1               5                   10                  15

Val Asn Leu Glu Ala Val Leu Arg Leu Asn Pro Gln Leu Ile Gly Leu
            20                  25                  30

Gly

<210> SEQ ID NO 111
<211> LENGTH: 33
<212> TYPE: PRT
<213> ORGANISM: L. quateirensis

<400> SEQUENCE: 111

Leu Gly His Lys Glu Leu Ile Lys Ile Ala Ala Arg Asn Gly Gly Gly
1               5                   10                  15

Asn Asn Leu Ile Ala Val Leu Ser Cys Tyr Ala Lys Leu Lys Glu Met
            20                  25                  30

Gly

<210> SEQ ID NO 112
<211> LENGTH: 33
<212> TYPE: PRT
<213> ORGANISM: Paraburkholderia

<400> SEQUENCE: 112

Phe Asn Leu Thr Asp Ile Val Glu Met Ala Gly Lys Gly Gly Gly Ala
1               5                   10                  15

Gln Ala Leu Lys Ala Val Leu Glu His Gly Pro Thr Leu Arg Gln Arg
            20                  25                  30

Gly

<210> SEQ ID NO 113
<211> LENGTH: 33
<212> TYPE: PRT
<213> ORGANISM: Paraburkholderia

<400> SEQUENCE: 113

Phe Arg Gln Ala Asp Ile Ile Lys Ile Ala Gly Asn Asp Gly Gly Ala
1               5                   10                  15

Gln Ala Leu Gln Ala Val Ile Glu His Gly Pro Thr Leu Arg Gln His
            20                  25                  30

-continued

```
Gly

<210> SEQ ID NO 114
<211> LENGTH: 33
<212> TYPE: PRT
<213> ORGANISM: Paraburkholderia

<400> SEQUENCE: 114

Phe Ser Gln Ala Asp Ile Val Lys Ile Ala Gly Asn Asp Gly Gly Thr
1               5                   10                  15

Gln Ala Leu His Ala Val Leu Asp Leu Glu Arg Met Leu Gly Glu Arg
            20                  25                  30

Gly

<210> SEQ ID NO 115
<211> LENGTH: 33
<212> TYPE: PRT
<213> ORGANISM: Paraburkholderia

<400> SEQUENCE: 115

Phe Ser Arg Ala Asp Ile Val Lys Ile Ala Gly Asn Gly Gly Gly Ala
1               5                   10                  15

Gln Ala Leu Lys Ala Val Leu Glu His Glu Ala Thr Leu Asp Glu Arg
            20                  25                  30

Gly

<210> SEQ ID NO 116
<211> LENGTH: 33
<212> TYPE: PRT
<213> ORGANISM: Paraburkholderia

<400> SEQUENCE: 116

Phe Ser Arg Ala Asp Ile Val Arg Ile Ala Gly Asn Gly Gly Gly Ala
1               5                   10                  15

Gln Ala Leu Tyr Ser Val Leu Asp Val Glu Pro Thr Leu Gly Lys Arg
            20                  25                  30

Gly

<210> SEQ ID NO 117
<211> LENGTH: 33
<212> TYPE: PRT
<213> ORGANISM: Paraburkholderia

<400> SEQUENCE: 117

Phe Ser Gln Pro Asp Ile Val Lys Met Ala Ser Asn Ile Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 118
<211> LENGTH: 33
<212> TYPE: PRT
<213> ORGANISM: Paraburkholderia

<400> SEQUENCE: 118

Phe Ser Gln Pro Asp Ile Val Lys Met Ala Gly Asn Ile Gly Gly Ala
1               5                   10                  15

Gln Ala Leu Gln Ala Val Leu Ser Leu Gly Pro Ala Leu Arg Glu Arg
```

-continued

```
              20              25              30

Gly

<210> SEQ ID NO 119
<211> LENGTH: 33
<212> TYPE: PRT
<213> ORGANISM: Paraburkholderia

<400> SEQUENCE: 119

Phe Ser Gln Pro Glu Ile Val Lys Ile Ala Gly Asn Ile Gly Gly Ala
1               5               10              15

Gln Ala Leu His Thr Val Leu Glu Leu Glu Pro Thr Leu His Lys Arg
              20              25              30

Gly

<210> SEQ ID NO 120
<211> LENGTH: 33
<212> TYPE: PRT
<213> ORGANISM: Paraburkholderia

<400> SEQUENCE: 120

Phe Ser Gln Ser Asp Ile Val Lys Ile Ala Gly Asn Ile Gly Gly Ala
1               5               10              15

Gln Ala Leu Gln Ala Val Leu Asp Leu Glu Ser Met Leu Gly Lys Arg
              20              25              30

Gly

<210> SEQ ID NO 121
<211> LENGTH: 33
<212> TYPE: PRT
<213> ORGANISM: Paraburkholderia

<400> SEQUENCE: 121

Phe Ser Gln Ser Asp Ile Val Lys Ile Ala Gly Asn Ile Gly Gly Ala
1               5               10              15

Gln Ala Leu Gln Ala Val Leu Glu Leu Glu Pro Thr Leu Arg Glu Ser
              20              25              30

Asp

<210> SEQ ID NO 122
<211> LENGTH: 33
<212> TYPE: PRT
<213> ORGANISM: Paraburkholderia

<400> SEQUENCE: 122

Phe Asn Pro Thr Asp Ile Val Lys Ile Ala Gly Asn Lys Gly Gly Ala
1               5               10              15

Gln Ala Leu Gln Ala Val Leu Glu Leu Glu Pro Ala Leu Arg Glu Arg
              20              25              30

Gly

<210> SEQ ID NO 123
<211> LENGTH: 33
<212> TYPE: PRT
<213> ORGANISM: Paraburkholderia

<400> SEQUENCE: 123

Phe Ser Pro Thr Asp Ile Ile Lys Ile Ala Gly Asn Asn Gly Gly Ala
1               5               10              15
```

```
Gln Ala Leu Gln Ala Val Leu Asp Leu Glu Leu Met Leu Arg Glu Arg
        20                  25                  30

Gly

<210> SEQ ID NO 124
<211> LENGTH: 33
<212> TYPE: PRT
<213> ORGANISM: Paraburkholderia

<400> SEQUENCE: 124

Phe Ser Gln Ala Asp Ile Val Lys Ile Ala Gly Asn Asn Gly Gly Ala
1               5                   10                  15

Gln Ala Leu Tyr Ser Val Leu Asp Val Glu Pro Thr Leu Gly Lys Arg
        20                  25                  30

Gly

<210> SEQ ID NO 125
<211> LENGTH: 33
<212> TYPE: PRT
<213> ORGANISM: Paraburkholderia

<400> SEQUENCE: 125

Phe Ser Arg Gly Asp Ile Val Thr Ile Ala Gly Asn Asn Gly Gly Ala
1               5                   10                  15

Gln Ala Leu Gln Ala Val Leu Glu Leu Glu Pro Thr Leu Arg Glu Arg
        20                  25                  30

Gly

<210> SEQ ID NO 126
<211> LENGTH: 33
<212> TYPE: PRT
<213> ORGANISM: Paraburkholderia

<400> SEQUENCE: 126

Phe Ser Arg Ile Asp Ile Val Lys Ile Ala Ala Asn Asn Gly Gly Ala
1               5                   10                  15

Gln Ala Leu His Ala Val Leu Asp Leu Gly Pro Thr Leu Arg Glu Cys
        20                  25                  30

Gly

<210> SEQ ID NO 127
<211> LENGTH: 33
<212> TYPE: PRT
<213> ORGANISM: Paraburkholderia

<400> SEQUENCE: 127

Phe Ser Gln Ala Asp Ile Val Lys Ile Val Gly Asn Asn Gly Gly Ala
1               5                   10                  15

Gln Ala Leu Gln Ala Val Phe Glu Leu Glu Pro Thr Leu Arg Glu Arg
        20                  25                  30

Gly

<210> SEQ ID NO 128
<211> LENGTH: 33
<212> TYPE: PRT
<213> ORGANISM: Paraburkholderia

<400> SEQUENCE: 128

Phe Ser Gln Pro Asp Ile Val Arg Ile Thr Gly Asn Arg Gly Gly Ala
1               5                   10                  15
```

-continued

```
Gln Ala Leu Gln Ala Val Leu Ala Leu Glu Leu Thr Leu Arg Glu Arg
            20                  25                  30

Gly

<210> SEQ ID NO 129
<211> LENGTH: 33
<212> TYPE: PRT
<213> ORGANISM: Legionellales

<400> SEQUENCE: 129

Phe Lys Ala Asp Asp Ala Val Arg Ile Ala Cys Arg Thr Gly Gly Ser
1               5                   10                  15

His Asn Leu Lys Ala Val His Lys Asn Tyr Glu Arg Leu Arg Ala Arg
            20                  25                  30

Gly

<210> SEQ ID NO 130
<211> LENGTH: 33
<212> TYPE: PRT
<213> ORGANISM: Legionellales

<400> SEQUENCE: 130

Phe Asn Ala Asp Gln Val Ile Lys Ile Val Gly His Asp Gly Gly Ser
1               5                   10                  15

Asn Asn Ile Asp Val Val Gln Gln Phe Phe Pro Glu Leu Lys Ala Phe
            20                  25                  30

Gly

<210> SEQ ID NO 131
<211> LENGTH: 33
<212> TYPE: PRT
<213> ORGANISM: L. maceachernii

<400> SEQUENCE: 131

Phe Ser Ala Glu Gln Ile Val Arg Ile Ala Ala His Ile Gly Gly Ser
1               5                   10                  15

Arg Asn Ile Glu Ala Thr Ile Lys His Tyr Ala Met Leu Thr Gln Pro
            20                  25                  30

Pro

<210> SEQ ID NO 132
<211> LENGTH: 33
<212> TYPE: PRT
<213> ORGANISM: Francisella

<400> SEQUENCE: 132

Tyr Lys Ser Glu Asp Ile Ile Arg Leu Ala Ser His Asp Gly Gly Ser
1               5                   10                  15

Val Asn Leu Glu Ala Val Leu Arg Leu Asn Pro Gln Leu Ile Gly Leu
            20                  25                  30

Gly

<210> SEQ ID NO 133
<211> LENGTH: 33
<212> TYPE: PRT
<213> ORGANISM: Francisella

<400> SEQUENCE: 133

Tyr Lys Ser Glu Asp Ile Ile Arg Leu Ala Ser His Asp Gly Gly Ser
```

-continued

```
1               5              10             15

Ile Asn Leu Glu Ala Val Leu Arg Leu Asn Pro Gln Leu Ile Gly Leu
            20             25             30

Gly

<210> SEQ ID NO 134
<211> LENGTH: 33
<212> TYPE: PRT
<213> ORGANISM: Francisella

<400> SEQUENCE: 134

Tyr Lys Ser Glu Asp Ile Ile Arg Leu Ala Ser Ser Asn Gly Gly Ser
1               5              10             15

Val Asn Leu Glu Ala Val Leu Arg Leu Asn Pro Gln Leu Ile Gly Leu
            20             25             30

Gly

<210> SEQ ID NO 135
<211> LENGTH: 33
<212> TYPE: PRT
<213> ORGANISM: Francisella

<400> SEQUENCE: 135

Tyr Lys Ser Glu Asp Ile Ile Arg Leu Ala Ser Ser Asn Gly Gly Ser
1               5              10             15

Val Asn Leu Glu Ala Val Ile Ala Val His Lys Ala Leu His Ser Asn
            20             25             30

Gly

<210> SEQ ID NO 136
<211> LENGTH: 33
<212> TYPE: PRT
<213> ORGANISM: Legionellales

<400> SEQUENCE: 136

Phe Ser Ala Asp Gln Val Val Lys Ile Ala Gly His Ser Gly Gly Ser
1               5              10             15

Asn Asn Ile Ala Val Met Leu Ala Val Phe Pro Arg Leu Arg Asp Phe
            20             25             30

Gly

<210> SEQ ID NO 137
<211> LENGTH: 33
<212> TYPE: PRT
<213> ORGANISM: Francisella

<400> SEQUENCE: 137

Tyr Lys Ile Asn His Cys Val Asn Leu Leu Lys Leu Asn His Asp Gly
1               5              10             15

Phe Met Leu Lys Asn Leu Ile Pro Tyr Asp Ser Lys Leu Thr Gly Leu
            20             25             30

Gly

<210> SEQ ID NO 138
<211> LENGTH: 19
<212> TYPE: PRT
<213> ORGANISM: L. quateirensis
<220> FEATURE:
<221> NAME/KEY: MISC_FEATURE
<222> LOCATION: (12)..(13)
```

```
<223> OTHER INFORMATION: XX is a base contacting residue chosen based
      upon a target nucleic acid sequence

<400> SEQUENCE: 138

Phe Asn Ala Glu Gln Ile Val Arg Met Val Ser Xaa Xaa Gly Gly Ser
1               5                   10                  15

Lys Asn Leu

<210> SEQ ID NO 139
<211> LENGTH: 16
<212> TYPE: PRT
<213> ORGANISM: Francisella
<220> FEATURE:
<221> NAME/KEY: misc_feature
<222> LOCATION: (12)..(13)
<223> OTHER INFORMATION: XX is a base contacting residue chosen based
      upon a target nucleic acid sequence

<400> SEQUENCE: 139

Tyr Asn Lys Lys Gln Ile Val Leu Ile Ala Ser Xaa Xaa Ser Gly Gly
1               5                   10                  15

<210> SEQ ID NO 140
<211> LENGTH: 143
<212> TYPE: PRT
<213> ORGANISM: L. quateirensis

<400> SEQUENCE: 140

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Ser Pro Ala Ser Ala Asn Ala Arg
            35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly
    130                 135                 140

<210> SEQ ID NO 141
<211> LENGTH: 176
<212> TYPE: PRT
<213> ORGANISM: L. quateirensis

<400> SEQUENCE: 141

Ala Leu Val Lys Glu Tyr Phe Pro Val Phe Ser Ser Phe His Phe Thr
1               5                   10                  15

Ala Asp Gln Ile Val Ala Leu Ile Cys Gln Ser Lys Gln Cys Phe Arg
                20                  25                  30

Asn Leu Lys Lys Asn His Gln Gln Trp Lys Asn Lys Gly Leu Ser Ala
            35                  40                  45

Glu Gln Ile Val Asp Leu Ile Leu Gln Glu Thr Pro Pro Lys Pro Asn
```

```
                50                55                60

Phe Asn Asn Thr Ser Ser Ser Thr Pro Ser Pro Ser Ala Pro Ser Phe
65                  70                75                  80

Phe Gln Gly Pro Ser Thr Pro Ile Pro Thr Pro Val Leu Asp Asn Ser
                85                90                95

Pro Ala Pro Ile Phe Ser Asn Pro Val Cys Phe Phe Ser Ser Arg Ser
                100               105               110

Glu Asn Asn Thr Glu Gln Tyr Leu Gln Asp Ser Thr Leu Asp Leu Asp
            115               120               125

Ser Gln Leu Gly Asp Pro Thr Lys Asn Phe Asn Val Asn Asn Phe Trp
    130               135               140

Ser Leu Phe Pro Phe Asp Asp Val Gly Tyr His Pro His Ser Asn Asp
145               150               155               160

Val Gly Tyr His Leu His Ser Asp Glu Glu Ser Pro Phe Phe Asp Phe
                165               170               175

<210> SEQ ID NO 142
<211> LENGTH: 176
<212> TYPE: PRT
<213> ORGANISM: Burkholderia, Paraburkholderia, or Xanthomonas

<400> SEQUENCE: 142

Ala Leu Val Lys Glu Tyr Phe Pro Val Phe Ser Ser Phe His Phe Thr
1               5                 10                15

Ala Asp Gln Ile Val Ala Leu Ile Cys Gln Ser Lys Gln Cys Phe Arg
                20                25                30

Asn Leu Lys Lys Asn His Gln Gln Trp Lys Asn Lys Gly Leu Ser Ala
            35                40                45

Glu Gln Ile Val Asp Leu Ile Leu Gln Glu Thr Pro Pro Lys Pro Asn
    50                55                60

Phe Asn Asn Thr Ser Ser Ser Thr Pro Ser Pro Ser Ala Pro Ser Phe
65                  70                75                  80

Phe Gln Gly Pro Ser Thr Pro Ile Pro Thr Pro Val Leu Asp Asn Ser
                85                90                95

Pro Ala Pro Ile Phe Ser Asn Pro Val Cys Phe Phe Ser Ser Arg Ser
                100               105               110

Glu Asn Asn Thr Glu Gln Tyr Leu Gln Asp Ser Thr Leu Asp Leu Asp
            115               120               125

Ser Gln Leu Gly Asp Pro Thr Lys Asn Phe Asn Val Asn Asn Phe Trp
    130               135               140

Ser Leu Phe Pro Phe Asp Asp Val Gly Tyr His Pro His Ser Asn Asp
145               150               155               160

Val Gly Tyr His Leu His Ser Asp Glu Glu Ser Pro Phe Phe Asp Phe
                165               170               175

<210> SEQ ID NO 143
<211> LENGTH: 17
<212> TYPE: DNA
<213> ORGANISM: Artificial sequence
<220> FEATURE:
<223> OTHER INFORMATION: synthetic sequence

<400> SEQUENCE: 143
tttctgtcac caatcct                                                    17

<210> SEQ ID NO 144
<211> LENGTH: 18
```

```
<212> TYPE: DNA
<213> ORGANISM: Artificial sequence
<220> FEATURE:
<223> OTHER INFORMATION: synthetic sequence

<400> SEQUENCE: 144
tcccctccac cccacagt                                                          18

<210> SEQ ID NO 145
<211> LENGTH: 19
<212> TYPE: DNA
<213> ORGANISM: Artificial sequence
<220> FEATURE:
<223> OTHER INFORMATION: synthetic sequence

<400> SEQUENCE: 145
tgccttgacc aatagcctt                                                         19

<210> SEQ ID NO 146
<211> LENGTH: 15
<212> TYPE: DNA
<213> ORGANISM: Artificial sequence
<220> FEATURE:
<223> OTHER INFORMATION: synthetic sequence

<400> SEQUENCE: 146
tgccttgacc aatag                                                             15

<210> SEQ ID NO 147
<211> LENGTH: 22
<212> TYPE: DNA
<213> ORGANISM: Artificial sequence
<220> FEATURE:
<223> OTHER INFORMATION: synthetic sequence

<400> SEQUENCE: 147
gccttgtcaa ggctattggt ca                                                     22

<210> SEQ ID NO 148
<211> LENGTH: 15
<212> TYPE: DNA
<213> ORGANISM: Artificial sequence
<220> FEATURE:
<223> OTHER INFORMATION: synthetic sequence

<400> SEQUENCE: 148
tccccacact atctc                                                             15

<210> SEQ ID NO 149
<211> LENGTH: 19
<212> TYPE: DNA
<213> ORGANISM: Artificial sequence
<220> FEATURE:
<223> OTHER INFORMATION: synthetic sequence

<400> SEQUENCE: 149
tccccacact atctcaatg                                                         19

<210> SEQ ID NO 150
<211> LENGTH: 134
<212> TYPE: PRT
<213> ORGANISM: Artificial sequence
<220> FEATURE:
<223> OTHER INFORMATION: synthetic sequence

<400> SEQUENCE: 150
```

```
Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Lys Tyr Gln Asp Met Ile Ala
    50                  55                  60

Ala Leu Pro Glu Ala Thr His Glu Ala Ile Val Gly Val Gly Lys Gln
65                  70                  75                  80

Trp Ser Gly Ala Arg Ala Leu Glu Ala Leu Leu Thr Val Ala Gly Glu
                85                  90                  95

Leu Arg Gly Pro Pro Leu Gln Leu Asp Thr Gly Gln Leu Leu Lys Ile
            100                 105                 110

Ala Lys Arg Gly Gly Val Thr Ala Val Glu Ala Val His Ala Trp Arg
            115                 120                 125

Asn Ala Leu Thr Gly Ala
    130
```

```
<210> SEQ ID NO 151
<211> LENGTH: 63
<212> TYPE: PRT
<213> ORGANISM: Artificial sequence
<220> FEATURE:
<223> OTHER INFORMATION: synthetic sequence

<400> SEQUENCE: 151
```

```
Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
            20                  25                  30

Leu Asp Ala Val Lys Lys Gly Leu Pro His Ala Pro Ala Leu Ile Lys
        35                  40                  45

Arg Thr Asn Arg Arg Ile Pro Glu Arg Thr Ser His Arg Val Ala
    50                  55                  60
```

```
<210> SEQ ID NO 152
<211> LENGTH: 20
<212> TYPE: PRT
<213> ORGANISM: Artificial sequence
<220> FEATURE:
<223> OTHER INFORMATION: synthetic sequence

<400> SEQUENCE: 152
```

```
Leu Thr Pro Asp Gln Val Val Ala Ile Ala Ser Asn Ile Gly Gly Arg
1               5                   10                  15

Pro Ala Leu Glu
            20
```

```
<210> SEQ ID NO 153
<211> LENGTH: 20
<212> TYPE: PRT
<213> ORGANISM: Artificial sequence
<220> FEATURE:
<223> OTHER INFORMATION: synthetic sequence

<400> SEQUENCE: 153
```

```
Leu Thr Pro Asp Gln Val Val Ala Ile Ala Ser Asn Gly Gly Gly Arg
1               5                   10                  15

Pro Ala Leu Glu
```

```
                    20

<210> SEQ ID NO 154
<211> LENGTH: 20
<212> TYPE: PRT
<213> ORGANISM: Artificial sequence
<220> FEATURE:
<223> OTHER INFORMATION: synthetic sequence

<400> SEQUENCE: 154

Leu Thr Pro Asp Gln Val Val Ala Ile Ala Ser His Asp Gly Gly Arg
1               5                   10                  15

Pro Ala Leu Glu
            20

<210> SEQ ID NO 155
<211> LENGTH: 20
<212> TYPE: PRT
<213> ORGANISM: Artificial sequence
<220> FEATURE:
<223> OTHER INFORMATION: synthetic sequence

<400> SEQUENCE: 155

Leu Thr Pro Asp Gln Val Val Ala Ile Ala Ser Asn His Gly Gly Arg
1               5                   10                  15

Pro Ala Leu Glu
            20

<210> SEQ ID NO 156
<211> LENGTH: 805
<212> TYPE: PRT
<213> ORGANISM: Artificial sequence
<220> FEATURE:
<223> OTHER INFORMATION: synthetic sequence

<400> SEQUENCE: 156

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Ile Gly Gly Lys
            180                 185                 190
```

-continued

```
Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser Asn Gly Gly
        210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser His
                245                 250                 255

Asp Gly Gly Lys Gln Ala Leu Glu Thr Val Gln Arg Leu Leu Pro Val
                260                 265                 270

Leu Cys Gln Asp His Gly Leu Thr Pro Asp Gln Val Val Ala Ile Ala
        275                 280                 285

Ser His Asp Gly Gly Lys Gln Ala Leu Glu Thr Val Gln Arg Leu Leu
        290                 295                 300

Pro Val Leu Cys Gln Asp His Gly Leu Thr Pro Asp Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Asp His Gly Leu Thr Pro Asp Gln Val
                340                 345                 350

Val Ala Ile Ala Ser His Asp Gly Gly Lys Gln Ala Leu Glu Thr Val
        355                 360                 365

Gln Arg Leu Leu Pro Val Leu Cys Gln Asp His Gly Leu Thr Pro Asp
        370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Gly Gly Gly Lys Gln Ala
                420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Asn His Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn His Gly
                485                 490                 495

Gly Lys Gln Ala Leu Glu Thr Val Gln Arg Leu Leu Pro Val Leu Cys
                500                 505                 510

Gln Asp His Gly Leu Thr Pro Asp Gln Val Val Ala Ile Ala Ser Asn
        515                 520                 525

His Gly Gly Lys Gln Ala Leu Glu Thr Val Gln Arg Leu Leu Pro Val
        530                 535                 540

Leu Cys Gln Asp His Gly Leu Thr Pro Asp Gln Val Val Ala Ile Ala
545                 550                 555                 560

Ser Asn His Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
                580                 585                 590

Ile Ala Ser Asn His Gly Gly Lys Gln Ala Leu Glu Thr Val Gln Arg
        595                 600                 605
```

```
Leu Leu Pro Val Leu Cys Gln Asp His Gly Leu Thr Pro Asp Gln Val
    610             615                 620

Val Ala Ile Ala Ser His Asp Gly Gly Lys Gln Ala Leu Glu Thr Val
625             630                 635                 640

Gln Arg Leu Leu Pro Val Leu Cys Gln Asp His Gly Leu Thr Pro Asp
                645             650                 655

Gln Val Val Ala Ile Ala Ser His Asp Gly Gly Lys Gln Ala Leu Glu
            660             665                 670

Thr Val Gln Arg Leu Leu Pro Val Leu Cys Gln Asp His Gly Leu Thr
        675             680                 685

Pro Asp Gln Val Val Ala Ile Ala Ser His Asp Gly Gly Lys Gln Ala
    690             695                 700

Leu Glu Thr Val Gln Arg Leu Leu Pro Val Leu Cys Gln Asp His Gly
705             710                 715                 720

Leu Thr Pro Asp Gln Val Val Ala Ile Ala Ser His Asp Gly Gly Arg
                725             730                 735

Pro Ala Leu Glu Ser Ile Val Ala Gln Leu Ser Arg Pro Asp Pro Ala
            740             745                 750

Leu Ala Ala Leu Thr Asn Asp His Leu Val Ala Leu Ala Cys Leu Gly
        755             760                 765

Gly Arg Pro Ala Leu Asp Ala Val Lys Lys Gly Leu Pro His Ala Pro
    770             775                 780

Ala Leu Ile Lys Arg Thr Asn Arg Arg Ile Pro Glu Arg Thr Ser His
785             790                 795                 800

Arg Val Ala Gly Ser
                805
```

```
<210> SEQ ID NO 157
<211> LENGTH: 907
<212> TYPE: PRT
<213> ORGANISM: Artificial sequence
<220> FEATURE:
<223> OTHER INFORMATION: synthetic sequence

<400> SEQUENCE: 157
```

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
        130                 135                 140

Thr Gly Gln Leu Leu Lys Ile Ala Lys Arg Gly Gly Val Thr Ala Val
145                 150                 155                 160
```

-continued

```
Glu Ala Val His Ala Trp Arg Asn Ala Leu Thr Gly Ala Pro Leu Asn
             165             170             175

Leu Thr Pro Asp Gln Val Val Ala Ile Ala Ser His Asp Gly Gly Lys
             180             185             190

Gln Ala Leu Glu Thr Val Gln Arg Leu Leu Pro Val Leu Cys Gln Asp
             195             200             205

His Gly Leu Thr Pro Asp Gln Val Val Ala Ile Ala Ser His Asp Gly
     210             215             220

Gly Lys Gln Ala Leu Glu Thr Val Gln Arg Leu Leu Pro Val Leu Cys
225             230             235             240

Gln Asp His Gly Leu Thr Pro Asp Gln Val Val Ala Ile Ala Ser Asn
             245             250             255

Gly Gly Gly Lys Gln Ala Leu Glu Thr Val Gln Arg Leu Leu Pro Val
             260             265             270

Leu Cys Gln Asp His Gly Leu Thr Pro Asp Gln Val Val Ala Ile Ala
             275             280             285

Ser His Asp Gly Gly Lys Gln Ala Leu Glu Thr Val Gln Arg Leu Leu
     290             295             300

Pro Val Leu Cys Gln Asp His Gly Leu Thr Pro Asp Gln Val Val Ala
305             310             315             320

Ile Ala Ser Asn Gly Gly Gly Lys Gln Ala Leu Glu Thr Val Gln Arg
             325             330             335

Leu Leu Pro Val Leu Cys Gln Asp His Gly Leu Thr Pro Asp Gln Val
             340             345             350

Val Ala Ile Ala Ser Asn Gly Gly Gly Lys Gln Ala Leu Glu Thr Val
             355             360             365

Gln Arg Leu Leu Pro Val Leu Cys Gln Asp His Gly Leu Thr Pro Asp
     370             375             380

Gln Val Val Ala Ile Ala Ser Asn His Gly Gly Lys Gln Ala Leu Glu
385             390             395             400

Thr Val Gln Arg Leu Leu Pro Val Leu Cys Gln Asp His Gly Leu Thr
             405             410             415

Pro Asp Gln Val Val Ala Ile Ala Ser Asn His Gly Gly Lys Gln Ala
             420             425             430

Leu Glu Thr Val Gln Arg Leu Leu Pro Val Leu Cys Gln Asp His Gly
             435             440             445

Leu Thr Pro Asp Gln Val Val Ala Ile Ala Ser Asn His Gly Gly Lys
     450             455             460

Gln Ala Leu Glu Thr Val Gln Arg Leu Leu Pro Val Leu Cys Gln Asp
465             470             475             480

His Gly Leu Thr Pro Asp Gln Val Val Ala Ile Ala Ser Asn His Gly
             485             490             495

Gly Lys Gln Ala Leu Glu Thr Val Gln Arg Leu Leu Pro Val Leu Cys
             500             505             510

Gln Asp His Gly Leu Thr Pro Asp Gln Val Val Ala Ile Ala Ser Asn
             515             520             525

His Gly Gly Lys Gln Ala Leu Glu Thr Val Gln Arg Leu Leu Pro Val
             530             535             540

Leu Cys Gln Asp His Gly Leu Thr Pro Asp Gln Val Val Ala Ile Ala
545             550             555             560

Ser His Asp Gly Gly Lys Gln Ala Leu Glu Thr Val Gln Arg Leu Leu
             565             570             575

Pro Val Leu Cys Gln Asp His Gly Leu Thr Pro Asp Gln Val Val Ala
```

-continued

```
          580                   585                   590
Ile Ala Ser His Asp Gly Gly Lys Gln Ala Leu Glu Thr Val Gln Arg
        595                   600                   605

Leu Leu Pro Val Leu Cys Gln Asp His Gly Leu Thr Pro Asp Gln Val
      610                   615                   620

Val Ala Ile Ala Ser His Asp Gly Gly Lys Gln Ala Leu Glu Thr Val
625                   630                   635                   640

Gln Arg Leu Leu Pro Val Leu Cys Gln Asp His Gly Leu Thr Pro Asp
                  645                   650                   655

Gln Val Val Ala Ile Ala Ser His Asp Gly Gly Lys Gln Ala Leu Glu
              660                   665                   670

Thr Val Gln Arg Leu Leu Pro Val Leu Cys Gln Asp His Gly Leu Thr
          675                   680                   685

Pro Asp Gln Val Val Ala Ile Ala Ser Asn Gly Gly Gly Lys Gln Ala
          690                   695                   700

Leu Glu Thr Val Gln Arg Leu Leu Pro Val Leu Cys Gln Asp His Gly
705                   710                   715                   720

Leu Thr Pro Asp Gln Val Val Ala Ile Ala Ser Asn Gly Gly Gly Lys
                  725                   730                   735

Gln Ala Leu Glu Thr Val Gln Arg Leu Leu Pro Val Leu Cys Gln Asp
                  740                   745                   750

His Gly Leu Thr Pro Asp Gln Val Val Ala Ile Ala Ser His Asp Gly
              755                   760                   765

Gly Lys Gln Ala Leu Glu Thr Val Gln Arg Leu Leu Pro Val Leu Cys
      770                   775                   780

Gln Asp His Gly Leu Thr Pro Asp Gln Val Val Ala Ile Ala Ser His
785                   790                   795                   800

Asp Gly Gly Lys Gln Ala Leu Glu Thr Val Gln Arg Leu Leu Pro Val
                  805                   810                   815

Leu Cys Gln Asp His Gly Leu Thr Pro Asp Gln Val Val Ala Ile Ala
              820                   825                   830

Ser His Asp Gly Gly Arg Pro Ala Leu Glu Ser Ile Val Ala Gln Leu
          835                   840                   845

Ser Arg Pro Asp Pro Ala Leu Ala Ala Leu Thr Asn Asp His Leu Val
      850                   855                   860

Ala Leu Ala Cys Leu Gly Gly Arg Pro Ala Leu Asp Ala Val Lys Lys
865                   870                   875                   880

Gly Leu Pro His Ala Pro Ala Leu Ile Lys Arg Thr Asn Arg Arg Ile
                  885                   890                   895

Pro Glu Arg Thr Ser His Arg Val Ala Gly Ser
              900                   905
```